(12) United States Patent
Inoue et al.

(10) Patent No.: US 10,947,313 B2
(45) Date of Patent: Mar. 16, 2021

(54) ANTI-EPHA4 ANTIBODY

(71) Applicant: EISAI R&D MANAGEMENT CO., LTD., Tokyo (JP)

(72) Inventors: Eiji Inoue, Kobe (JP); Akio Yamada, Kobe (JP); Tomomi Kawakatsu, Kobe (JP); Toshio Imai, Kobe (JP); Maki Deguchi, Kobe (JP); Aki Nakatani, Kobe (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 16/915,412

(22) Filed: Jun. 29, 2020

(65) Prior Publication Data

US 2021/0002378 A1 Jan. 7, 2021

(30) Foreign Application Priority Data

Jul. 1, 2019 (JP) ............................. JP2019-122982

(51) Int. Cl.
| | | |
|---|---|---|
| C07K 16/28 | (2006.01) | |
| A61K 39/395 | (2006.01) | |
| A61P 25/28 | (2006.01) | |
| A61K 39/00 | (2006.01) | |

(52) U.S. Cl.
CPC .......... *C07K 16/2866* (2013.01); *A61P 25/28* (2018.01); *A61K 2039/505* (2013.01); *C07K 2317/24* (2013.01); *C07K 2317/565* (2013.01)

(58) Field of Classification Search
CPC .............. A61P 25/28; A61K 2039/505; C07K 2317/24; C07K 2317/565
See application file for complete search history.

(56) References Cited

U.S. PATENT DOCUMENTS

| | | | |
|---|---|---|---|
| 5,876,946 | A | 3/1999 | Burbaum et al. |
| 5,902,732 | A | 5/1999 | Hochman |
| 7,892,769 | B2 | 2/2011 | Inoue et al. |
| 7,910,324 | B2 | 3/2011 | Inoue |
| 8,137,926 | B2 | 3/2012 | Inoue |
| 8,530,181 | B2 | 9/2013 | Inoue |
| 2002/0068361 | A1 | 6/2002 | Clary |
| 2004/0180823 | A1 | 9/2004 | Pasquale et al. |
| 2005/0013819 | A1 | 1/2005 | Kinch et al. |
| 2006/0241074 | A1 | 10/2006 | Woolf et al. |
| 2006/0275856 | A1 | 12/2006 | Okochi et al. |
| 2007/0015145 | A1 | 1/2007 | Woolf et al. |
| 2007/0026409 | A1 | 2/2007 | Woolf et al. |
| 2007/0253954 | A1 | 11/2007 | Nakamura et al. |
| 2008/0213250 | A1 | 9/2008 | Hopf et al. |
| 2009/0023158 | A1 | 1/2009 | Shapiro et al. |
| 2009/0142788 | A1 | 6/2009 | Inoue |
| 2009/0163594 | A1 | 6/2009 | Shapiro et al. |
| 2009/0191211 | A1 | 7/2009 | Nakatsuru et al. |
| 2009/0191580 | A1 | 7/2009 | Inoue |
| 2009/0275049 | A1 | 11/2009 | Inoue et al. |
| 2010/0021950 | A1 | 1/2010 | Lammert et al. |
| 2010/0113415 | A1 | 5/2010 | Rajapakse et al. |
| 2010/0166657 | A1 | 7/2010 | Kinch et al. |
| 2010/0190184 | A1 | 7/2010 | Inoue |
| 2010/0255522 | A1 | 10/2010 | Inoue |
| 2011/0104171 | A1 | 5/2011 | Inoue et al. |
| 2011/0111444 | A1 | 5/2011 | Inoue |
| 2013/0288278 | A1 | 10/2013 | Inoue |
| 2014/0080146 | A1 | 3/2014 | Obara et al. |
| 2014/0143897 | A1 | 5/2014 | Robberecht |
| 2017/0218075 | A1 | 8/2017 | Ip et al. |

FOREIGN PATENT DOCUMENTS

| | | |
|---|---|---|
| EP | 0351585 | 6/1989 |
| EP | 1514925 | 3/2005 |
| EP | 1662259 | 5/2006 |
| EP | 1693449 | 8/2006 |
| EP | 1947193 | 7/2008 |
| EP | 1815255 | 4/2009 |
| EP | 2166110 | 3/2010 |
| EP | 2177623 | 4/2010 |
| EP | 2192181 | 6/2010 |
| EP | 2219028 | 8/2010 |
| EP | 2223999 | 9/2010 |
| EP | 2260864 | 12/2010 |
| JP | 2824433 | 11/1998 |
| JP | 2003-169699 | 6/2003 |
| JP | 3680114 | 8/2005 |

(Continued)

OTHER PUBLICATIONS

Cummings et al., Alzheimer's & Dementia: Translational Research & Clinical Interventions, 2019, 5: 272-293.*
Imbimbo et al., Expert Opinion on Investigational Drugs, published online Jul. 26, 2020, pp. 1-15.*
Madav et al., Brain Research Bulletin, 2019, 146: 171-184.*
[No Author Listed], "Aiming for Start of Clinical Trials Within 5 Years—New AD Therapeutic Drug—Synapse Protection—Suppresses Reductions in Cognitive Function," Chemical Daily, Jun. 2015, 2 pages.
[No Author Listed], "Eisai Scientific Day," Presentation, Eisai Co. Ltd., Human Health Care, New York, Jun. 29, 2016, 141 pages.
[No Author Listed], "Eisai Scientific Meeting 2019," Presentation, Eisai Co., Ltd., dated Apr. 23, 2019, 137 pages.

(Continued)

*Primary Examiner* — Hong Sang
(74) *Attorney, Agent, or Firm* — Fish & Richardson P.C.

(57) ABSTRACT

Provided is an anti-EphA4 antibody that can bind to EphA4 and enhance the cleavage of EphA4, as well as a pharmaceutical composition comprising the antibody as the active ingredient.
A mouse anti-EphA4 antibody that has binding affinity towards EphA4 and can enhance the cleavage of EphA4 was obtained, and the sequence of the complementarity-determining region (CDR) of the mouse anti-EphA4 antibody was identified. Subsequently, the anti-EphA4 antibody of interest was obtained by producing a humanized antibody of the mouse anti-EphA4 antibody.

15 Claims, 15 Drawing Sheets

Specification includes a Sequence Listing.

(56) References Cited

FOREIGN PATENT DOCUMENTS

| | | |
|---|---|---|
| JP | 2007-522096 | 8/2007 |
| JP | 2009-531273 | 9/2009 |
| JP | 2010-285413 | 12/2010 |
| WO | WO 1998/045708 | 10/1998 |
| WO | WO 2003/016475 | 2/2003 |
| WO | WO 2004/048578 | 6/2004 |
| WO | WO 2005/045028 | 5/2005 |
| WO | WO 2005/083086 | 9/2005 |
| WO | WO 2006/026820 | 3/2006 |
| WO | WO 2006/056467 | 6/2006 |
| WO | WO 2006/061660 | 6/2006 |
| WO | WO 2008/087035 | 7/2008 |
| WO | WO 2008/150010 | 12/2008 |
| WO | WO 2009/069808 | 6/2009 |
| WO | WO 2012/081502 | 6/2012 |
| WO | WO 2012/147798 | 11/2012 |
| WO | WO 2012/156351 | 11/2012 |
| WO | WO 2016/019280 | 2/2016 |

OTHER PUBLICATIONS

[No Author Listed], "FY2009 Product Creation Meeting," Presentation, Eisai Co., Ltd., dated Dec. 18, 2009, 121 pages.
[No Author Listed], "Gramma Secretase," Wikipedia, Jan. 16, 2012, 2 pages.
[No Author Listed], "Information Meeting," Presentation, Eisai Co., Ltd., dated Mar. 10, 2017, 48 pages.
[No Author Listed], "Information Meeting," Presentation, Eisai Co., Ltd., dated Mar. 4, 2016, 55 pages.
[No Author Listed], "Information Meeting," Presentation, Eisai Co., Ltd., dated Mar. 6, 2015, 36 pages.
[No Author Listed], "Press Conference," Presentation, Eisai Co., Ltd., dated Mar. 3, 2016, 55 pages.
[No Author Listed], "Press Conference," Presentation, Eisai Co., Ltd., dated Mar. 5, 2015, 36 pages.
[No Author Listed], "Press Conference," Presentation, Eisai Co., Ltd., dated Mar. 9, 2017, 48 pages.
[No Author Listed], "Proteomics Analysis for Drug Development and Protein Investigation (Yodosha)," Article disclosed in Zikken Igaku (Experimental Medicine) (Separate Volume), Jul. 15, 2010, 8 pages.
[No Author Listed], "Spotlight on Kobe—Cultivating biomedical innovation," NatureJobs, Nature, Jan. 2014, 505(7482), 20 pages, doi:10.1038/nj0417.
[No Author Listed], "γ-Secretase Drives Spine Formation via Novel Substrate," Alzforum Networking for a Cure, May 2009, 3 pages.
[No Author Listed], Slides used in Japan Neuroscience Society Conference, Presentation, KAN Research Institute, Inc., Sep. 15, 2011, 11 pages.
Akimoto et al., "Hepatocyte growth factor as an enhancer of NMDA currents and synaptic plasticity in the hippocampus," Neuroscience, 2004, 128(1):155-162.
Amendment and Response to Informal Office Action in European Appln. No. 16844327.3, dated Apr. 14, 2020, 9 pages.
Amendment and Response to Search Report in Russian Appln. No. 2018106456, dated Dec. 26, 2019, 1 page (English Translation).
Amtul et al., "A Presenilin 1 Mutation Associated with Familial Frontotemporal Dementia Inhibits γ-Secretase Cleavage of APP and Notch," Neurobiology of Disease, 2002, 9(2):269-273.
Aoki et al., "EphA Receptors Direct the Differentiation of Mammalian Neural Precursor Cells through a Mitogen-activated Protein Kinase-dependent Pathway," Journal of Biological Chemistry, 2004, 279(31):32643-32650.
Aoto et al., "Bidirectional ephrin/Eph signaling in synaptic functions," Brain research, 2007, 1184:72-80.
Appeal and Amendment in Japanese Appln. No. 2009-543902, dated Nov. 19, 2013, 15 pages (with Machine Translation).
Beg et al., "α2-Chimaerin Is an Essential EphA4 Effector in the Assembly of Neuronal Locomotor Circuits," Neuron, 2007, 55:768-778.

Belfiore et al., "Temporal and regional progression of Alzheimer's disease-like pathology in 3xTg-AD mice," Aging Cell, Feb. 2019, 18(1):e12873, 13 pages.
Boros et al., "Dendritic Spines Provide Cognitive Resilience against Alzheimer's Disease," Ann Neurol., Oct. 2017, 82(4):602-614.
Brack et al., "Neuropathological stageing of Alzheimer-related changes," Acta Neuropathol, 1991, 82:239-259.
Cancino et al., "c-Abl tyrosine kinase modulates tau pathology and Cdk5 phosphorylation in AD transgenic mice," Neurobiol Aging., Jul. 2011, 32(7):1249-1261.
Carter, "Alzheimer's Disease: APP, Gamma Secretase, APOE, CLU, CR1, PICALM, ABCA7, BIN1, CD2AP, CD33, EPHA1, and MS4A2, and Their Relationships with Herpes Simplex, C. Pneumoniae, Other Suspect Pathogens, and the Immune System," International J. of Alzheimer's Disease, 2011, 2011:1-34.
Cheng et al., "γ-Secretase activity is dispensable for mesenchyme-to-epithelium transition but required for podocyte and proximal tubule formation in developing mouse kidney," Development, 2003, 130(20):5031-5042.
Communication Pursuant to Rule 159 and Rule 58 EPC in European Appln. No. 16844327.3, dated Jun. 29, 2018, 2 pages.
Communication under Rule 71(3) EPC in European Appln. No. 08765357.2, dated Sep. 8, 2011, 369 pages.
Communication under Rule 71(3) EPC in European Appln. No. 08849729.2, dated Apr. 26, 2012.
Communication under Rule 71(3) EPC in European Appln. No. 08853626.3, dated Mar. 16, 2017.
Communication under Rule 71(3) EPC in European Appln. No. 11848175.3, dated Apr. 14, 2016.
Communication under Rule 71(3) EPC in European Appln. No. 12776929.7, dated May 16, 2017, 49 pages.
Communication under Rule 71(3) EPC in European Appln. No. 16844327.3, dated Jun. 10, 2020.
Decision of Refusal in Japanese Appln. No. 2009-543902, dated Aug. 12, 2013, 6 pages (with Machine Translation).
Decision to Grant a Patent in Japanese Appln. No. 2009-517923, dated Mar. 4, 2014, 5 pages (with Machine Translation).
Decision to Grant a Patent in Japanese Appln. No. 2009-543902, dated Feb. 25, 2014, 5 pages (with Machine Translation).
Decision to Grant a Patent in Japanese Appln. No. 2012-548763, dated Nov. 15, 2016, 5 pages (with Machine Translation).
Decision to Grant a Patent in Japanese Appln. No. 2013-512405, dated Jun. 7, 2016, 5 pages (with Machine Translation).
Decision to Grant Patent in Japanese Appln. No. 2017-539163, dated Jun. 24, 2020, 6 pages (with English Translation).
Decision to Grant Patent in Japanese Appln. No. 2019-152823, dated Aug. 27, 2020, 6 pages (with English Translation).
Decision to Grant Patent in Russian Appln. No. 2018106456, dated Feb. 13, 2020, 13 pages (with English Translation).
Dufour et al., "Genetic analysis of EphA-dependent signaling mechanisms controlling topographic mapping in vivo," Development, Oct. 2006, 133:4415-4420.
Eriksen et al., "NSAIDs and enantiomers of flurbiprofen target γ-secretase and lower Aβ42 in vivo," J. Clin. Invest., 2003, 112:440-449.
Esumi et al., "Expression of receptor tyrosine kinase EphA4 in normal spinal cord and autopsied spinal cord with ALS," Department of Neurology, Mishuku Hospital, 2001, pp. 48-50 (with English Translation).
Ethell et al., "Matrix Metalloproteinases in Brain Development and Remodeling: Synaptic Functions and Targets," Journal of Neuroscience Research, 2007, 85:2813-2823.
Extended European Search Report in European Appln. No. 08765357.2, dated Jun. 25, 2010, 5 pages.
Extended European Search Report in European Appln. No. 08791346.3, dated Nov. 29, 2010, 9 pages.
Extended European Search Report in European Appln. No. 08792114.4, dated Nov. 9, 2010, 6 pages.
Extended European Search Report in European Appln. No. 08849729.2, dated Nov. 26, 2010, 8 pages.
Extended European Search Report in European Appln. No. 08853626.3, dated Apr. 4, 2011, 8 pages.

(56) References Cited

OTHER PUBLICATIONS

Extended European Search Report in European Appln. No. 11848175.3, dated Jul. 21, 2014, 6 pages.
Extended European Search Report in European Appln. No. 12776929.7, dated Nov. 6, 2014, 7 pages.
Extended European Search Report in European Appln. No. 16844327.3, dated Apr. 1, 2019, 8 pages.
Final Office Action in U.S. Appl. No. 12/175,595 dated Nov. 8, 2011, 22 pages.
Final Office Action in U.S. Appl. No. 14/113,385, dated Jan. 20, 2016, 16 pages.
Folstein et al., "Mini-Mental State," J Psychiatr Res, 1975, 12:189-198.
Foveau et al., "Down-Regulation of the Met Receptor Tyrosine Kinase by Presenilin-dependent Regulated Intramembrane Proteolysis," Molecular Biology of the Cell, May 2009, 20:2495-2507.
Fox et al., "cDNA cloning and tissue distribution of five human EPH-like receptor protein-tyrosine kinases," Oncogene, 1995, 10(5):897-905.
Fraering, et al., "γ-Secretase Substrate Selectivity Can Be Modulated Directly via Interaction with a Nucleotide-binding Site," Journal of Biological Chemistry, Oct. 2005, 280(51):41987-41996.
Fu et al., "Blockade of EphA4 signaling ameliorates hippocampal synaptic dysfunctions in mouse models of Alzheimer's disease," Proc Nat'l Acad Sci USA, Jul. 2014, 111(27): 9959-64.
Gähwiler, "Organotypic Cultures of Neural Tissue," Trends Neurosci., 1988, 11:484-489.
Galasko et al., "An Inventory to Assess. Activities of Daily Living for Clinical Trials in Alzheimer's Disease," Alzheimer Dis. Assoc. Disord., 1997, 11(suppl 2): S33-S39.
Georgakopoulos et al., "Metalloproteinase/Presenilin 1 Processing of ephrinB regulates EphB-induced Src phosphorylation and signaling," The EMBO Journal, 2006, 25:1242-1252.
Goldshmit et al., "EphA4 Blockers Promote Axonal Regeneration and Functional Recovery Following Spinal Cord Injury in Mice," PLoS One, 2011, 6(9):e24636, 12 pages.
Grayson et al., "Assessment of disease-related cognitive impairments using the novel object recognition (NOR) task in rodents," Behav Brain Res., May 2015, 285:176-193.
Grisendi, "Research Highlights," Nature Cell Biology, 2009, 11(6):684, 1 page.
Haapasalo et al., "Presenilin/γ-secretase-mediated Cleavage Regulates Association of Leukocyte—Common Antigen-related (LAR) Receptor Tyrosine Phosphatase and β-Catenin," Journal of Biological Chemistry, 2007, 282(12):9063-9072.
Hansson et al., "Nicastrin, Presenilin, APH-1, and PEN-2 Form Active γ-Secretase Complexes in Mitochondria*," J. Biol. Chem., 2004, 279(49)51654-51660.
Hardy et al., "The Amyloid Hypothesis of Alzheimer's Disease: Progress and Problems on the Road to Therapeutics," Science, 2002, 297(5580):353-356.
Hering et al., "Dendritic Spines: Structure, Dynamics and Regulation," Nat Rev Neurosci., 2001, 2(12):880-888.
Holmberg et al., "Regulation of repulsion versus adhesion by different splice forms of an Eph receptor," Nature, 2000, 408(6809):203-206.
Houston et al., "The chemical-biological interface: developments in automated and miniaturised screening technology," Curr. Opin. Biotechnol., 1997, 8:734-740.
Huang et al., "SORLA attenuates EphA4 signaling and amyloid β-induced neurodegeneration," J Exp Med., Nov. 2017, 214(12):3669-3685.
Inoue "EphA4/γ-secretase signal changes in Alzheimer's Disease," KAN Research Institute, Inc., Medical Science Digest, Jun. 2016, 6 pages.
Inoue et al., "Change in EphA4/gamma-secretase signal in brain with Alzheimer's disease (AD)," KAN Research Institute, Inc., Dementia Japan, 25(3):339 (with English Translation) 2011.
Inoue et al., "Synaptic activity prompts γ-secretase-mediated cleavage of EphA4 and dendritic spine formation," Journal of Cell Biology, May 2009, 185(3):551-564.
Inoue, "Changes of EphA4/gamma-secretase signals in Alzheimer's Disease (AD) brain," Slides presented at The Japan Society for Dementia Research Conference, KAN Research Institute, Inc., Nov. 11, 2011, 20 pages.
Inoue, "Formation and Obstacle of Memory From Basic to Clinical-Spine Formation Control Mechanisms by γ-secretase," Slides presented at 27th Wako Workshop, KAN Research Institute, Inc., Nov. 22, 2011, 27 pages (with English Cover Page).
Inoue, "Pathological analysis of Alzheimer's disease based on the physiological function of γ-secretase," Slides presented at the Advanced Medical Center Video Research Conference, KAN Research Institute, Inc., Nov. 27, 2012, 39 pages (with English Cover Page).
Inoue, "Proteomic Analysis of γ-secretase Substrates," Slides presented at the Proteome Organization Conference, Jul. 27, 2009, KAN Research Institute, Inc., 2009, 19 pages.
Invitrogen.com, [Online], "Mouse anti-EphA4 Receptor," Catalog No. 37-1600, Retrieved on Apr. 5, 2013, retrieved from URL<www.invitrogen.com>, 2 pages.
Jayawickreme et al., "Gene expression systems in the development of high-throughput screens," Curr. Opin. Biotechnol., 1997, 8:629-634.
Kaether et al., "Assembly, Trafficking and Function of γ-Secretase," Neurodegener Dis., 2006, 3(4-5):275-283.
Kawarabayashi et al., "Age-Dependent Changes in Brain, CSF, and Plasma Amyloid β Protein in the Tg2576 Transgenic Mouse Model of Alzheimer's Disease," J. Neurosci., 2001, 21(2):372-381.
Kayman et al., "Cognitive Deficits in Schizophrenia," Current Translational Geriatrics and Experimental Gerontology Reports, Feb. 2012, 1:45-52.
Khachaturian, "Diagnosis of Alzheimer's Disease," Arch Neuro, 1985, 42:1097-1105.
Koehler et al., "Continuous Cultures of Fused Cells Secreting Antibody of Predefined Specificity," Nature, 1975, 256:495-97.
Kopan et al., "γ-Secretase: proteasome of the membrane?," Nature Reviews Molecular Cell Biology, 2004, 5(6):499-504.
Kullander et al., "Mechanisms and Functions of Eph and Ephrin Signalling," Nature Reviews, Molecular Cell Biology, 2002, 3:475-486.
Kuure et al., "Crosstalk between Jagged1 and GDNF/Ret/GFRα1 signalling regulates ureteric budding and branching," Mechanisms of Development, 2005, 122(6):765-780.
Lai et al., "Synapse development and plasticity: roles of ephrin/Eph receptor signaling," Current Opinion in Neurobiology, 2009, 19:275-283.
Landman et al., "Got RIP?: Presenilin-dependent intramembrane proteolysis in growth factor receptor signaling," Cytokine & Growth Factor Reviews, Oct. 2004, 15:337-351.
Lanz et al., "The γ-Secretase Inhibitor N-[N-(3,5-Difluorophenacetyl)-L-alanyl]S-phenylglycine t-butyl Ester Reduces Aβ Levels in Vivo in Plasma and Cerebrospinal Fluid in Young (Plaque-Free) and Aged (Plaque-Bearing) Tg2576 Mice," J. Pharmacol. Exp. Ther., 2003, 305:864-871.
Lee et al., "Presenilin-dependent γ-Secretase-like Intramembrane Cleavage of ErbB4," Journal of Biological Chemistry, Feb. 2002, 277:6318-6323.
Lin et al., "Ephrin-B2-induced Cleavage of EphB2 Receptor Is Mediated by Matrix Metalloproteinases to Trigger Cell Repulsion," Journal of Biological Chemistry, Aug. 2008, 283(43):28969-28979.
Litterst et al., "Ligand Binding and Calcium Influx Induce Distinct Ectodomain/γ-Secretase-processing Pathways of EphB2 Receptor," Journal of Biological Chemistry, 2007, 282(22):16155-16163.
Liu et al., "Intramembrane proteolysis of human NotchdeltaE," Society for Neuroscience Abstract Viewer and Itinerary Planner, 33rd Annual Meeting of the Society of Neuroscience, 2003, Abstract No. 729.11, vol. 2003, Last updated Apr. 2004, 1 page (Abstract only).
Maretzky et al., "L1 is sequentially processed by two differently activated metalloproteases and presenilin/γ-secretase and regulates neural cell adhesion, cell migration, and neurite outgrowth," Molecular and Cellular Biology, 2005, 25(20):9040-9053.

(56) References Cited

OTHER PUBLICATIONS

Martone et al., "Immunolocalization of the receptor tyrosine kinase EphA4 in the adult rat central nervous system," Brain Research, Oct. 1997, 771(2):238-250.
Massimiliano et al., "Are We Using the Right Pharmacological Tools to Target EphA4?," ACS Chemical Neuroscience, 2014, 5:1146-1147.
Matsui et al., "Involvement of the γ-Secretase-Mediated EphA4 Signaling Pathway in Synaptic Pathogenesis of Alzheimer's Disease," Brain Pathol., Nov. 2012, 22(6):776-787.
Maulik et al., "Role of the hepatocyte growth factor receptor, c-Met, in oncogenesis and potential for therapeutic inhibition," Cytokine Growth Factor Rev., 2002, 13(1):41-59.
McKhann et al., "Clinical diagnosis of Alzheimer's disease: Report of the NINCDS-ADRDA Work Group* under the auspices of Department of Health and Human Services Task Force on Alzheimer's Disease," Neurology, 1984, 34:939-944.
McLendon et al., "Cell-free assays for γ-secretase activity," The FASEB Journal, 2000, 14:2383-2386.
Minopoli et al., "Receptor- and Non-Receptor Tyrosine Kinases Induce Processing of the Amyloid Precursor Protein: Role of the Low-Density Lipoprotein Receptor-Related Protein," Neurodegenerative Diseases, 2007, 4(2-3):94-100.
Mirra et al., "Making the Diagnosis of Alzheimer's Disease," Arch Pathol Lab Med, 1993, 117:132-144.
Mirra et al., "The Consortium to Establish a Registry for Alzheimer's Disease (CERAD)—Part II. Standardization of the neuropathologic assessment of Alzheimer's disease," Neurology, 1991, 41:479-486.
Moehlmann et al., "Presenilin-1 mutations of leucine 166 equally affect the generation of the Notch and APP intracellular domains independent of their effect on $A\beta_{42}$ production," PNAS, 2002, 99:8025-8030.
Mohs et al., "Comprehensive and Neuropsychologic Evaluations—The Alzheimer's Disease Assessment Scale," Int. Psychogeriatr., 1996, 8:195-203.
Murai et al., "Control of hippocampal dendritic spine morphology through ephrin-A3/EphA4 signaling," Nature Neuroscience, 2003, 6(2):153-160.
Muramatsu et al., "Gelatinase [gelatinase]; [Corresponding Part 'gelatinase' from p. 457, right column, line 38 to p. 458, left column, line 5," Dictionary of Molecular Cell Biology, Printed by (Enterprise) Showado Insatsudo, First Print: Issued on Mar. 10, 1997, 6 pages (with English Translation).
Murphy et al., "γ-Secretase, Evidence for Multiple Proteolytic Activities and Influence of Membrane Positioning of Substrate on Generation of Amyloid β Peptides of Varying Length," Journal of Biological Chemistry, 1999, 274(17):11914-11923.
Nakanishi et al., "ALL1 fusion proteins induce deregulation of EphA7 and ERK phosphorylation in human acute leukemias," Proceedings of the National Academy of Sciences, Sep. 2007, 104(36):14442-14447.
Nath et al., "Shedding of c-Met is regulated by crosstalk between a G-protein coupled receptor and the EGF receptor and is mediated by a TIMP-3 sensitive metalloproteinase," Journal of Cell Science, 2001, 114:1213-1220.
NCBI Accession No. XM_244186.3, "Predicted: Rattus norvegicus similar to Eph receptor A4 (LOC316539), mRNA," Apr. 2005, Search Date: Feb. 21, 2012, 6 pages.
Niwa et al., "Efficient selection for high-expression transfectants with a novel eukaryotic vector," Gene, 1991, 108:193-200.
Noberini et al., "Small Molecules Can Selectively Inhibit Ephrin Binding to the EphA4 and EphA2 Receptors*," The Journal of Biological Chemistry, 2008, 283(43):29461-29472.
Non-Final Office Action in U.S. Appl. No. 12/135,307, dated Jun. 10, 2010, 7 pages.
Non-Final Office Action in U.S. Appl. No. 12/325,418, dated Apr. 1, 2010, 13 pages.
Non-Final Office Action in U.S. Appl. No. 12/986,922, dated Apr. 10, 2013, 24 pages.
Non-Final Office Action in U.S. Appl. No. 13/009,127, dated Jul. 13, 2011, 7 pages.
Non-Final Office Action in U.S. Appl. No. 13/993,126, dated Feb. 28, 2014, 11 pages.
Non-Final Office Action in U.S. Appl. No. 14/113,385, dated Jul. 6, 2015, 30 pages.
Non-Final Office Action in U.S. Appl. No. 14/113,385, dated Nov. 29, 2016, 13 pages.
Notice of Allowance in U.S. Appl. No. 12/135,307, dated Oct. 21, 2010, 7 pages.
Notice of Allowance in U.S. Appl. No. 12/325,418, dated Oct. 8, 2010, 14 pages.
Notice of Allowance in U.S. Appl. No. 12/742,312, dated Nov. 5, 2012, 12 pages.
Notice of Allowance in U.S. Appl. No. 13/009,127, dated Nov. 17, 2011, 5 pages.
Notice of Allowance in U.S. Appl. No. 13/993,126, dated Aug. 22, 2014, 5 pages.
Notice of Allowance in U.S. Appl. No. 13/993,126, dated Jun. 24, 2014, 5 pages.
Notice of Allowance in U.S. Appl. No. 14/113,385, dated Jul. 6, 2017, 11 pages.
Notice of Allowance in U.S. Appl. No. 15/753,611, dated Apr. 5, 2019, 12 pages.
Notice of Allowance in U.S. Appl. No. 15/753,611, dated Jul. 12, 2019, 8 pages.
Notice of Reasons for Refusal in Japanese Appln. No. 2009-517923, dated Jul. 2, 2013, 5 pages (with Machine Translation).
Notice of Reasons for Refusal in Japanese Appln. No. 2009-543902, dated Feb. 28, 2012, 6 pages (with Machine Translation).
Notice of Reasons for Refusal in Japanese Appln. No. 2009-543902, dated Nov. 6, 2012, 7 pages (with Machine Translation).
Notice of Reasons for Refusal in Japanese Appln. No. 2012-548763, dated Apr. 19, 2016, 6 pages (with Machine Translation).
Notice of Reasons for Refusal in Japanese Appln. No. 2012-548763, dated Sep. 8, 2015, 6 pages (with Machine Translation).
Notice of Reasons for Refusal in Japanese Appln. No. 2013-512405, dated Mar. 8, 2016, 8 pages (with Machine Translation).
Notice of Trial and Amendment in Japanese Appln. No. 2009-543902, dated Nov. 19, 2013, 15 pages (with English Translation).
Office Action in Colombian Appln. No. NC2018/0000652, dated Jan. 30, 2018, 4 pages (with English Translation).
Office Action in European Appln. No. 08765357.2, dated Feb. 4, 2011, 4 pages.
Office Action in European Appln. No. 08853626.3, dated Aug. 12, 2015, 6 pages.
Office Action in European Appln. No. 08853626.3, dated Aug. 5, 2013, 5 pages.
Office Action in European Appln. No. 08853626.3, dated Dec. 16, 2014, 4 pages.
Office Action in European Appln. No. 08853626.3, dated Nov. 18, 2011, 5 pages.
Office Action in European Appln. No. 08853626.3, dated Oct. 29, 2012, 4 pages.
Office Action in European Appln. No. 11848175.3, dated Dec. 4, 2015, 4 pages.
Office Action in European Appln. No. 12776929.7, dated Feb. 27, 2017, 2 pages.
Office Action in Israeli Appln. No. 256519, dated Apr. 30, 2019, 5 pages (with English Translation).
Office Action in Israeli Appln. No. 268889, dated Jun. 28, 2020, 5 pages (with English Translation).
Office Action in Japanese Appln. No. 2009-541201, dated Sep. 24, 2013, 7 pages (with English Translation).
Office Action in U.S. Appl. No. 12/175,595 dated May 17, 2011, 16 pages.
Office Action in U.S. Appl. No. 12/175,595, dated Apr. 18, 2012, 17 pages.
Office Action in U.S. Appl. No. 12/670,987, dated Apr. 5, 2012, 29 pages.
Office Action in U.S. Appl. No. 12/742,312, dated Jul. 17, 2012, 24 pages.

(56) References Cited

OTHER PUBLICATIONS

Office Action in U.S. Appl. No. 12/742,312, dated May 14, 2012, 5 pages.
Ohta et al., "The receptor tyrosine kinase, Cek8, is transiently expressed on subtypes of motoneurons in the spinal cord during development," Mechanisms of Development, 1996, 54:59-69.
Onishi et al., "A novel glycogen synthase kinase-3 inhibitor 2-methyl-5-(3-{4-[(S)-methylsulfinyl]phenyl}-1-benzofuran-5-yl)-1,3,4-oxadiazole decreases tau phosphorylation and ameliorates cognitive deficits in a transgenic model of Alzheimer's disease," J Neurochem., 2011, 119(6):1330-40.
Pagonabarraga et al., "Cognitive impairment and dementia in Parkinson's disease," Neurobiology of Disease, 2012, 46:590-596.
Pak et al., "Regulation of Dendritic Spine Morphology by SPAR, a PSD-95-Associated RapGAP," Neuron, 2001, 31:289-303.
Patrick et al., "Conversion of p35 to p25 deregulates Cdk5 activity and promotes neurodegeneration," Nature, Dec. 1999, 402(6762):615-22.
PCT International Search Report and Written Opinion in International Appln No. PCT/JP2008/071831, dated Jan. 27, 2009, 18 pages (with English Translation).
PCT International Search Report and Written Opinion in International Appln. No. PCT/JP2008/060567, dated Aug. 26, 2008, 12 pages (with English Translation).
PCT International Search Report and Written Opinion in International Appln. No. PCT/JP2011/078460, dated Jan. 10, 2012, 17 pages (with English Translation).
PCT International Search Report and Written Opinion in International Appln. No. PCT/JP2012/061097, dated Aug. 7, 2012, 18 pages (with English Translation).
PCT International Search Report and Written Opinion in International Appln. No. PCT/JP2016/076102, dated Mar. 16, 2017, 11 pages (English Translation).
PCT International Search Report in International Appln. No. PCT/JP2008/063037, dated Sep. 9, 2008, 5 pages (with English Translation).
PCT International Search Report in International Appln. No. PCT/JP2008/063901, dated Aug. 26, 2008, 8 pages (with English Translation).
PCT International Search Report in International Appln. No. PCT/JP2008/070864, dated Jan. 6, 2009, 4 pages (with English Translation).
PCT Written Opinion in International Appln. No. PCT/JP2020/025465, dated Aug. 25, 2020, 12 pages (with English Translation).
Pelletier et al., "γ-Secretase-Dependent Proteolysis of CD44 Promotes Neoplastic Transformation of Rat Fibroblastic Cells," Cancer Research, 66(7):3681-3687 2006.
Penzes et al., "Convergent CaMK and RacGEF signals control dendritic structure and function," Trends in Cell Biology, Sep. 2008, 18(9):405-413.
Phone Consultation in European Appln. No. 08849729.2, dated Mar. 20, 2012, 3 pages.
Poppe et al., "EphA4 loss improves social memory performance and alters dendritic spine morphology without changes in amyloid pathology in a mouse model of Alzheimer's disease," Alzheimer's Research & Therapy, 2019, 11:102, 13 pages.
Pozner-Moulis et al., "Met, the Hepatocyte Growth Factor Receptor, Localizes to the Nucleus in Cells at Low Density," Cancer Research, Aug. 2006, 66:7976-7982.
Ra et al., "Control of Matrix Metalloproteinase Catalytic Activity," Matrix Biol., 2007, 26(8):587-596.
Ramakers et al., "Rho proteins, mental retardation and the cellular basis of cognition," Trends in Neurosciences, Apr. 2002, 25(4):191-199.
Ramsden et al., "Age-Dependent Neurofibrillary Tangle Formation, Neuron Loss, and Memory Impairment in a Mouse Model of Human Tauopathy (P301L)," J. Neurosci., Nov. 2005, 25(46):10637-10647.
Ray et al., "Evidence for a physical interaction between presenilin and Notch," Proceedings of the National Academy of Sciences, Mar. 1999, 96(6):3263-3268.
Request for Continued Examination in U.S. Appl. No. 12/742,312, dated Feb. 5, 2013, 1 page.
Request for Continued Examination in U.S. Appl. No. 13/993,126, dated Aug. 7, 2014, 1 page.
Response to European Office Action in European Appln. No. 08765357.2, dated Jun. 1, 2011, 12 pages.
Response to European Rule 159 and Rule 58 in European Appln. No. 16844327.3, dated Aug. 28, 2018, 2 pages.
Response to Extended European Search Report in European Appln. No. 08765357.2, dated Jan. 7, 2011, 22 pages.
Response to Extended European Search Report in European Appln. No. 08853626.3, dated Oct. 21, 2011, 18 pages.
Response to Extended European Search Report in European Appln. No. 11848175.3, dated Jan. 20, 2015, 22 pages.
Response to Extended European Search Report in European Appln. No. 12776929.7, dated May 6, 2015, 8 pages.
Response to Extended European Search Report in European Appln. No. 16844327.3, dated Oct. 25, 2019, 37 pages.
Response to Final Office Action in U.S. Appl. No. 12/175,595, dated Feb. 8, 2012, 13 pages.
Response to Final Office Action in U.S. Appl. No. 14/113,385, dated Apr. 4, 2016, 11 pages.
Response to Non-Final Office Action in U.S. Appl. No. 12/135,307, dated Sep. 2, 2010, 10 pages.
Response to Non-Final Office Action in U.S. Appl. No. 12/325,418, dated Jul. 21, 2010, 18 pages.
Response to Non-Final Office Action in U.S. Appl. No. 13/009,127, dated Oct. 7, 2011, (resubmission) 7 pages.
Response to Non-Final Office Action in U.S. Appl. No. 13/009,127, dated Sep. 28, 2011, 8 pages.
Response to Non-Final Office Action in U.S. Appl. No. 13/993,126, dated May 28, 2014, 15 pages.
Response to Non-Final Office Action in U.S. Appl. No. 14/113,385, dated Apr. 27, 2017, 8 pages.
Response to Non-Final Office Action in U.S. Appl. No. 14/113,385, dated Oct. 6, 2015, 16 pages.
Response to Office Action in Colombian Appln. No. NC2018/0000652, dated May 24, 2018, 5 pages.
Response to Office Action in European Appln. No. 08791346.3, dated Jun. 21, 2011, 4 pages.
Response to Office Action in European Appln. No. 08792114.4, dated May 26, 2011, 4 pages.
Response to Office Action in European Appln. No. 08849729.2, dated Jun. 21, 2011, 6 pages.
Response to Office Action in European Appln. No. 08853626.3, dated Apr. 14, 2015, 34 pages.
Response to Office Action in European Appln. No. 08853626.3, dated Dec. 10, 2015, 30 pages.
Response to Office Action in European Appln. No. 08853626.3, dated Dec. 11, 2013, 29 pages.
Response to Office Action in European Appln. No. 08853626.3, dated Dec. 27, 2012, 51 pages.
Response to Office Action in European Appln. No. 08853626.3, dated Mar. 14, 2012, 16 pages.
Response to Office Action in European Appln. No. 11848175.3, dated Mar. 3, 2016, 31 pages.
Response to Office Action in European Appln. No. 12776929.7, dated Mar. 15, 2017, 16 pages.
Response to Office Action in Israeli Appln. No. 256519, dated Aug. 25, 2019, 6 pages (with English Translation).
Response to Office Action in Israeli Appln. No. 268889, dated Sep. 14, 2020, 5 pages (with English Translation).
Response to Office Action in Japanese Application No. 2009-541201, dated Nov. 18, 2013, 12 pages (with English Translation).
Response to Office Action in Japanese Appln. No. 2009-517923, dated Aug. 29, 2013, 8 pages (with Machine Translation).
Response to Office Action in Japanese Appln. No. 2009-543902, dated Apr. 27, 2012, 15 pages (with Machine Translation).
Response to Office Action in Japanese Appln. No. 2009-543902, dated Dec. 28, 2012, 19 pages (with Machine Translation).

(56) References Cited

OTHER PUBLICATIONS

Response to Office Action in Japanese Appln. No. 2012-548763, dated Jun. 14, 2016, 11 pages (with Machine Translation).
Response to Office Action in Japanese Appln. No. 2012-548763, dated Nov. 5, 2015, 26 pages (with Machine Translation).
Response to Office Action in Japanese Appln. No. 2013-512405, dated Apr. 19, 2016, 37 pages (with Machine Translation).
Response to Office Action in U.S. Appl. No. 12/175,595, dated Aug. 18, 2011, 15 pages.
Response to Office Action in U.S. Appl. No. 12/742,312, dated Jun. 11, 2012, 7 pages.
Response to Office Action in U.S. Appl. No. 12/742,312, dated Oct. 16, 2012, 14 pages.
Response to Restriction Requirement in U.S. Appl. No. 12/135,307, dated May 6, 2010, 1 page.
Response to Restriction Requirement in U.S. Appl. No. 12/325,418, dated Dec. 10, 2009, 13 pages.
Response to Restriction Requirement in U.S. Appl. No. 12/986,922, dated Feb. 4, 2013, 3 pages.
Response to Restriction Requirement in U.S. Appl. No. 13/993,126, dated Feb. 4, 2013, 11 pages.
Response to Restriction Requirement in U.S. Appl. No. 14/113,385, dated Apr. 20, 2015, 3 pages.
Restriction Requirement in U.S. Appl. No. 12/135,307, dated Mar. 19, 2010, 6 pages.
Restriction Requirement in U.S. Appl. No. 12/325,418, dated Nov. 10, 2009, 9 pages.
Restriction Requirement in U.S. Appl. No. 12/986,922, dated Jan. 18, 2013, 8 pages.
Restriction Requirement in U.S. Appl. No. 13/993,126, dated Dec. 5, 2013, 6 pages.
Restriction Requirement in U.S. Appl. No. 14/113,385, dated Mar. 2, 2015, 6 pages.
Robberecht, "Progress report of the research group of Prof Dr. Wim Robberecht," Queen Elisabeth Medical Foundation, Report 2014, Mar. 2015, 144 pages.
Rosenberger et al., "Altered distribution of the EphA4 kinase in hippocampal brain tissue of patients with Alzheimer's disease correlates with pathology," Acta Neuropathol Commun., 2014, 2:79, 13 pages.
Sakaguchi et al., "Sprouting of CA3 pyramidal neurons to the dentate gyms in rat hippocampal organotypic cultures," Neurosci. Res., 1994, 20:157-164.
Sambrook et al., "Introduction of Recombinant Vectors into Mammalian Cells," Molecular Cloning: A Laboratory Manual, 2nd Edition, 1989, 3:16.30-16.31.
SantaCruz et al., "Tau Suppression in a Neurodegenerative Mouse Model Improves Memory Function," Science, 2005, 309(5733):476-81.
Sariola et al., "Novel functions and signalling pathways for GDNF," Journal of Cell Science, 2003, 116.(pt. 19):3855-3862.
Sastre et al., "Presenilin-dependent γ-secretase processing of β-amyloid precursor protein at a site corresponding to the S3 cleavage of Notch," EMBO reports, 2001, 2(9): 835-841.
Saura et al., "Loss of Presenilin Function Causes Impairments of Memory and Synaptic Plasticity Followed by Age-Dependent Neurodegeneration," Neuron, 2004, 42(1):23-36.
Sbai et al., "Vesicular trafficking and secretion of matrix metalloproteinases-2,-9 and tissue inhibitor of metalloproteinases-1 in neuronal cells," Molecular and Cellular Neuroscience 2008, 39(4):549-568.
Search Report in Russian Appln. No. 2018106456, dated Sep. 30, 2019, 5 pages (with English Translation).
Seo et al., "Inhibition of p25/Cdk5 Attenuates Tauopathy in Mouse and iPSC Models of Frontotemporal Dementia," The Journal of Neuroscience, Oct. 2017, 37(41): 9917-9924.
Shamah et al., "EphA Receptors Regulate Growth Cone Dynamics through the Novel Guanine Nucleotide Exchange Factor Ephexin," Cell, 2001, 105(2):233-244.

Simón et al. "Early Changes in Hippocampal Eph Receptors Precede the Onset of Memory Decline in Mouse Models of Alzheimer's Disease," Journal of Alzheimer's Disease, 2009, 17:773-786.
Song et al. "Plasma biomarkers for mild cognitive impairment and Alzheimer's disease," Brain Research Reviews, 2009, 61(2):69-80.
Song et al., "Proteolytic release and nuclear translocation of Notch-1 are induced by presenilin-1 and impaired by pathogenic presenilin-1 mutations," PNAS, 1999, 96:6959-6963.
Spanevello et al., "Acute Delivery of EphA4-Fc Improves Functional Recovery after Contusive Spinal Cord Injury in Rats," Journal of Neurotrauma, 2013, 30:1023-1034.
Stoppini et al., "A simple method for organotypic cultures of nervous tissue," J. Neurosci. Methods, 1991, 37:173-182.
Tashiro et al., "Regulation of dendritic spine motility and stability by Rac1 and Rho kinase: evidence for two forms of spine motility," Molecular and Cellular Neuroscience, Jul. 2004, 26(3):429-440.
Tomita et al., "Presenilin-dependent intramembrane cleavage of ephrin-B1," Molecular Neurodegeneration, 2006, 1:1-9.
Tremblay et al., "Localization of EphA4 in Axon Terminals and Dendritic Spines of Adult Rat Hippocampus," The Journal of Comparative Neurology, 2007, 501:691-702.
Tyndall et al., "The Receptor Tyrosine Kinase Met and Its Ligand Hepatocyte Growth Factor are Clustered at Excitatory Synapses and Can Enhance Clustering of Synaptic Proteins," Cell Cycle, Jul. 2006, 5(14):1560-1568.
Van Hoecke et al., "EPHA4 is a disease modifier of amyotrophic lateral sclerosis in animal models and in humans," Nature Medicine, Sep. 2012, 18(9):1418-1422.
Vargas et al., "Amyloid-β oligomers synaptotoxicity: The emerging role of EphA4/c-Abl signaling in Alzheimer's disease," Biochim. Biophys. Acta. Mol. Basis Dis., Apr. 2018, 1864:1148-1159.
Vargas et al., "EphA4 Activation of c-Abl Mediates Synaptic Loss and LTP Blockade Caused by Amyloid-b Oligomers," PLoS One, Mar. 2014, 9(3):e92309, 13 pages.
Verbaan et al., "Cognitive impairment in Parkinson's disease," J. Neurol Neurosurg. Psychiatry, 2007, 78:1182-1187.
Vidal et al., "Presenilin-dependent γ-Secretase Processing Regulates Multiple ERBB4/HER4 Activities," Journal of Biological Chemistry, 2005, 280(20):19777-19783.
Wada et al., "Glycosylphosphatidylinositol-Anchored Cell Surface Proteins Regulate Position-Specific Cell Affinity in the Limb Bud," Developmental Biology, 1998, 202:244-252.
Wajih et al., "Vascular Origin of a Soluble Truncated Form of the Hepatocyte Growth Factor Receptor (c-met)," Circulation Research, 2002, 90:46-52.
Webster et al., "Using mice to model Alzheimer's dementia: an overview of the clinical disease and the preclinical behavioral changes in 10 mouse models," Frontiers in Genetics, Apr. 2014, 5:88, 23 pages.
Wiedemann, "Signalling Growth," Nature Reviews Neuroscience, Jul. 2009, 10:472, 1 page.
Xu et al. "Expression of truncated Sek-1 receptor tyrosine kinase disrupts the segmental restriction of gene expression in the *Xenopus* and zebrafish hindbrain." Development, 1995, 121(12):4005-1016.
Yamaguchi et al., "Eph receptors in the adult brain," Current opinion in Neurobiology, 2004, 14(3):288-296.
Yang et al., "Preparation and Analysis of Monoclonal Antibody Against EPHA4 Peptide," J. Cent South Univ. (Med Sci), 2005, 30(5):529-532, (English Translation).
Yokote et al., "Trans-activation of EphA4 and FGF receptors mediated by direct interactions between their cytoplasmic domains," Proceedings of the National Academy of Sciences, 2005, 102:18866-18871.
Zhao et al., "Role of p21-activated kinase pathway defects in the cognitive deficits of Alzheimer disease," Nature Neuroscience, Feb. 2006, 9(2):234-242.
Zou et al., "Linking Receptor-mediated Endocytosis and Cell Signaling Evidence for Regulated Intramembrane Proteolysis of Megalin in Proximal Tubule," Journal of Biological Chemistry, 2004, 279(33):34302-34310.
Office Action and Search Report in Chinese Patent Application No. 201680048438.4, dated Nov. 18, 2020, 12 pages (with English Translation).

(56) References Cited

OTHER PUBLICATIONS

Office Action in Brazilian Appln. No. BR112018003494-0, dated Dec. 22, 2020, 7 pages (with English Translation).
Office Action in Israeli Appln. 256519, dated Jan. 5, 20201, 17 pages (with partial English Translation).

\* cited by examiner

| | ka (1/Ms) | kd (1/s) | KD (M) | Rmax (RU) | Chi² (RU²) |
|---|---|---|---|---|---|
| Human EphA4 | 3.70.E+05 | 4.94.E-04 | 1.34.E-09 | 5.66 | 0.015 |

```
                        SEQUENCE LISTING

<160> NUMBER OF SEQ ID NOS: 62

<210> SEQ ID NO 1
<211> LENGTH: 986
<212> TYPE: PRT
<213> ORGANISM: Mus musculus

<400> SEQUENCE: 1

Met Ala Gly Ile Phe Tyr Phe Ile Leu Phe Ser Phe Leu Phe Gly Ile
1               5                   10                  15

Cys Asp Ala Val Thr Gly Ser Arg Val Tyr Pro Ala Asn Glu Val Thr
            20                  25                  30

Leu Leu Asp Ser Arg Ser Val Gln Gly Glu Leu Gly Trp Ile Ala Ser
        35                  40                  45

Pro Leu Glu Gly Gly Trp Glu Glu Val Ser Ile Met Asp Glu Lys Asn
    50                  55                  60

Thr Pro Ile Arg Thr Tyr Gln Val Cys Asn Val Met Glu Ala Ser Gln
65                  70                  75                  80

Asn Asn Trp Leu Arg Thr Asp Trp Ile Thr Arg Glu Gly Ala Gln Arg
                85                  90                  95

Val Tyr Ile Glu Ile Lys Phe Thr Leu Arg Asp Cys Asn Ser Leu Pro
            100                 105                 110

Gly Val Met Gly Thr Cys Lys Glu Thr Phe Asn Leu Tyr Tyr Tyr Glu
        115                 120                 125

Ser Asp Asn Asp Lys Glu Arg Phe Ile Arg Glu Ser Gln Phe Gly Lys
    130                 135                 140

Ile Asp Thr Ile Ala Ala Asp Glu Ser Phe Thr Gln Val Asp Ile Gly
145                 150                 155                 160

Asp Arg Ile Met Lys Leu Asn Thr Glu Ile Arg Asp Val Gly Pro Leu
                165                 170                 175

Ser Lys Lys Gly Phe Tyr Leu Ala Phe Gln Asp Val Gly Ala Cys Ile
            180                 185                 190

Ala Leu Val Ser Val Arg Val Phe Tyr Lys Lys Cys Pro Leu Thr Val
        195                 200                 205

Arg Asn Leu Ala Gln Phe Pro Asp Thr Ile Thr Gly Ala Asp Thr Ser
    210                 215                 220

Ser Leu Val Glu Val Arg Gly Ser Cys Val Asn Asn Ser Glu Glu Lys
225                 230                 235                 240

Asp Val Pro Lys Met Tyr Cys Gly Ala Asp Gly Glu Trp Leu Val Pro
                245                 250                 255

Ile Gly Asn Cys Leu Cys Asn Ala Gly His Glu Glu Gln Asn Gly Glu
            260                 265                 270

Cys Gln Ala Cys Lys Ile Gly Tyr Tyr Lys Ala Leu Ser Thr Asp Ala
        275                 280                 285

Ser Cys Ala Lys Cys Pro Pro His Ser Tyr Ser Val Trp Glu Gly Ala
    290                 295                 300

Thr Ser Cys Thr Cys Asp Arg Gly Phe Phe Arg Ala Asp Asn Asp Ala
```

```
            305                 310                 315                 320
Ala Ser Met Pro Cys Thr Arg Pro Pro Ser Ala Pro Leu Asn Leu Ile
                325                 330                 335

Ser Asn Val Asn Glu Thr Ser Val Asn Leu Glu Trp Ser Ser Pro Gln
                340                 345                 350

Asn Thr Gly Gly Arg Gln Asp Ile Ser Tyr Asn Val Cys Lys Lys
                355                 360                 365

Cys Gly Ala Gly Asp Pro Ser Lys Cys Arg Pro Cys Gly Ser Gly Val
                370                 375                 380

His Tyr Thr Pro Gln Gln Asn Gly Leu Lys Thr Thr Arg Val Ser Ile
385                 390                 395                 400

Thr Asp Leu Leu Ala His Thr Asn Tyr Thr Phe Glu Ile Trp Ala Val
                405                 410                 415

Asn Gly Val Ser Lys Tyr Asn Pro Ser Pro Asp Gln Ser Val Ser Val
                420                 425                 430

Thr Val Thr Thr Asn Gln Ala Ala Pro Ser Ser Ile Ala Leu Val Gln
                435                 440                 445

Ala Lys Glu Val Thr Arg Tyr Ser Val Ala Leu Ala Trp Leu Glu Pro
        450                 455                 460

Asp Arg Pro Asn Gly Val Ile Leu Glu Tyr Glu Val Lys Tyr Tyr Glu
465                 470                 475                 480

Lys Asp Gln Asn Glu Arg Ser Tyr Arg Ile Val Arg Thr Ala Ala Arg
                485                 490                 495

Asn Thr Asp Ile Lys Gly Leu Asn Pro Leu Thr Ser Tyr Val Phe His
                500                 505                 510

Val Arg Ala Arg Thr Ala Ala Gly Tyr Gly Asp Phe Ser Glu Pro Leu
        515                 520                 525

Glu Val Thr Thr Asn Thr Val Pro Ser Arg Ile Ile Gly Asp Gly Ala
                530                 535                 540

Asn Ser Thr Val Leu Leu Val Ser Val Ser Gly Ser Val Val Leu Val
545                 550                 555                 560

Val Ile Leu Ile Ala Ala Phe Val Ile Ser Arg Arg Arg Ser Lys Tyr
                565                 570                 575

Ser Lys Ala Lys Gln Glu Ala Asp Glu Glu Lys His Leu Asn Gln Gly
                580                 585                 590

Val Arg Thr Tyr Val Asp Pro Phe Thr Tyr Glu Asp Pro Asn Gln Ala
                595                 600                 605

Val Arg Glu Phe Ala Lys Glu Ile Asp Ala Ser Cys Ile Lys Ile Glu
        610                 615                 620

Lys Val Ile Gly Val Gly Glu Phe Gly Glu Val Cys Ser Gly Arg Leu
625                 630                 635                 640

Lys Val Pro Gly Lys Arg Glu Ile Cys Val Ala Ile Lys Thr Leu Lys
                645                 650                 655

Ala Gly Tyr Thr Asp Lys Gln Arg Arg Asp Phe Leu Ser Glu Ala Ser
                660                 665                 670

Ile Met Gly Gln Phe Asp His Pro Asn Ile Ile His Leu Glu Gly Val
                675                 680                 685

Val Thr Lys Cys Lys Pro Val Met Ile Ile Thr Glu Tyr Met Glu Asn
                690                 695                 700

Gly Ser Leu Asp Ala Phe Leu Arg Lys Asn Asp Gly Arg Phe Thr Val
705                 710                 715                 720

Ile Gln Leu Val Gly Met Leu Arg Gly Ile Gly Ser Gly Met Lys Tyr
                725                 730                 735
```

Leu Ser Asp Met Ser Tyr Val His Arg Asp Leu Ala Ala Arg Asn Ile
            740                 745                 750

Leu Val Asn Ser Asn Leu Val Cys Lys Val Ser Asp Phe Gly Met Ser
            755                 760                 765

Arg Val Leu Glu Asp Pro Glu Ala Ala Tyr Thr Thr Arg Gly Gly
        770                 775                 780

Lys Ile Pro Ile Arg Trp Thr Ala Pro Glu Ala Ile Ala Tyr Arg Lys
785                 790                 795                 800

Phe Thr Ser Ala Ser Asp Val Trp Ser Tyr Gly Ile Val Met Trp Glu
            805                 810                 815

Val Met Ser Tyr Gly Glu Arg Pro Tyr Trp Asp Met Ser Asn Gln Asp
            820                 825                 830

Val Ile Lys Ala Ile Glu Glu Gly Tyr Arg Leu Pro Pro Pro Met Asp
            835                 840                 845

Cys Pro Ile Ala Leu His Gln Leu Met Leu Asp Cys Trp Gln Lys Glu
            850                 855                 860

Arg Ser Asp Arg Pro Lys Phe Gly Gln Ile Val Asn Met Leu Asp Lys
865                 870                 875                 880

Leu Ile Arg Asn Pro Asn Ser Leu Lys Arg Thr Gly Ser Glu Ser Ser
            885                 890                 895

Arg Pro Asn Thr Ala Leu Leu Asp Pro Ser Pro Glu Phe Ser Ala
        900                 905                 910

Val Val Ser Val Gly Asp Trp Leu Gln Ala Ile Lys Met Asp Arg Tyr
            915                 920                 925

Lys Asp Asn Phe Thr Ala Ala Gly Tyr Thr Thr Leu Glu Ala Val Val
930                 935                 940

His Met Ser Gln Asp Asp Leu Ala Arg Ile Gly Ile Thr Ala Ile Thr
945                 950                 955                 960

His Gln Asn Lys Ile Leu Ser Ser Val Gln Ala Met Arg Thr Gln Met
            965                 970                 975

Gln Gln Met His Gly Arg Met Val Pro Val
            980                 985

<210> SEQ ID NO 2
<211> LENGTH: 528
<212> TYPE: PRT
<213> ORGANISM: Mus musculus

<400> SEQUENCE: 2

Val Thr Gly Ser Arg Val Tyr Pro Ala Asn Glu Val Thr Leu Leu Asp
1               5                   10                  15

Ser Arg Ser Val Gln Gly Glu Leu Gly Trp Ile Ala Ser Pro Leu Glu
            20                  25                  30

Gly Gly Trp Glu Glu Val Ser Ile Met Asp Glu Lys Asn Thr Pro Ile
        35                  40                  45

Arg Thr Tyr Gln Val Cys Asn Val Met Glu Ala Ser Gln Asn Asn Trp
    50                  55                  60

Leu Arg Thr Asp Trp Ile Thr Arg Glu Gly Ala Gln Arg Val Tyr Ile
65                  70                  75                  80

Glu Ile Lys Phe Thr Leu Arg Asp Cys Asn Ser Leu Pro Gly Val Met
            85                  90                  95

Gly Thr Cys Lys Glu Thr Phe Asn Leu Tyr Tyr Tyr Glu Ser Asp Asn
            100                 105                 110

Asp Lys Glu Arg Phe Ile Arg Glu Ser Gln Phe Gly Lys Ile Asp Thr

```
            115                 120                 125
Ile Ala Ala Asp Glu Ser Phe Thr Gln Val Asp Ile Gly Asp Arg Ile
130                 135                 140

Met Lys Leu Asn Thr Glu Ile Arg Asp Val Gly Pro Leu Ser Lys Lys
145                 150                 155                 160

Gly Phe Tyr Leu Ala Phe Gln Asp Val Gly Ala Cys Ile Ala Leu Val
                165                 170                 175

Ser Val Arg Val Phe Tyr Lys Lys Cys Pro Leu Thr Val Arg Asn Leu
            180                 185                 190

Ala Gln Phe Pro Asp Thr Ile Thr Gly Ala Asp Thr Ser Ser Leu Val
        195                 200                 205

Glu Val Arg Gly Ser Cys Val Asn Asn Ser Glu Glu Lys Asp Val Pro
    210                 215                 220

Lys Met Tyr Cys Gly Ala Asp Gly Glu Trp Leu Val Pro Ile Gly Asn
225                 230                 235                 240

Cys Leu Cys Asn Ala Gly His Glu Gln Asn Gly Glu Cys Gln Ala
                245                 250                 255

Cys Lys Ile Gly Tyr Tyr Lys Ala Leu Ser Thr Asp Ala Ser Cys Ala
                260                 265                 270

Lys Cys Pro Pro His Ser Tyr Ser Val Trp Glu Gly Ala Thr Ser Cys
            275                 280                 285

Thr Cys Asp Arg Gly Phe Phe Arg Ala Asp Asn Asp Ala Ala Ser Met
        290                 295                 300

Pro Cys Thr Arg Pro Ser Ala Pro Leu Asn Leu Ile Ser Asn Val
305                 310                 315                 320

Asn Glu Thr Ser Val Asn Leu Glu Trp Ser Ser Pro Gln Asn Thr Gly
                325                 330                 335

Gly Arg Gln Asp Ile Ser Tyr Asn Val Val Cys Lys Lys Cys Gly Ala
                340                 345                 350

Gly Asp Pro Ser Lys Cys Arg Pro Cys Gly Ser Gly Val His Tyr Thr
            355                 360                 365

Pro Gln Gln Asn Gly Leu Lys Thr Thr Arg Val Ser Ile Thr Asp Leu
        370                 375                 380

Leu Ala His Thr Asn Tyr Thr Phe Glu Ile Trp Ala Val Asn Gly Val
385                 390                 395                 400

Ser Lys Tyr Asn Pro Ser Pro Asp Gln Ser Val Ser Val Thr Val Thr
                405                 410                 415

Thr Asn Gln Ala Ala Pro Ser Ser Ile Ala Leu Val Gln Ala Lys Glu
                420                 425                 430

Val Thr Arg Tyr Ser Val Ala Leu Ala Trp Leu Glu Pro Asp Arg Pro
            435                 440                 445

Asn Gly Val Ile Leu Glu Tyr Glu Val Lys Tyr Tyr Glu Lys Asp Gln
        450                 455                 460

Asn Glu Arg Ser Tyr Arg Ile Val Arg Thr Ala Ala Arg Asn Thr Asp
465                 470                 475                 480

Ile Lys Gly Leu Asn Pro Leu Thr Ser Tyr Val Phe His Val Arg Ala
                485                 490                 495

Arg Thr Ala Ala Gly Tyr Gly Asp Phe Ser Glu Pro Leu Glu Val Thr
            500                 505                 510

Thr Asn Thr Val Pro Ser Arg Ile Ile Gly Asp Gly Ala Asn Ser Thr
        515                 520                 525

<210> SEQ ID NO 3
```

<211> LENGTH: 1030
<212> TYPE: PRT
<213> ORGANISM: Artificial Sequence
<220> FEATURE:
<223> OTHER INFORMATION: Synthetic polypeptide

<400> SEQUENCE: 3

Val Thr Gly Ser Arg Val Tyr Pro Ala Asn Glu Val Thr Leu Leu Asp
1               5                   10                  15

Ser Arg Ser Val Gln Gly Glu Leu Gly Trp Ile Ala Ser Pro Leu Glu
            20                  25                  30

Gly Gly Trp Glu Glu Val Ser Ile Met Asp Glu Lys Asn Thr Pro Ile
        35                  40                  45

Arg Thr Tyr Gln Val Cys Asn Val Met Glu Ala Ser Gln Asn Asn Trp
    50                  55                  60

Leu Arg Thr Asp Trp Ile Thr Arg Glu Gly Ala Gln Arg Val Tyr Ile
65                  70                  75                  80

Glu Ile Lys Phe Thr Leu Arg Asp Cys Asn Ser Leu Pro Gly Val Met
                85                  90                  95

Gly Thr Cys Lys Glu Thr Phe Asn Leu Tyr Tyr Glu Ser Asp Asn
            100                 105                 110

Asp Lys Glu Arg Phe Ile Arg Glu Ser Gln Phe Gly Lys Ile Asp Thr
        115                 120                 125

Ile Ala Ala Asp Glu Ser Phe Thr Gln Val Asp Ile Gly Asp Arg Ile
130                 135                 140

Met Lys Leu Asn Thr Glu Ile Arg Asp Val Gly Pro Leu Ser Lys Lys
145                 150                 155                 160

Gly Phe Tyr Leu Ala Phe Gln Asp Val Gly Ala Cys Ile Ala Leu Val
                165                 170                 175

Ser Val Arg Val Phe Tyr Lys Lys Cys Pro Leu Thr Val Arg Asn Leu
            180                 185                 190

Ala Gln Phe Pro Asp Thr Ile Thr Gly Ala Asp Thr Ser Ser Leu Val
        195                 200                 205

Glu Val Arg Gly Ser Cys Val Asn Asn Ser Glu Glu Lys Asp Val Pro
210                 215                 220

Lys Met Tyr Cys Gly Ala Asp Gly Glu Trp Leu Val Pro Ile Gly Asn
225                 230                 235                 240

Cys Leu Cys Asn Ala Gly His Glu Glu Gln Asn Gly Glu Cys Gln Ala
                245                 250                 255

Cys Lys Ile Gly Tyr Tyr Lys Ala Leu Ser Thr Asp Ala Ser Cys Ala
            260                 265                 270

Lys Cys Pro Pro His Ser Tyr Ser Val Trp Glu Gly Ala Thr Ser Cys
        275                 280                 285

Thr Cys Asp Arg Gly Phe Phe Arg Ala Asp Asn Asp Ala Ala Ser Met
290                 295                 300

Pro Cys Thr Arg Pro Pro Ser Ala Pro Leu Asn Leu Ile Ser Asn Val
305                 310                 315                 320

Asn Glu Thr Ser Val Asn Leu Glu Trp Ser Ser Pro Gln Asn Thr Gly
                325                 330                 335

Gly Arg Gln Asp Ile Ser Tyr Asn Val Val Cys Lys Lys Cys Gly Ala
            340                 345                 350

Gly Asp Pro Ser Lys Cys Arg Pro Cys Gly Ser Gly Val His Tyr Thr
        355                 360                 365

Pro Gln Gln Asn Gly Leu Lys Thr Thr Arg Val Ser Ile Thr Asp Leu
370                 375                 380

-continued

```
Leu Ala His Thr Asn Tyr Thr Phe Glu Ile Trp Ala Val Asn Gly Val
385                 390                 395                 400

Ser Lys Tyr Asn Pro Ser Pro Asp Gln Ser Val Ser Val Thr Val Thr
            405                 410                 415

Thr Asn Gln Ala Ala Pro Ser Ser Ile Ala Leu Val Gln Ala Lys Glu
                420                 425                 430

Val Thr Arg Tyr Ser Val Ala Leu Ala Trp Leu Glu Pro Asp Arg Pro
        435                 440                 445

Asn Gly Val Ile Leu Glu Tyr Glu Val Lys Tyr Tyr Glu Lys Asp Gln
    450                 455                 460

Asn Glu Arg Ser Tyr Arg Ile Val Arg Thr Ala Ala Arg Asn Thr Asp
465                 470                 475                 480

Ile Lys Gly Leu Asn Pro Leu Thr Ser Tyr Val Phe His Val Arg Ala
                485                 490                 495

Arg Thr Ala Ala Gly Tyr Gly Asp Phe Ser Glu Pro Leu Glu Val Thr
        500                 505                 510

Thr Asn Thr Val Pro Ser Arg Ile Ile Gly Asp Gly Ala Asn Ser Thr
    515                 520                 525

Ala Ala Ile Ile Pro Val Glu Glu Glu Asn Pro Asp Phe Trp Asn
530                 535                 540

Arg Glu Ala Ala Glu Ala Leu Gly Ala Ala Lys Lys Leu Gln Pro Ala
545                 550                 555                 560

Gln Thr Ala Ala Lys Asn Leu Ile Ile Phe Leu Gly Asp Gly Met Gly
                565                 570                 575

Val Ser Thr Val Thr Ala Ala Arg Ile Leu Lys Gly Gln Lys Lys Asp
        580                 585                 590

Lys Leu Gly Pro Glu Ile Pro Leu Ala Met Asp Arg Phe Pro Tyr Val
    595                 600                 605

Ala Leu Ser Lys Thr Tyr Asn Val Asp Lys His Val Pro Asp Ser Gly
            610                 615                 620

Ala Thr Ala Thr Ala Tyr Leu Cys Gly Val Lys Gly Asn Phe Gln Thr
625                 630                 635                 640

Ile Gly Leu Ser Ala Ala Arg Phe Asn Gln Cys Asn Thr Thr Arg
                645                 650                 655

Gly Asn Glu Val Ile Ser Val Met Asn Arg Ala Lys Lys Ala Gly Lys
            660                 665                 670

Ser Val Gly Val Val Thr Thr Thr Arg Val Gln His Ala Ser Pro Ala
        675                 680                 685

Gly Thr Tyr Ala His Thr Val Asn Arg Asn Trp Tyr Ser Asp Ala Asp
    690                 695                 700

Val Pro Ala Ser Ala Arg Gln Glu Gly Cys Gln Asp Ile Ala Thr Gln
705                 710                 715                 720

Leu Ile Ser Asn Met Asp Ile Asp Val Ile Leu Gly Gly Gly Arg Lys
                725                 730                 735

Tyr Met Phe Arg Met Gly Thr Pro Asp Pro Glu Tyr Pro Asp Asp Tyr
            740                 745                 750

Ser Gln Gly Gly Thr Arg Leu Asp Gly Lys Asn Leu Val Gln Glu Trp
        755                 760                 765

Leu Ala Lys Arg Gln Gly Ala Arg Tyr Val Trp Asn Arg Thr Glu Leu
    770                 775                 780

Met Gln Ala Ser Leu Asp Pro Ser Val Thr His Leu Met Gly Leu Phe
785                 790                 795                 800
```

-continued

```
Glu Pro Gly Asp Met Lys Tyr Glu Ile His Arg Asp Ser Thr Leu Asp
            805                 810                 815

Pro Ser Leu Met Glu Met Thr Glu Ala Ala Leu Arg Leu Leu Ser Arg
        820                 825                 830

Asn Pro Arg Gly Phe Phe Leu Phe Val Glu Gly Gly Arg Ile Asp His
    835                 840                 845

Gly His His Glu Ser Arg Ala Tyr Arg Ala Leu Thr Glu Thr Ile Met
850                 855                 860

Phe Asp Asp Ala Ile Glu Arg Ala Gly Gln Leu Thr Ser Glu Glu Asp
865                 870                 875                 880

Thr Leu Ser Leu Val Thr Ala Asp His Ser His Val Phe Ser Phe Gly
                885                 890                 895

Gly Tyr Pro Leu Arg Gly Ser Ser Ile Phe Gly Leu Ala Pro Gly Lys
            900                 905                 910

Ala Arg Asp Arg Lys Ala Tyr Thr Val Leu Leu Tyr Gly Asn Gly Pro
        915                 920                 925

Gly Tyr Val Leu Lys Asp Gly Ala Arg Pro Asp Val Thr Glu Ser Glu
    930                 935                 940

Ser Gly Ser Pro Glu Tyr Arg Gln Gln Ser Ala Val Pro Leu Asp Glu
945                 950                 955                 960

Glu Thr His Ala Gly Glu Asp Val Ala Val Phe Ala Arg Gly Pro Gln
                965                 970                 975

Ala His Leu Val His Gly Val Gln Glu Gln Thr Phe Ile Ala His Val
            980                 985                 990

Met Ala Phe Ala Ala Cys Leu Glu  Pro Tyr Thr Ala Cys  Asp Leu Ala
        995                 1000                1005

Pro Pro  Ala Gly Thr Thr Asp  Ala Ala His Pro Gly  His His His
    1010                1015                1020

His His  His His His His His
    1025                1030

<210> SEQ ID NO 4
<211> LENGTH: 19
<212> TYPE: PRT
<213> ORGANISM: Mus musculus

<400> SEQUENCE: 4

Met Ala Gly Ile Phe Tyr Phe Ile Leu Phe Ser Phe Leu Phe Gly Ile
1               5                   10                  15

Cys Asp Ala

<210> SEQ ID NO 5
<211> LENGTH: 986
<212> TYPE: PRT
<213> ORGANISM: Homo sapiens

<400> SEQUENCE: 5

Met Ala Gly Ile Phe Tyr Phe Ala Leu Phe Ser Cys Leu Phe Gly Ile
1               5                   10                  15

Cys Asp Ala Val Thr Gly Ser Arg Val Tyr Pro Ala Asn Glu Val Thr
            20                  25                  30

Leu Leu Asp Ser Arg Ser Val Gln Gly Glu Leu Gly Trp Ile Ala Ser
        35                  40                  45

Pro Leu Glu Gly Gly Trp Glu Glu Val Ser Ile Met Asp Glu Lys Asn
    50                  55                  60

Thr Pro Ile Arg Thr Tyr Gln Val Cys Asn Val Met Glu Pro Ser Gln
```

```
            65                  70                  75                  80
Asn Asn Trp Leu Arg Thr Asp Trp Ile Thr Arg Glu Gly Ala Gln Arg
                85                  90                  95

Val Tyr Ile Glu Ile Lys Phe Thr Leu Arg Asp Cys Asn Ser Leu Pro
                100                 105                 110

Gly Val Met Gly Thr Cys Lys Glu Thr Phe Asn Leu Tyr Tyr Tyr Glu
                115                 120                 125

Ser Asp Asn Asp Lys Glu Arg Phe Ile Arg Glu Asn Gln Phe Val Lys
                130                 135                 140

Ile Asp Thr Ile Ala Ala Asp Glu Ser Phe Thr Gln Val Asp Ile Gly
145                 150                 155                 160

Asp Arg Ile Met Lys Leu Asn Thr Glu Ile Arg Asp Val Gly Pro Leu
                165                 170                 175

Ser Lys Lys Gly Phe Tyr Leu Ala Phe Gln Asp Val Gly Ala Cys Ile
                180                 185                 190

Ala Leu Val Ser Val Arg Val Phe Tyr Lys Lys Cys Pro Leu Thr Val
                195                 200                 205

Arg Asn Leu Ala Gln Phe Pro Asp Thr Ile Thr Gly Ala Asp Thr Ser
210                 215                 220

Ser Leu Val Glu Val Arg Gly Ser Cys Val Asn Asn Ser Glu Glu Lys
225                 230                 235                 240

Asp Val Pro Lys Met Tyr Cys Gly Ala Asp Gly Glu Trp Leu Val Pro
                245                 250                 255

Ile Gly Asn Cys Leu Cys Asn Ala Gly His Glu Glu Arg Ser Gly Glu
                260                 265                 270

Cys Gln Ala Cys Lys Ile Gly Tyr Tyr Lys Ala Leu Ser Thr Asp Ala
                275                 280                 285

Thr Cys Ala Lys Cys Pro Pro His Ser Tyr Ser Val Trp Glu Gly Ala
                290                 295                 300

Thr Ser Cys Thr Cys Asp Arg Gly Phe Phe Arg Ala Asp Asn Asp Ala
305                 310                 315                 320

Ala Ser Met Pro Cys Thr Arg Pro Pro Ser Ala Pro Leu Asn Leu Ile
                325                 330                 335

Ser Asn Val Asn Glu Thr Ser Val Asn Leu Glu Trp Ser Ser Pro Gln
                340                 345                 350

Asn Thr Gly Gly Arg Gln Asp Ile Ser Tyr Asn Val Val Cys Lys Lys
                355                 360                 365

Cys Gly Ala Gly Asp Pro Ser Lys Cys Arg Pro Cys Gly Ser Gly Val
                370                 375                 380

His Tyr Thr Pro Gln Gln Asn Gly Leu Lys Thr Thr Lys Val Ser Ile
385                 390                 395                 400

Thr Asp Leu Leu Ala His Thr Asn Tyr Thr Phe Glu Ile Trp Ala Val
                405                 410                 415

Asn Gly Val Ser Lys Tyr Asn Pro Asn Pro Asp Gln Ser Val Ser Val
                420                 425                 430

Thr Val Thr Thr Asn Gln Ala Ala Pro Ser Ser Ile Ala Leu Val Gln
                435                 440                 445

Ala Lys Glu Val Thr Arg Tyr Ser Val Ala Leu Ala Trp Leu Glu Pro
                450                 455                 460

Asp Arg Pro Asn Gly Val Ile Leu Glu Tyr Glu Val Lys Tyr Tyr Glu
465                 470                 475                 480

Lys Asp Gln Asn Glu Arg Ser Tyr Arg Ile Val Arg Thr Ala Ala Arg
                485                 490                 495
```

-continued

```
Asn Thr Asp Ile Lys Gly Leu Asn Pro Leu Thr Ser Tyr Val Phe His
            500                 505                 510
Val Arg Ala Arg Thr Ala Ala Gly Tyr Gly Asp Phe Ser Glu Pro Leu
            515                 520                 525
Glu Val Thr Thr Asn Thr Val Pro Ser Arg Ile Ile Gly Asp Gly Ala
            530                 535                 540
Asn Ser Thr Val Leu Leu Val Ser Val Ser Gly Ser Val Val Leu Val
545                 550                 555                 560
Val Ile Leu Ile Ala Ala Phe Val Ile Ser Arg Arg Ser Lys Tyr
                565                 570                 575
Ser Lys Ala Lys Gln Glu Ala Asp Glu Lys His Leu Asn Gln Gly
            580                 585                 590
Val Arg Thr Tyr Val Asp Pro Phe Thr Tyr Glu Asp Pro Asn Gln Ala
            595                 600                 605
Val Arg Glu Phe Ala Lys Glu Ile Asp Ala Ser Cys Ile Lys Ile Glu
            610                 615                 620
Lys Val Ile Gly Val Gly Glu Phe Gly Glu Val Cys Ser Gly Arg Leu
625                 630                 635                 640
Lys Val Pro Gly Lys Arg Glu Ile Cys Val Ala Ile Lys Thr Leu Lys
            645                 650                 655
Ala Gly Tyr Thr Asp Lys Gln Arg Arg Asp Phe Leu Ser Glu Ala Ser
            660                 665                 670
Ile Met Gly Gln Phe Asp His Pro Asn Ile Ile His Leu Glu Gly Val
            675                 680                 685
Val Thr Lys Cys Lys Pro Val Met Ile Ile Thr Glu Tyr Met Glu Asn
            690                 695                 700
Gly Ser Leu Asp Ala Phe Leu Arg Lys Asn Asp Gly Arg Phe Thr Val
705                 710                 715                 720
Ile Gln Leu Val Gly Met Leu Arg Gly Ile Gly Ser Gly Met Lys Tyr
            725                 730                 735
Leu Ser Asp Met Ser Tyr Val His Arg Asp Leu Ala Ala Arg Asn Ile
            740                 745                 750
Leu Val Asn Ser Asn Leu Val Cys Lys Val Ser Asp Phe Gly Met Ser
            755                 760                 765
Arg Val Leu Glu Asp Asp Pro Glu Ala Ala Tyr Thr Thr Arg Gly Gly
            770                 775                 780
Lys Ile Pro Ile Arg Trp Thr Ala Pro Glu Ala Ile Ala Tyr Arg Lys
785                 790                 795                 800
Phe Thr Ser Ala Ser Asp Val Trp Ser Tyr Gly Ile Val Met Trp Glu
                805                 810                 815
Val Met Ser Tyr Gly Glu Arg Pro Tyr Trp Asp Met Ser Asn Gln Asp
            820                 825                 830
Val Ile Lys Ala Ile Glu Glu Gly Tyr Arg Leu Pro Pro Pro Met Asp
            835                 840                 845
Cys Pro Ile Ala Leu His Gln Leu Met Leu Asp Cys Trp Gln Lys Glu
            850                 855                 860
Arg Ser Asp Arg Pro Lys Phe Gly Gln Ile Val Asn Met Leu Asp Lys
865                 870                 875                 880
Leu Ile Arg Asn Pro Asn Ser Leu Lys Arg Thr Gly Thr Glu Ser Ser
                885                 890                 895
Arg Pro Asn Thr Ala Leu Leu Asp Pro Ser Ser Pro Glu Phe Ser Ala
            900                 905                 910
```

-continued

```
Val Val Ser Val Gly Asp Trp Leu Gln Ala Ile Lys Met Asp Arg Tyr
            915                 920                 925

Lys Asp Asn Phe Thr Ala Ala Gly Tyr Thr Thr Leu Glu Ala Val Val
        930                 935                 940

His Val Asn Gln Glu Asp Leu Ala Arg Ile Gly Ile Thr Ala Ile Thr
945                 950                 955                 960

His Gln Asn Lys Ile Leu Ser Ser Val Gln Ala Met Arg Thr Gln Met
                965                 970                 975

Gln Gln Met His Gly Arg Met Val Pro Val
            980                 985

<210> SEQ ID NO 6
<211> LENGTH: 528
<212> TYPE: PRT
<213> ORGANISM: Homo sapiens

<400> SEQUENCE: 6

Val Thr Gly Ser Arg Val Tyr Pro Ala Asn Glu Val Thr Leu Leu Asp
1               5                   10                  15

Ser Arg Ser Val Gln Gly Glu Leu Gly Trp Ile Ala Ser Pro Leu Glu
            20                  25                  30

Gly Gly Trp Glu Glu Val Ser Ile Met Asp Glu Lys Asn Thr Pro Ile
        35                  40                  45

Arg Thr Tyr Gln Val Cys Asn Val Met Glu Pro Ser Gln Asn Asn Trp
    50                  55                  60

Leu Arg Thr Asp Trp Ile Thr Arg Glu Gly Ala Gln Arg Val Tyr Ile
65                  70                  75                  80

Glu Ile Lys Phe Thr Leu Arg Asp Cys Asn Ser Leu Pro Gly Val Met
                85                  90                  95

Gly Thr Cys Lys Glu Thr Phe Asn Leu Tyr Tyr Tyr Glu Ser Asp Asn
            100                 105                 110

Asp Lys Glu Arg Phe Ile Arg Glu Asn Gln Phe Val Lys Ile Asp Thr
        115                 120                 125

Ile Ala Ala Asp Glu Ser Phe Thr Gln Val Asp Ile Gly Asp Arg Ile
    130                 135                 140

Met Lys Leu Asn Thr Glu Ile Arg Asp Val Gly Pro Leu Ser Lys Lys
145                 150                 155                 160

Gly Phe Tyr Leu Ala Phe Gln Asp Val Gly Ala Cys Ile Ala Leu Val
                165                 170                 175

Ser Val Arg Val Phe Tyr Lys Lys Cys Pro Leu Thr Val Arg Asn Leu
            180                 185                 190

Ala Gln Phe Pro Asp Thr Ile Thr Gly Ala Asp Thr Ser Ser Leu Val
        195                 200                 205

Glu Val Arg Gly Ser Cys Val Asn Asn Ser Glu Glu Lys Asp Val Pro
    210                 215                 220

Lys Met Tyr Cys Gly Ala Asp Gly Glu Trp Leu Val Pro Ile Gly Asn
225                 230                 235                 240

Cys Leu Cys Asn Ala Gly His Glu Glu Arg Ser Gly Glu Cys Gln Ala
                245                 250                 255

Cys Lys Ile Gly Tyr Tyr Lys Ala Leu Ser Thr Asp Ala Thr Cys Ala
            260                 265                 270

Lys Cys Pro Pro His Ser Tyr Ser Val Trp Glu Gly Ala Thr Ser Cys
        275                 280                 285

Thr Cys Asp Arg Gly Phe Phe Arg Ala Asp Asn Asp Ala Ala Ser Met
    290                 295                 300
```

Pro Cys Thr Arg Pro Pro Ser Ala Pro Leu Asn Leu Ile Ser Asn Val
305                 310                 315                 320

Asn Glu Thr Ser Val Asn Leu Glu Trp Ser Ser Pro Gln Asn Thr Gly
            325                 330                 335

Gly Arg Gln Asp Ile Ser Tyr Asn Val Val Cys Lys Lys Cys Gly Ala
        340                 345                 350

Gly Asp Pro Ser Lys Cys Arg Pro Cys Gly Ser Gly Val His Tyr Thr
    355                 360                 365

Pro Gln Gln Asn Gly Leu Lys Thr Thr Lys Val Ser Ile Thr Asp Leu
370                 375                 380

Leu Ala His Thr Asn Tyr Thr Phe Glu Ile Trp Ala Val Asn Gly Val
385                 390                 395                 400

Ser Lys Tyr Asn Pro Asn Pro Asp Gln Ser Val Ser Val Thr Val Thr
            405                 410                 415

Thr Asn Gln Ala Ala Pro Ser Ser Ile Ala Leu Val Gln Ala Lys Glu
        420                 425                 430

Val Thr Arg Tyr Ser Val Ala Leu Ala Trp Leu Glu Pro Asp Arg Pro
    435                 440                 445

Asn Gly Val Ile Leu Glu Tyr Glu Val Lys Tyr Tyr Glu Lys Asp Gln
450                 455                 460

Asn Glu Arg Ser Tyr Arg Ile Val Arg Thr Ala Ala Arg Asn Thr Asp
465                 470                 475                 480

Ile Lys Gly Leu Asn Pro Leu Thr Ser Tyr Val Phe His Val Arg Ala
            485                 490                 495

Arg Thr Ala Ala Gly Tyr Gly Asp Phe Ser Glu Pro Leu Glu Val Thr
        500                 505                 510

Thr Asn Thr Val Pro Ser Arg Ile Ile Gly Asp Gly Ala Asn Ser Thr
    515                 520                 525

<210> SEQ ID NO 7
<211> LENGTH: 12
<212> TYPE: DNA
<213> ORGANISM: Artificial Sequence
<220> FEATURE:
<223> OTHER INFORMATION: ad29S

<400> SEQUENCE: 7
acatcactcc gt                                                       12

<210> SEQ ID NO 8
<211> LENGTH: 50
<212> TYPE: DNA
<213> ORGANISM: Artificial Sequence
<220> FEATURE:
<223> OTHER INFORMATION: ad29AS

<400> SEQUENCE: 8
acggagtgat gtccgtcgac gtatctctgc gttgatactt cagcgtagct              50

<210> SEQ ID NO 9
<211> LENGTH: 26
<212> TYPE: DNA
<213> ORGANISM: Artificial Sequence
<220> FEATURE:
<223> OTHER INFORMATION: Synthetic primer

<400> SEQUENCE: 9
agctacgctg aagtatcaac gcagag                                        26

```
<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
gccagtggat agactgatgg                                              20

<210> SEQ ID NO 11
<211> LENGTH: 21
<212> TYPE: DNA
<213> ORGANISM: Artificial Sequence
<220> FEATURE:
<223> OTHER INFORMATION: Synthetic primer

<400> SEQUENCE: 11
gatggataca gttggtgcag c                                            21

<210> SEQ ID NO 12
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 12

Met Ala Val Leu Val Leu Leu Leu Cys Leu Val Thr Phe Pro Ser Cys
1               5                   10                  15

Val Leu Ser

<210> SEQ ID NO 13
<211> LENGTH: 125
<212> TYPE: PRT
<213> ORGANISM: Artificial Sequence
<220> FEATURE:
<223> OTHER INFORMATION: Synthetic polypeptide

<400> SEQUENCE: 13

Gln Val Gln Leu Lys Gln Ser Gly Pro Ser Leu Val Gln Pro Ser Gln
1               5                   10                  15

Ser Leu Ser Ile Thr Cys Thr Val Ser Gly Phe Ser Leu Thr Arg Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Asn Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Lys Glu Ser Leu Phe Gly Val Tyr Tyr Asp Tyr Gly Tyr Tyr Ser Met
            100                 105                 110

Asp Tyr Trp Gly Gln Gly Thr Ser Val Thr Val Ser Ser
        115                 120                 125

<210> SEQ ID NO 14
<211> LENGTH: 22
<212> TYPE: PRT
<213> ORGANISM: Artificial Sequence
<220> FEATURE:
```

<223> OTHER INFORMATION: Synthetic polypeptide

<400> SEQUENCE: 14

Met Asp Met Arg Val Pro Ala His Val Phe Gly Phe Leu Leu Leu Trp
1               5                   10                  15

Phe Pro Gly Thr Arg Cys
            20

<210> SEQ ID NO 15
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 15

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Leu
                85                  90                  95

Thr Phe Gly Ala Gly Thr Lys Leu Glu Leu Lys
            100                 105

<210> SEQ ID NO 16
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 16
atggctgtcc tggtgctgct cctctgcctg gtgacattcc caagctgtgt cctgtcc        57

<210> SEQ ID NO 17
<211> LENGTH: 375
<212> TYPE: DNA
<213> ORGANISM: Artificial Sequence
<220> FEATURE:
<223> OTHER INFORMATION: Synthetic polynucleotide

<400> SEQUENCE: 17
caggtgcagc tgaagcagtc aggacctagc ctagtgcagc cctcacagag cctgtccata      60
acctgcacag tctctggttt ctcattaact aggtatggtg tacactgggt tcgccagtct     120
ccaggaaagg gtctggagtg gctgggagtg atttggagag gtggaagcac agactacaat     180
gcagctttca tgtccagact gagcatcacc aaggacaact ccaagagcca agttttcttt     240
aaaatgaaca gtctgcaagc tgatgacact gccatatact actgtgccaa gaaaagccta     300
tttggggtct actatgatta cgggtactat tctatggact actggggtca aggaacctca     360
gtcaccgtct cctca                                                     375

<210> SEQ ID NO 18

<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 18

```
atggacatga gggttcctgc tcacgttttt ggcttcttgt tgctctggtt tccaggtacc    60
agatgt                                                               66
```

<210> SEQ ID NO 19
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 19

```
gacatccaaa tgacccagtc tccatcctcc ttatctgcct ctctgggaga aagagtcagt    60
ctcacttgtc gggcaagtca ggaaattagt ggttacttaa gctggcttca gcagaaacca   120
gatggaacta ttaaacgcct gatctacgcc gcatccactt tagattctgg tgtcccaaaa   180
aggttcagtg gcagtaggtc tgggtcagat tattctctca ccatcagcag ccttgagtct   240
gaagattttg cagactatta ctgtctacaa tatgctagtt atccgctcac gttcggtgct   300
gggaccaagc tggagctgaa a                                              321
```

<210> SEQ ID NO 20
<211> LENGTH: 40
<212> TYPE: DNA
<213> ORGANISM: Artificial Sequence
<220> FEATURE:
<223> OTHER INFORMATION: Synthetic primer

<400> SEQUENCE: 20

```
gcgaagcttg ccgccaccat ggctgtcctg gtgctgctcc                          40
```

<210> SEQ ID NO 21
<211> LENGTH: 43
<212> TYPE: DNA
<213> ORGANISM: Artificial Sequence
<220> FEATURE:
<223> OTHER INFORMATION: Synthetic primer

<400> SEQUENCE: 21

```
gcgaagcttg ccgccaccat ggacatgagg gttcctgctc acg                      43
```

<210> SEQ ID NO 22
<211> LENGTH: 36
<212> TYPE: DNA
<213> ORGANISM: Artificial Sequence
<220> FEATURE:
<223> OTHER INFORMATION: Synthetic primer

<400> SEQUENCE: 22

```
gcggaattca tcatttacca ggagagtggg agaggc                              36
```

<210> SEQ ID NO 23
<211> LENGTH: 40
<212> TYPE: DNA
<213> ORGANISM: Artificial Sequence
<220> FEATURE:
<223> OTHER INFORMATION: Synthetic primer

<400> SEQUENCE: 23

```
cgcgaattca ctaacactca ttcctgttga agctcttgac                              40
```

<210> SEQ ID NO 24
<211> LENGTH: 324
<212> TYPE: PRT
<213> ORGANISM: Artificial Sequence
<220> FEATURE:
<223> OTHER INFORMATION: Synthetic polypeptide

<400> SEQUENCE: 24

```
Ala Lys Thr Thr Pro Pro Ser Val Tyr Pro Leu Ala Pro Gly Ser Ala
 1               5                  10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
           100                 105                 110

Glu Val Ser Ser Val Phe Ile Phe Pro Pro Lys Pro Lys Asp Val Leu
       115                 120                 125

Thr Ile Thr Leu Thr Pro Lys Val Thr Cys Val Val Val Asp Ile Ser
   130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys
```

<210> SEQ ID NO 25
<211> LENGTH: 107
<212> TYPE: PRT

<213> ORGANISM: Artificial Sequence
<220> FEATURE:
<223> OTHER INFORMATION: Synthetic polypeptide

<400> SEQUENCE: 25

Arg Ala Asp Ala Ala Pro Thr Val Ser Ile Phe Pro Pro Ser Ser Glu
1               5                   10                  15
Gln Leu Thr Ser Gly Gly Ala Ser Val Val Cys Phe Leu Asn Asn Phe
            20                  25                  30
Tyr Pro Lys Asp Ile Asn Val Lys Trp Lys Ile Asp Gly Ser Glu Arg
        35                  40                  45
Gln Asn Gly Val Leu Asn Ser Trp Thr Asp Gln Asp Ser Lys Asp Ser
    50                  55                  60
Thr Tyr Ser Met Ser Ser Thr Leu Thr Leu Lys Asp Glu Tyr Glu
65                  70                  75                  80
Arg His Asn Ser Tyr Thr Cys Glu Ala Thr His Lys Thr Ser Thr Ser
                85                  90                  95
Pro Ile Val Lys Ser Phe Asn Arg Asn Glu Cys
            100                 105

<210> SEQ ID NO 26
<211> LENGTH: 5
<212> TYPE: PRT
<213> ORGANISM: Artificial Sequence
<220> FEATURE:
<223> OTHER INFORMATION: Synthetic peptide

<400> SEQUENCE: 26

Arg Tyr Gly Val His
1               5

<210> SEQ ID NO 27
<211> LENGTH: 16
<212> TYPE: PRT
<213> ORGANISM: Artificial Sequence
<220> FEATURE:
<223> OTHER INFORMATION: Synthetic peptide

<400> SEQUENCE: 27

Val Ile Trp Arg Gly Gly Ser Thr Asp Tyr Asn Ala Ala Phe Met Ser
1               5                   10                  15

<210> SEQ ID NO 28
<211> LENGTH: 17
<212> TYPE: PRT
<213> ORGANISM: Artificial Sequence
<220> FEATURE:
<223> OTHER INFORMATION: Synthetic peptide

<400> SEQUENCE: 28

Glu Ser Leu Phe Gly Val Tyr Tyr Asp Tyr Gly Tyr Tyr Ser Met Asp
1               5                   10                  15
Tyr

<210> SEQ ID NO 29
<211> LENGTH: 11
<212> TYPE: PRT
<213> ORGANISM: Artificial Sequence
<220> FEATURE:
<223> OTHER INFORMATION: Synthetic peptide

<400> SEQUENCE: 29

Arg Ala Ser Gln Glu Ile Ser Gly Tyr Leu Ser

<210> SEQ ID NO 30
<211> LENGTH: 7
<212> TYPE: PRT
<213> ORGANISM: Artificial Sequence
<220> FEATURE:
<223> OTHER INFORMATION: Synthetic peptide

<400> SEQUENCE: 30

Ala Ala Ser Thr Leu Asp Ser
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic peptide

<400> SEQUENCE: 31

Leu Gln Tyr Ala Ser Tyr Pro Leu Thr
1               5

<210> SEQ ID NO 32
<211> LENGTH: 986
<212> TYPE: PRT
<213> ORGANISM: Macaca mulatta

<400> SEQUENCE: 32

Met Ala Gly Ile Phe Tyr Phe Ala Leu Phe Ser Cys Leu Phe Gly Ile
1               5                   10                  15

Cys Asp Ala Val Thr Gly Ser Arg Val Tyr Pro Ala Asn Glu Val Thr
            20                  25                  30

Leu Leu Asp Ser Arg Ser Val Gln Gly Glu Leu Gly Trp Ile Ala Ser
        35                  40                  45

Pro Leu Glu Gly Gly Trp Glu Glu Val Ser Ile Met Asp Glu Lys Asn
    50                  55                  60

Thr Pro Ile Arg Thr Tyr Gln Val Cys Asn Val Met Glu Pro Ser Gln
65                  70                  75                  80

Asn Asn Trp Leu Arg Thr Asp Trp Ile Thr Arg Glu Gly Ala Gln Arg
                85                  90                  95

Val Tyr Ile Glu Ile Lys Phe Thr Leu Arg Asp Cys Asn Ser Leu Pro
            100                 105                 110

Gly Val Met Gly Thr Cys Lys Glu Thr Phe Asn Leu Tyr Tyr Tyr Glu
        115                 120                 125

Ser Asp Asn Asp Lys Glu Arg Phe Ile Arg Glu Asn Gln Phe Val Lys
    130                 135                 140

Ile Asp Thr Ile Ala Ala Asp Glu Ser Phe Thr Gln Val Asp Ile Gly
145                 150                 155                 160

Asp Arg Ile Met Lys Leu Asn Thr Glu Ile Arg Asp Val Gly Pro Leu
                165                 170                 175

Ser Lys Lys Gly Phe Tyr Leu Ala Phe Gln Asp Val Gly Ala Cys Ile
            180                 185                 190

Ala Leu Val Ser Val Arg Val Phe Tyr Lys Lys Cys Pro Leu Thr Val
        195                 200                 205

Arg Asn Leu Ala Gln Phe Pro Asp Thr Ile Thr Gly Ala Asp Thr Ser
    210                 215                 220

Ser Leu Val Glu Val Arg Gly Ser Cys Val Asn Asn Ser Glu Glu Lys

```
                225                 230                 235                 240
Asp Val Pro Lys Met Tyr Cys Gly Ala Asp Gly Glu Trp Leu Val Pro
                    245                 250                 255

Ile Gly Asn Cys Leu Cys Asn Ala Gly His Glu Glu Arg Ser Gly Glu
                    260                 265                 270

Cys Gln Ala Cys Lys Ile Gly Tyr Tyr Lys Ala Leu Ser Thr Asp Ala
                    275                 280                 285

Thr Cys Ala Lys Cys Pro Pro His Ser Tyr Ser Val Trp Glu Gly Ala
                290                 295                 300

Thr Ser Cys Thr Cys Asp Arg Gly Phe Phe Arg Ala Asp Asn Asp Ala
305                 310                 315                 320

Ala Ser Met Pro Cys Thr Arg Pro Pro Ser Ala Pro Leu Asn Leu Ile
                    325                 330                 335

Ser Asn Val Asn Glu Thr Ser Val Asn Leu Glu Trp Ser Ser Pro Gln
                    340                 345                 350

Asn Thr Gly Gly Arg Gln Asp Ile Ser Tyr Asn Val Val Cys Lys Lys
                    355                 360                 365

Cys Gly Ala Gly Asp Pro Ser Lys Cys Arg Pro Cys Gly Ser Gly Val
                    370                 375                 380

His Tyr Thr Pro Gln Gln Asn Gly Leu Lys Thr Thr Lys Val Ser Ile
385                 390                 395                 400

Thr Asp Leu Leu Ala His Thr Asn Tyr Thr Phe Glu Ile Trp Ala Val
                    405                 410                 415

Asn Gly Val Ser Lys Tyr Asn Pro Ser Pro Asp Gln Ser Val Ser Val
                    420                 425                 430

Thr Val Thr Thr Asn Gln Ala Ala Pro Ser Ser Ile Ala Leu Val Gln
                    435                 440                 445

Ala Lys Glu Val Thr Arg Tyr Ser Val Ala Leu Ala Trp Leu Glu Pro
                450                 455                 460

Asp Arg Pro Asn Gly Val Ile Leu Glu Tyr Glu Val Lys Tyr Tyr Glu
465                 470                 475                 480

Lys Asp Gln Asn Glu Arg Ser Tyr Arg Ile Val Arg Thr Ala Ala Arg
                    485                 490                 495

Asn Thr Asp Ile Lys Gly Leu Asn Pro Leu Thr Ser Tyr Val Phe His
                    500                 505                 510

Val Arg Ala Arg Thr Ala Ala Gly Tyr Gly Asp Phe Ser Glu Pro Leu
                    515                 520                 525

Glu Val Thr Thr Asn Thr Val Pro Ser Arg Ile Ile Gly Asp Gly Ala
                530                 535                 540

Asn Ser Thr Val Leu Leu Val Ser Val Ser Gly Ser Val Val Leu Val
545                 550                 555                 560

Val Ile Leu Ile Ala Ala Phe Val Ile Ser Arg Arg Arg Ser Lys Tyr
                    565                 570                 575

Ser Lys Ala Lys Gln Glu Ala Asp Glu Glu Lys His Leu Asn Gln Gly
                580                 585                 590

Val Arg Thr Tyr Val Asp Pro Phe Thr Tyr Glu Asp Pro Asn Gln Ala
                    595                 600                 605

Val Arg Glu Phe Ala Lys Glu Ile Asp Ala Ser Cys Ile Lys Ile Glu
                    610                 615                 620

Lys Val Ile Gly Val Gly Glu Phe Gly Glu Val Cys Ser Gly Arg Leu
625                 630                 635                 640

Lys Val Pro Gly Lys Arg Glu Ile Cys Val Ala Ile Lys Thr Leu Lys
                    645                 650                 655
```

Ala Gly Tyr Thr Asp Lys Gln Arg Arg Asp Phe Leu Ser Glu Ala Ser
            660                 665                 670

Ile Met Gly Gln Phe Asp His Pro Asn Ile Ile His Leu Glu Gly Val
        675                 680                 685

Val Thr Lys Cys Lys Pro Val Met Ile Ile Thr Glu Tyr Met Glu Asn
    690                 695                 700

Gly Ser Leu Asp Ala Phe Leu Arg Lys Asn Asp Gly Arg Phe Thr Val
705                 710                 715                 720

Ile Gln Leu Val Gly Met Leu Arg Gly Ile Gly Ser Gly Met Lys Tyr
                725                 730                 735

Leu Ser Asp Met Ser Tyr Val His Arg Asp Leu Ala Ala Arg Asn Ile
            740                 745                 750

Leu Val Asn Ser Asn Leu Val Cys Lys Val Ser Asp Phe Gly Met Ser
        755                 760                 765

Arg Val Leu Glu Asp Asp Pro Glu Ala Ala Tyr Thr Thr Arg Gly Gly
    770                 775                 780

Lys Ile Pro Ile Arg Trp Thr Ala Pro Glu Ala Ile Ala Tyr Arg Lys
785                 790                 795                 800

Phe Thr Ser Ala Ser Asp Val Trp Ser Tyr Gly Ile Val Met Trp Glu
                805                 810                 815

Val Met Ser Tyr Gly Glu Arg Pro Tyr Trp Asp Met Ser Asn Gln Asp
            820                 825                 830

Val Ile Lys Ala Ile Glu Glu Gly Tyr Arg Leu Pro Pro Pro Met Asp
        835                 840                 845

Cys Pro Ile Ala Leu His Gln Leu Met Leu Asp Cys Trp Gln Lys Glu
    850                 855                 860

Arg Ser Asp Arg Pro Lys Phe Gly Gln Ile Val Asn Met Leu Asp Lys
865                 870                 875                 880

Leu Ile Arg Asn Pro Asn Ser Leu Lys Arg Thr Gly Thr Glu Ser Ser
                885                 890                 895

Arg Pro Asn Thr Ala Leu Leu Asp Pro Ser Ser Pro Glu Phe Ser Ala
            900                 905                 910

Val Val Ser Val Gly Asp Trp Leu Gln Ala Ile Lys Met Asp Arg Tyr
        915                 920                 925

Lys Asp Asn Phe Thr Ala Ala Gly Tyr Thr Thr Leu Glu Ala Val Val
    930                 935                 940

His Val Asn Gln Glu Asp Leu Ala Arg Ile Gly Ile Thr Ala Ile Thr
945                 950                 955                 960

His Gln Asn Lys Ile Leu Ser Ser Val Gln Ala Met Arg Thr Gln Met
                965                 970                 975

Gln Gln Met His Gly Arg Met Val Pro Val
            980                 985

<210> SEQ ID NO 33
<211> LENGTH: 528
<212> TYPE: PRT
<213> ORGANISM: Macaca mulatta

<400> SEQUENCE: 33

Val Thr Gly Ser Arg Val Tyr Pro Ala Asn Glu Val Thr Leu Leu Asp
1               5                   10                  15

Ser Arg Ser Val Gln Gly Glu Leu Gly Trp Ile Ala Ser Pro Leu Glu
            20                  25                  30

Gly Gly Trp Glu Glu Val Ser Ile Met Asp Glu Lys Asn Thr Pro Ile

-continued

```
                35                  40                  45
Arg Thr Tyr Gln Val Cys Asn Val Met Glu Pro Ser Gln Asn Asn Trp
 50                  55                  60
Leu Arg Thr Asp Trp Ile Thr Arg Glu Gly Ala Gln Arg Val Tyr Ile
 65                  70                  75                  80
Glu Ile Lys Phe Thr Leu Arg Asp Cys Asn Ser Leu Pro Gly Val Met
                 85                  90                  95
Gly Thr Cys Lys Glu Thr Phe Asn Leu Tyr Tyr Tyr Glu Ser Asp Asn
                100                 105                 110
Asp Lys Glu Arg Phe Ile Arg Glu Asn Gln Phe Val Lys Ile Asp Thr
                115                 120                 125
Ile Ala Ala Asp Glu Ser Phe Thr Gln Val Asp Ile Gly Asp Arg Ile
130                 135                 140
Met Lys Leu Asn Thr Glu Ile Arg Asp Val Gly Pro Leu Ser Lys Lys
145                 150                 155                 160
Gly Phe Tyr Leu Ala Phe Gln Asp Val Gly Ala Cys Ile Ala Leu Val
                165                 170                 175
Ser Val Arg Val Phe Tyr Lys Lys Cys Pro Leu Thr Val Arg Asn Leu
                180                 185                 190
Ala Gln Phe Pro Asp Thr Ile Thr Gly Ala Asp Thr Ser Ser Leu Val
                195                 200                 205
Glu Val Arg Gly Ser Cys Val Asn Asn Ser Glu Glu Lys Asp Val Pro
                210                 215                 220
Lys Met Tyr Cys Gly Ala Asp Gly Glu Trp Leu Val Pro Ile Gly Asn
225                 230                 235                 240
Cys Leu Cys Asn Ala Gly His Glu Glu Arg Ser Gly Glu Cys Gln Ala
                245                 250                 255
Cys Lys Ile Gly Tyr Tyr Lys Ala Leu Ser Thr Asp Ala Thr Cys Ala
                260                 265                 270
Lys Cys Pro Pro His Ser Tyr Ser Val Trp Glu Gly Ala Thr Ser Cys
                275                 280                 285
Thr Cys Asp Arg Gly Phe Phe Arg Ala Asp Asn Asp Ala Ala Ser Met
                290                 295                 300
Pro Cys Thr Arg Pro Pro Ser Ala Pro Leu Asn Leu Ile Ser Asn Val
305                 310                 315                 320
Asn Glu Thr Ser Val Asn Leu Glu Trp Ser Ser Pro Gln Asn Thr Gly
                325                 330                 335
Gly Arg Gln Asp Ile Ser Tyr Asn Val Val Cys Lys Lys Cys Gly Ala
                340                 345                 350
Gly Asp Pro Ser Lys Cys Arg Pro Cys Gly Ser Gly Val His Tyr Thr
                355                 360                 365
Pro Gln Gln Asn Gly Leu Lys Thr Thr Lys Val Ser Ile Thr Asp Leu
                370                 375                 380
Leu Ala His Thr Asn Tyr Thr Phe Glu Ile Trp Ala Val Asn Gly Val
385                 390                 395                 400
Ser Lys Tyr Asn Pro Ser Pro Asp Gln Ser Val Ser Val Thr Val Thr
                405                 410                 415
Thr Asn Gln Ala Ala Pro Ser Ser Ile Ala Leu Val Gln Ala Lys Glu
                420                 425                 430
Val Thr Arg Tyr Ser Val Ala Leu Ala Trp Leu Glu Pro Asp Arg Pro
                435                 440                 445
Asn Gly Val Ile Leu Glu Tyr Glu Val Lys Tyr Tyr Glu Lys Asp Gln
                450                 455                 460
```

```
Asn Glu Arg Ser Tyr Arg Ile Val Arg Thr Ala Ala Arg Asn Thr Asp
465                 470                 475                 480

Ile Lys Gly Leu Asn Pro Leu Thr Ser Tyr Val Phe His Val Arg Ala
                485                 490                 495

Arg Thr Ala Ala Gly Tyr Gly Asp Phe Ser Glu Pro Leu Glu Val Thr
            500                 505                 510

Thr Asn Thr Val Pro Ser Arg Ile Ile Gly Asp Gly Ala Asn Ser Thr
        515                 520                 525
```

<210> SEQ ID NO 34
<211> LENGTH: 19
<212> TYPE: PRT
<213> ORGANISM: Homo sapiens

<400> SEQUENCE: 34

```
Met Ala Gly Ile Phe Tyr Phe Ala Leu Phe Ser Cys Leu Phe Gly Ile
1               5                   10                  15

Cys Asp Ala
```

<210> SEQ ID NO 35
<211> LENGTH: 15
<212> TYPE: PRT
<213> ORGANISM: Homo sapiens

<400> SEQUENCE: 35

```
Met Ser Ala Leu Leu Ile Leu Ala Leu Val Gly Ala Ala Val Ala
1               5                   10                  15
```

<210> SEQ ID NO 36
<211> LENGTH: 547
<212> TYPE: PRT
<213> ORGANISM: Homo sapiens

<400> SEQUENCE: 36

```
Met Ala Gly Ile Phe Tyr Phe Ala Leu Phe Ser Cys Leu Phe Gly Ile
1               5                   10                  15

Cys Asp Ala Val Thr Gly Ser Arg Val Tyr Pro Ala Asn Glu Val Thr
            20                  25                  30

Leu Leu Asp Ser Arg Ser Val Gln Gly Glu Leu Gly Trp Ile Ala Ser
            35                  40                  45

Pro Leu Glu Gly Gly Trp Glu Glu Val Ser Ile Met Asp Glu Lys Asn
        50                  55                  60

Thr Pro Ile Arg Thr Tyr Gln Val Cys Asn Val Met Glu Pro Ser Gln
65                  70                  75                  80

Asn Asn Trp Leu Arg Thr Asp Trp Ile Thr Arg Glu Gly Ala Gln Arg
                85                  90                  95

Val Tyr Ile Glu Ile Lys Phe Thr Leu Arg Asp Cys Asn Ser Leu Pro
            100                 105                 110

Gly Val Met Gly Thr Cys Lys Glu Thr Phe Asn Leu Tyr Tyr Tyr Glu
            115                 120                 125

Ser Asp Asn Asp Lys Glu Arg Phe Ile Arg Glu Asn Gln Phe Val Lys
        130                 135                 140

Ile Asp Thr Ile Ala Ala Asp Glu Ser Phe Thr Gln Val Asp Ile Gly
145                 150                 155                 160

Asp Arg Ile Met Lys Leu Asn Thr Glu Ile Arg Asp Val Gly Pro Leu
                165                 170                 175

Ser Lys Lys Gly Phe Tyr Leu Ala Phe Gln Asp Val Gly Ala Cys Ile
```

180                 185                 190
Ala Leu Val Ser Val Arg Val Phe Tyr Lys Cys Pro Leu Thr Val
            195                 200                 205

Arg Asn Leu Ala Gln Phe Pro Asp Thr Ile Thr Gly Ala Asp Thr Ser
            210                 215                 220

Ser Leu Val Glu Val Arg Gly Ser Cys Val Asn Asn Ser Glu Glu Lys
225                 230                 235                 240

Asp Val Pro Lys Met Tyr Cys Gly Ala Asp Gly Glu Trp Leu Val Pro
                245                 250                 255

Ile Gly Asn Cys Leu Cys Asn Ala Gly His Glu Glu Arg Ser Gly Glu
            260                 265                 270

Cys Gln Ala Cys Lys Ile Gly Tyr Tyr Lys Ala Leu Ser Thr Asp Ala
            275                 280                 285

Thr Cys Ala Lys Cys Pro Pro His Ser Tyr Ser Val Trp Glu Gly Ala
            290                 295                 300

Thr Ser Cys Thr Cys Asp Arg Gly Phe Phe Arg Ala Asp Asn Asp Ala
305                 310                 315                 320

Ala Ser Met Pro Cys Thr Arg Pro Pro Ser Ala Pro Leu Asn Leu Ile
                325                 330                 335

Ser Asn Val Asn Glu Thr Ser Val Asn Leu Glu Trp Ser Ser Pro Gln
            340                 345                 350

Asn Thr Gly Gly Arg Gln Asp Ile Ser Tyr Asn Val Val Cys Lys Lys
            355                 360                 365

Cys Gly Ala Gly Asp Pro Ser Lys Cys Arg Pro Cys Gly Ser Gly Val
            370                 375                 380

His Tyr Thr Pro Gln Gln Asn Gly Leu Lys Thr Thr Lys Val Ser Ile
385                 390                 395                 400

Thr Asp Leu Leu Ala His Thr Asn Tyr Thr Phe Glu Ile Trp Ala Val
                405                 410                 415

Asn Gly Val Ser Lys Tyr Asn Pro Asn Pro Asp Gln Ser Val Ser Val
            420                 425                 430

Thr Val Thr Thr Asn Gln Ala Ala Pro Ser Ser Ile Ala Leu Val Gln
            435                 440                 445

Ala Lys Glu Val Thr Arg Tyr Ser Val Ala Leu Ala Trp Leu Glu Pro
450                 455                 460

Asp Arg Pro Asn Gly Val Ile Leu Glu Tyr Glu Val Lys Tyr Tyr Glu
465                 470                 475                 480

Lys Asp Gln Asn Glu Arg Ser Tyr Arg Ile Val Arg Thr Ala Ala Arg
                485                 490                 495

Asn Thr Asp Ile Lys Gly Leu Asn Pro Leu Thr Ser Tyr Val Phe His
            500                 505                 510

Val Arg Ala Arg Thr Ala Ala Gly Tyr Gly Asp Phe Ser Glu Pro Leu
            515                 520                 525

Glu Val Thr Thr Asn Thr Val Pro Ser Arg Ile Ile Gly Asp Gly Ala
            530                 535                 540

Asn Ser Thr
545

<210> SEQ ID NO 37
<211> LENGTH: 328
<212> TYPE: PRT
<213> ORGANISM: Homo sapiens

<400> SEQUENCE: 37

```
Met Ala Gly Ile Phe Tyr Phe Ala Leu Phe Ser Cys Leu Phe Gly Ile
1               5                   10                  15

Cys Asp Ala Val Thr Gly Ser Arg Val Tyr Pro Ala Asn Glu Val Thr
            20                  25                  30

Leu Leu Asp Ser Arg Ser Val Gln Gly Glu Leu Gly Trp Ile Ala Ser
        35                  40                  45

Pro Leu Glu Gly Gly Trp Glu Glu Val Ser Ile Met Asp Glu Lys Asn
50                  55                  60

Thr Pro Ile Arg Thr Tyr Gln Val Cys Asn Val Met Glu Pro Ser Gln
65                      70                  75                  80

Asn Asn Trp Leu Arg Thr Asp Trp Ile Thr Arg Glu Gly Ala Gln Arg
                85                  90                  95

Val Tyr Ile Glu Ile Lys Phe Thr Leu Arg Asp Cys Asn Ser Leu Pro
                100                 105                 110

Gly Val Met Gly Thr Cys Lys Glu Thr Phe Asn Leu Tyr Tyr Tyr Glu
            115                 120                 125

Ser Asp Asn Asp Lys Glu Arg Phe Ile Arg Glu Asn Gln Phe Val Lys
        130                 135                 140

Ile Asp Thr Ile Ala Ala Asp Glu Ser Phe Thr Gln Val Asp Ile Gly
145                 150                 155                 160

Asp Arg Ile Met Lys Leu Asn Thr Glu Ile Arg Asp Val Gly Pro Leu
                165                 170                 175

Ser Lys Lys Gly Phe Tyr Leu Ala Phe Gln Asp Val Gly Ala Cys Ile
            180                 185                 190

Ala Leu Val Ser Val Arg Val Phe Tyr Lys Lys Cys Pro Leu Thr Val
        195                 200                 205

Arg Asn Leu Ala Gln Phe Pro Asp Thr Ile Thr Gly Ala Asp Thr Ser
    210                 215                 220

Ser Leu Val Glu Val Arg Gly Ser Cys Val Asn Asn Ser Glu Glu Lys
225                 230                 235                 240

Asp Val Pro Lys Met Tyr Cys Gly Ala Asp Gly Glu Trp Leu Val Pro
                245                 250                 255

Ile Gly Asn Cys Leu Cys Asn Ala Gly His Glu Glu Arg Ser Gly Glu
            260                 265                 270

Cys Gln Ala Cys Lys Ile Gly Tyr Tyr Lys Ala Leu Ser Thr Asp Ala
        275                 280                 285

Thr Cys Ala Lys Cys Pro Pro His Ser Tyr Ser Val Trp Glu Gly Ala
    290                 295                 300

Thr Ser Cys Thr Cys Asp Arg Gly Phe Phe Arg Ala Asp Asn Asp Ala
305                 310                 315                 320

Ala Ser Met Pro Cys Thr Arg Pro
                325

<210> SEQ ID NO 38
<211> LENGTH: 236
<212> TYPE: PRT
<213> ORGANISM: Homo sapiens

<400> SEQUENCE: 38

Pro Leu Thr Val Arg Asn Leu Ala Gln Phe Pro Asp Thr Ile Thr Gly
1               5                   10                  15

Ala Asp Thr Ser Ser Leu Val Glu Val Arg Gly Ser Cys Val Asn Asn
            20                  25                  30

Ser Glu Glu Lys Asp Val Pro Lys Met Tyr Cys Gly Ala Asp Gly Glu
        35                  40                  45
```

```
Trp Leu Val Pro Ile Gly Asn Cys Leu Cys Asn Ala Gly His Glu Glu
         50                  55                  60

Arg Ser Gly Glu Cys Gln Ala Cys Lys Ile Gly Tyr Tyr Lys Ala Leu
 65                  70                  75                  80

Ser Thr Asp Ala Thr Cys Ala Lys Cys Pro Pro His Ser Tyr Ser Val
                 85                  90                  95

Trp Glu Gly Ala Thr Ser Cys Thr Cys Asp Arg Gly Phe Phe Arg Ala
                100                 105                 110

Asp Asn Asp Ala Ala Ser Met Pro Cys Thr Arg Pro Pro Ser Ala Pro
            115                 120                 125

Leu Asn Leu Ile Ser Asn Val Asn Glu Thr Ser Val Asn Leu Glu Trp
        130                 135                 140

Ser Ser Pro Gln Asn Thr Gly Gly Arg Gln Asp Ile Ser Tyr Asn Val
145                 150                 155                 160

Val Cys Lys Lys Cys Gly Ala Gly Asp Pro Ser Lys Cys Arg Pro Cys
                165                 170                 175

Gly Ser Gly Val His Tyr Thr Pro Gln Gln Asn Gly Leu Lys Thr Thr
            180                 185                 190

Lys Val Ser Ile Thr Asp Leu Leu Ala His Thr Asn Tyr Thr Phe Glu
        195                 200                 205

Ile Trp Ala Val Asn Gly Val Ser Lys Tyr Asn Pro Asn Pro Asp Gln
    210                 215                 220

Ser Val Ser Val Thr Val Thr Asn Gln Ala Ala
225                 230                 235

<210> SEQ ID NO 39
<211> LENGTH: 112
<212> TYPE: PRT
<213> ORGANISM: Homo sapiens

<400> SEQUENCE: 39

Thr Asn Gln Ala Ala Pro Ser Ser Ile Ala Leu Val Gln Ala Lys Glu
 1               5                  10                  15

Val Thr Arg Tyr Ser Val Ala Leu Ala Trp Leu Glu Pro Asp Arg Pro
             20                  25                  30

Asn Gly Val Ile Leu Glu Tyr Glu Val Lys Tyr Tyr Glu Lys Asp Gln
         35                  40                  45

Asn Glu Arg Ser Tyr Arg Ile Val Arg Thr Ala Ala Arg Asn Thr Asp
     50                  55                  60

Ile Lys Gly Leu Asn Pro Leu Thr Ser Tyr Val Phe His Val Arg Ala
 65                  70                  75                  80

Arg Thr Ala Ala Gly Tyr Gly Asp Phe Ser Glu Pro Leu Glu Val Thr
                 85                  90                  95

Thr Asn Thr Val Pro Ser Arg Ile Ile Gly Asp Gly Ala Asn Ser Thr
                100                 105                 110

<210> SEQ ID NO 40
<211> LENGTH: 96
<212> TYPE: PRT
<213> ORGANISM: Artificial Sequence
<220> FEATURE:
<223> OTHER INFORMATION: Synthetic polypeptide

<400> SEQUENCE: 40

Asp Ile Gln Met Thr Gln Ser Pro Ser Ser Leu Ser Ala Ser Val Gly
 1               5                  10                  15
```

-continued

```
Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Pro
                85                  90                  95

<210> SEQ ID NO 41
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 41

Leu Thr Phe Gly Gly Gly Thr Lys Val Glu Ile Lys
1               5                   10

<210> SEQ ID NO 42
<211> LENGTH: 98
<212> TYPE: PRT
<213> ORGANISM: Artificial Sequence
<220> FEATURE:
<223> OTHER INFORMATION: Synthetic polypeptide

<400> SEQUENCE: 42

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 43
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 43

Tyr Tyr Tyr Tyr Gly Met Asp Val Trp Gly Gln Gly Thr Thr Val Thr
1               5                   10                  15

Val Ser

<210> SEQ ID NO 44
<211> LENGTH: 5
<212> TYPE: PRT
<213> ORGANISM: Artificial Sequence
<220> FEATURE:
```

<223> OTHER INFORMATION: Synthetic polypeptide

<400> SEQUENCE: 44

Arg Phe Gly Val His
1               5

<210> SEQ ID NO 45
<211> LENGTH: 125
<212> TYPE: PRT
<213> ORGANISM: Artificial Sequence
<220> FEATURE:
<223> OTHER INFORMATION: Synthetic polypeptide

<400> SEQUENCE: 45

Gln Val Gln Leu Val Glu Ser Gly Gly Gly Val Val Gln Pro Gly Arg
1               5                   10                  15

Ser Leu Arg Leu Ser Cys Ala Val Ser Gly Phe Ser Leu Thr Arg Phe
            20                  25                  30

Gly Val His Trp Val Arg Gln Ala Pro Gly Lys Gly Leu Glu Trp Val
        35                  40                  45

Ala Val Ile Trp Arg Gly Gly Ser Thr Asp Tyr Asn Ala Ala Phe Met
    50                  55                  60

Ser Arg Leu Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Lys Glu Ser Leu Phe Gly Val Tyr Tyr Asp Tyr Gly Tyr Tyr Ser Met
            100                 105                 110

Asp Tyr Trp Gly Gln Gly Thr Thr Val Thr Val Ser Ser
        115                 120                 125

<210> SEQ ID NO 46
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Leu Gln Gln Lys Pro Gly Lys Ala Pro Lys Arg Leu Ile
        35                  40                  45

Tyr Ala Ala Ser Thr Leu Asp Ser Gly Val Pro Ser Arg Phe Ser Gly
    50                  55                  60

Ser Arg Ser Gly Thr Glu Tyr Thr Leu Thr Ile Ser Ser Leu Gln Pro
65                  70                  75                  80

Glu Asp Phe Ala Thr Tyr Tyr Cys Leu Gln Tyr Ala Ser Tyr Pro Leu
                85                  90                  95

Thr Phe Gly Gly Gly Thr Lys Val Glu Ile Lys
            100                 105

<210> SEQ ID NO 47
<211> LENGTH: 326
<212> TYPE: PRT
<213> ORGANISM: Homo sapiens

<400> SEQUENCE: 47

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 48
<211> LENGTH: 107
<212> TYPE: PRT
<213> ORGANISM: Homo sapiens

<400> SEQUENCE: 48

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln

```
                35                  40                  45
Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 49
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 49
agatttggag tgcat                                                    15

<210> SEQ ID NO 50
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 50
gtgatctgga ggggaggatc caccgactac aacgctgctt ttatgagc                48

<210> SEQ ID NO 51
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 51
gagagcctgt tcggcgtgta ctatgactac ggctactatt ctatggatta t            51

<210> SEQ ID NO 52
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 52
cgcgcctccc aggagatctc tggctacctg tcc                                33

<210> SEQ ID NO 53
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 53
gctgcctcca ccctggactc t                                             21

<210> SEQ ID NO 54
<211> LENGTH: 27
<212> TYPE: DNA
<213> ORGANISM: Artificial Sequence

```
<220> FEATURE:
<223> OTHER INFORMATION: Synthetic polynucleotide

<400> SEQUENCE: 54
ctgcagtacg cttcctatcc actgacc                                            27

<210> SEQ ID NO 55
<211> LENGTH: 375
<212> TYPE: DNA
<213> ORGANISM: Artificial Sequence
<220> FEATURE:
<223> OTHER INFORMATION: Synthetic polynucleotide

<400> SEQUENCE: 55
caggtgcagc tggtggagag cggaggagga gtggtgcagc ctggcaggtc cctgaggctg        60
agctgtgccg tgtccggctt cagcctgaca agatttggag tgcattgggt gcgccaggct       120
ccaggcaagg gactggagtg ggtggccgtg atctggaggg aggatccac cgactacaac        180 gctgctttta tgagccggct gacaatctct aaggataact ccaagaatac cgtgtatctg       240
cagatgaact ccctgagggc tgaggacacc gccgtgtact attgcgccaa ggagagcctg       300
ttcggcgtgt actatgacta cggctactat tctatggatt attggggcca gggcaccaca       360
gtgacagtgt cctcc                                                        375

<210> SEQ ID NO 56
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 56
gatatccaga tgacacagtc cccttccagc ctgtctgcct ccgtgggcga cagagtgacc        60
atcacatgtc gcgcctccca ggagatctct ggctacctgt cctggctgca gcagaagcca       120
ggcaaggctc ccaagcgcct gatctatgct gcctccaccc tggactctgg agtgccttcc       180
aggttcagcg gctctcggtc cggcacagag tacaccctga caatctcttc cctgcagcct       240
gaggatttcg ccacctacta ttgcctgcag tacgcttcct atccactgac ctttggcggc       300
ggcacaaagg tggagatcaa g                                                 321

<210> SEQ ID NO 57
<211> LENGTH: 978
<212> TYPE: DNA
<213> ORGANISM: Artificial Sequence
<220> FEATURE:
<223> OTHER INFORMATION: Synthetic polynucleotide

<400> SEQUENCE: 57
gcctccacca agggaccatc cgtgttccca ctggccccat cttccgggag cacatctgag        60
tccaccgccg ctctgggctg tctggtgaag gattacttcc ctgagccagt gacagtgtct       120
tggaactccg gcgctctgac atccggcgtg cacacctttc ctgccgtgct gcagagctct       180
ggcctgtaca gcctgtccag cgtggtgacc gtgccctctt ccaatttcgg cacccagaca       240
tatacctgca acgtggacca taagccttcc aatacaaagg tggataagac cgtggagaga       300
aagagctgcg tggagtgtcc accttgccca gctccaccag ccgctgcccc tagcgtgttc       360
ctgtttcctc caaagccaaa ggacacactg atgatctctc gcacacccga ggtgacctgc       420
gtggtggtgg acgtgtccca cgaggatcca gaggtgcagt ttaactggta cgtggatggc       480
```

```
gtggaggtgc ataatgctaa gaccaagccc agggaggagc agttcaactc cacatttcgg    540
gtggtgagcg tgctgaccgt ggtgcaccag gactggctga acggcaagga gtataagtgt    600
aaggtgagca ataagggcct gcccgcccct atcgagaaga caatctctaa gaccaagggc    660
cagcctagag agccacaggt gtacaccctg ccccttctc gcgaggagat gacaaagaac    720
caggtgtccc tgacctgcct ggtgaagggc ttctatccta gcgacatcgc tgtggagtgg    780
gagtctaatg ccagccaga gaacaattac aagaccacac cacccatgct ggacagcgat    840
ggctctttct ttctgtattc taagctgaca gtggataagt ccaggtggca gcagggcaac    900
gtgtttagct gctctgtgat gcatgaggcc ctgcacaatc attacaccca gaagtccctg    960
agcctgtctc caggcaag                                                  978
```

```
<210> SEQ ID NO 58
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 58
aggacagtgg ccgctccatc cgtgttcatc tttccccta gcgacgagca gctgaagagc     60
ggcaccgcct ctgtggtgtg cctgctgaac aatttctacc ccaggaggc caaggtgcag    120 tggaaggtg ataacgctct gcagagcggc aattctcagg agtccgtgac cgagcaggac    180
agcaaggatt ctacatattc cctgagctct accctgacac tgagcaaggc cgattacgag    240
aagcacaagg tgtatgcttg cgaggtgacc catcagggcc tgtccagccc agtgacaaag    300
tcttttaaca gggcgagtg t                                              321
```

```
<210> SEQ ID NO 59
<211> LENGTH: 451
<212> TYPE: PRT
<213> ORGANISM: Artificial Sequence
<220> FEATURE:
<223> OTHER INFORMATION: Synthetic polypeptide

<400> SEQUENCE: 59

Gln Val Gln Leu Val Glu Ser Gly Gly Gly Val Val Gln Pro Gly Arg
1               5                   10                  15

Ser Leu Arg Leu Ser Cys Ala Val Ser Gly Phe Ser Leu Thr Arg Phe
            20                  25                  30

Gly Val His Trp Val Arg Gln Ala Pro Gly Lys Gly Leu Glu Trp Val
        35                  40                  45

Ala Val Ile Trp Arg Gly Gly Ser Thr Asp Tyr Asn Ala Ala Phe Met
    50                  55                  60

Ser Arg Leu Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Lys Glu Ser Leu Phe Gly Val Tyr Tyr Asp Tyr Gly Tyr Tyr Ser Met
            100                 105                 110

Asp Tyr Trp Gly Gln Gly Thr Thr Val Thr Val Ser Ser Ala Ser Thr
        115                 120                 125

Lys Gly Pro Ser Val Phe Pro Leu Ala Pro Ser Ser Arg Ser Thr Ser
    130                 135                 140

Glu Ser Thr Ala Ala Leu Gly Cys Leu Val Lys Asp Tyr Phe Pro Glu
145                 150                 155                 160
```

```
Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Ser Cys Val Glu Cys Pro Pro Cys Pro Ala Pro Pro Ala Ala
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 60
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Leu Gln Gln Lys Pro Gly Lys Ala Pro Lys Arg Leu Ile
        35                  40                  45

Tyr Ala Ala Ser Thr Leu Asp Ser Gly Val Pro Ser Arg Phe Ser Gly
    50                  55                  60
```

Ser Arg Ser Gly Thr Glu Tyr Thr Leu Thr Ile Ser Ser Leu Gln Pro
65                  70                  75                  80

Glu Asp Phe Ala Thr Tyr Tyr Cys Leu Gln Tyr Ala Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 61
<211> LENGTH: 1353
<212> TYPE: DNA
<213> ORGANISM: Artificial Sequence
<220> FEATURE:
<223> OTHER INFORMATION: Synthetic polynucleotide

<400> SEQUENCE: 61
caggtgcagc tggtggagag cggaggagga gtggtgcagc tggcaggtc cctgaggctg      60 agctgtgccg tgtccggctt cagcctgaca gatttggag tgcattgggt gcgccaggct     120
ccaggcaagg gactggagtg ggtggccgtg atctggaggg gaggatccac cgactacaac     180 gctgcttta tgagccggct gacaatctct aaggataact ccaagaatac cgtgtatctg     240
cagatgaact ccctgagggc tgaggacacc gccgtgtact attgcgccaa ggagagcctg     300
ttcggcgtgt actatgacta cggctactat tctatggatt attggggcca gggcaccaca     360
gtgacagtgt cctccgcctc caccaaggga ccatccgtgt tcccactggc ccatcttcc     420 cggagcacat ctgagtccac cgccgctctg gctgtctgg tgaaggatta cttccctgag     480
ccagtgacag tgtcttggaa ctccggcgct ctgacatccg gcgtgcacac ctttcctgcc     540
gtgctgcaga gctctggcct gtacagcctg tccagcgtgg tgaccgtgcc ctcttccaat     600
ttcggcaccc agacatatac ctgcaacgtg accataagc cttccaatac aaaggtggat     660
aagaccgtgg agagaaagag ctgcgtggag tgtccacctt gcccagctcc accagccgct     720
gcccctagcg tgttcctgtt tcctccaaag ccaaaggaca cactgatgat ctctcgcaca     780
cccgaggtga cctgcgtggt ggtggacgtg tcccacgagg atccagaggt gcagtttaac     840
tggtacgtgg atggcgtgga ggtgcataat gctaagacca gcccaggga ggagcagttc     900 aactccacat ttcgggtggt gagcgtgctg accgtggtgc accaggactg gctgaacggc     960
aaggagtata gtgtaaggt gagcaataag ggcctgcccg cccctatcga agacaatc      1020 tctaagacca agggccagcc tagagagcca caggtgtaca ccctgccccc ttctcgcgag    1080
gagatgacaa agaaccaggt gtccctgacc tgcctggtga agggcttcta tcctagcgac    1140

```
atcgctgtgg agtgggagtc taatggccag ccagagaaca attacaagac cacaccaccc      1200
atgctggaca gcgatggctc tttctttctg tattctaagc tgacagtgga taagtccagg      1260
tggcagcagg gcaacgtgtt tagctgctct gtgatgcatg aggccctgca caatcattac      1320
acccagaagt ccctgagcct gtctccaggc aag                                   1353

<210> SEQ ID NO 62
<211> LENGTH: 642
<212> TYPE: DNA
<213> ORGANISM: Artificial Sequence
<220> FEATURE:
<223> OTHER INFORMATION: Synthetic polynucleotide

<400> SEQUENCE: 62
gatatccaga tgacacagtc cccttccagc ctgtctgcct ccgtgggcga cagagtgacc        60
atcacatgtc gcgcctccca ggagatctct ggctacctgt cctggctgca gcagaagcca       120
ggcaaggctc ccaagcgcct gatctatgct gcctccaccc tggactctgg agtgccttcc       180
aggttcagcg gctctcggtc cggcacagag tacaccctga caatctcttc cctgcagcct       240
gaggatttcg ccacctacta ttgcctgcag tacgcttcct atccactgac ctttggcggc       300
ggcacaaagg tggagatcaa gaggacagtg gccgctccat ccgtgttcat ctttcccct       360 agcgacgagc agctgaagag cggcaccgcc tctgtggtgt gcctgctgaa caatttctac      420
cccagggagg ccaaggtgca gtggaaggtg gataacgctc tgcagagcgg caattctcag      480
gagtccgtga ccgagcagga cagcaaggat tctacatatt ccctgagctc taccctgaca      540
ctgagcaagg ccgattacga gaagcacaag gtgtatgctt gcgaggtgac ccatcagggc      600
ctgtccagcc cagtgacaaa gtcttttaac aggggcgagt gt                         642
```

ANTI-EPHA4 ANTIBODY

TECHNICAL FIELD

The present invention relates to an antibody that binds to EphA4, a nucleic acid that encodes the antibody, a vector that comprises the nucleic acid, a cell comprising the vector, a method of producing the antibody, and a pharmaceutical composition comprising the antibody.

BACKGROUND ART

EphA4 is a member of the receptor tyrosine kinase family. Ephrin type A and type B are known as ligands for EphA4, and when EphA4 binds with ephrin which is a ligand thereof, de-adhesion signal is induced. So far, the involvement of EphA4 in the pathology of Alzheimer's disease (hereinafter also referred to as "AD") has been suggested (Non-Patent Literatures 1-4), and it has been reported that the inhibition of binding between EphA4 and ephrin rescues amyloid β $(Aβ)_{1-42}$, olygomer-mediated dysfunction of neurotransmission (Patent Literature 1). In AD, it is thought that aggregates (neurofibrillary tangles) formed by excessively phosphorylated tau are involved in nerve cell death (Non-Patent Literature 5), and it has also been reported that suppression of tau phosphorylation suppresses neurodegeneration of synapse disappearance (Non-Patent Literature 6 and Non-Patent Literature 7), as well as improves memory deficits or cognitive dysfunction (Non-Patent Literatures 8-11). There are reports suggesting that activation of CDK5 is a cause of tau phosphorylation (Non-Patent Literature 12 and Non-Patent Literature 13). A genetically modified mouse expressing a P301L mutation which has been found in familial frontotemporal dementia (rTg4510 mouse) is an AD model mouse, and similary to AD, hyperphosphorylation of tau and abnormal accumulation of tau in neuronal cells are found in the mouse. In rTg4510 mouse, neurofibrillary tangles, a pathological feature of AD, are formed and bring cognitive dysfunction by brain atrophy and loss of neuron (Non-Patent Literature 14 and Non-Patent Literature 5).

EphA4 is abundantly expressed in the hippocampus or the cerebral cortex, and is neural activity-dependently cleaved by matrix metalloprotease (MMP), ADAM (a disintegrin and metalloproteinase), and γ selectase. It is known that this cleavage reaction of EphA4 stabilizes the spine which is a key structure in neural function (Non-Patent Literature 15). It has been reported that the density of spine is decreased in AD (Non-Patent Literature 16), and since decrease of cleaved fragments of EphA4 is also confirmed in AD at NFT stages V and VI, it is thought that EphA4 cleavage reaction is involved in the pathology of AD (Non-Patent Literature 17).

Although KYL peptide and compound 1 etc. are known as existing EphA4 inhibitory drugs (Patent Literature 2, Non-Patent Literature 18, and Non-Patent Literature 19), there has been no reports regarding an antibody having activity that enhances the cleavage of EphA4.

CITATION LIST

[Patent Literature 1] WO2016/019280A1
[Patent Literature 2] WO2012/156351A1
[Non-Patent Literature 1] Vargas L M et al., PLoS One. 2014 Mar. 21; 9 (3)
[Non-Patent Literature 2] Fu A K et al., Proc Natl Acad Sci USA. 2014 Jul. 8; 111 (27): 9959-64
[Non-Patent Literature 3] Rosenberger A F et al., Acta Neuropathol Commun. 2014 Jul. 16; 2: 79
[Non-Patent Literature 4] Huang T Y et al., J Exp Med. 2017 Dec. 4; 214 (12): 3669-3685.
[Non-Patent Literature 5] Santa Cruz et al., Science. 2005 Jul. 15; 309 (5733): 476-81
[Non-Patent Literature 6] Seo J et al., J Neurosci. 2017 Oct. 11; 37 (41): 9917-9924
[Non-Patent Literature 7] Patrick G N et al., Nature. 1999 Dec. 9; 402 (6762): 615-22.
[Non-Patent Literature 8] Onishi T et al., J Neurochem. 2011 December; 119 (6): 1330-40
[Non-Patent Literature 9] Belfiore R et al., Aging Cell. 2019 February; 18 (1): e12873.
[Non-Patent Literature 10] Webster S J et al., Front Genet. 2014 Apr. 23; 5: 88.
[Non-Patent Literature 11] Grayson B et al., Behav Brain Res. 2015 May 15; 285: 176-93.
[Non-Patent Literature 12] Cancino G I et al., Neurobiol Aging. 2011 July; 32 (7): 1249-61.
[Non-Patent Literature 13] Vargas L M et al., Biochim Biophys Acta Mol Basis Dis. 2018 April; 1864: 1148-1159.
[Non-Patent Literature 14] Ramsden M et al., J Neurosci. 2005 Nov. 16; 25 (46): 10637-47.
[Non-Patent Literature 15] Inoue E et al., J Cell Biol. 2009 May 4; 185 (3): 551-64
[Non-Patent Literature 16] Boros et al., Ann Neurol. 2017 October; 82 (4): 602-614
[Non-Patent Literature 17] Matsui C et al., Brain Pathol. 2012 November; 22 (6): 776-87. doi: 10.1111/j.1750-3639
[Non-Patent Literature 18] Goldshmit et al., PLoS one. 2011; 6 (9): e24636
[Non-Patent Literature 19] Van Hoecke et al., Nature Medicine. 2012 September; 18 (9): 1418-22, 2012

SUMMARY OF THE INVENTION

Problems to be Solved by the Invention

The object of the present disclosure is to provide an anti-EphA4 antibody that can bind to EphA4 and enhance the cleavage of EphA4, as well as a pharmaceutical composition comprising the antibody as the active ingredient.

Means for Solving the Problems

As a result of extensive investigation to solve the above problems, the present inventors obtained a mouse anti-EphA4 monoclonal antibody that can bind to EphA4 and enhance the cleavage of EphA4, and produced a humanized antibody of the antibody to thereby come to complete the antibody of interest.

The present disclosure encompasses the following characteristics.

(1) An anti-EphA4 antibody, wherein the anti-EphA4 antibody comprises heavy and light chains, and comprises:
(a) a heavy chain CDR1 consisting of the amino acid sequence shown in SEQ ID NO. 44;
(b) a heavy chain CDR2 consisting of the amino acid sequence shown in SEQ ID NO. 27;
(c) a heavy chain CDR3 consisting of the amino acid sequence shown in SEQ ID NO. 28;
(d) a light chain CDR1 consisting of the amino acid sequence shown in SEQ ID NO. 29;

(e) a light chain CDR2 consisting of the amino acid sequence shown in SEQ ID NO. 30; and
(f) a light chain CDR3 consisting of the amino acid sequence shown in SEQ ID NO. 31.

(2) The anti-EphA4 antibody according to (1), wherein the anti-EphA4 antibody is humanized.

(3) The anti-EphA4 antibody according to (1) or (2), wherein the anti-EphA4 antibody specifically binds to EphA4 and enhances the cleavage of EphA4.

(4) The anti-EphA4 antibody according to any of (1)-(3), wherein the anti-EphA4 antibody specifically binds to EphA4 and inhibits the binding between EphA4 and ephrin.

(5) The anti-EphA4 antibody according to any of (1)-(4), wherein
the variable region of the heavy chain consists of the amino acid sequence shown in SEQ ID NO. 45, and
the variable region of the light chain consists of the amino acid sequence shown in SEQ ID NO. 46.

(6) The anti-EphA4 antibody according to any of (1)-(5), wherein
the constant region of the heavy chain and the constant region of the light chain comprise amino acid sequences derived from a human antibody.

(7) The anti-EphA4 antibody according to (6), wherein the constant region of the heavy chain is the constant region of human IgG.

(8) The anti-EphA4 antibody according to (7), wherein the constant region of human IgG is the constant region of human $IgG_2$.

(9) The anti-EphA4 antibody according to (8), wherein the constant region of human $IgG_2$ comprises the amino acid sequence shown in SEQ ID NO. 47.

(10) The anti-EphA4 antibody according to any of (6)-(9), wherein
the constant region of the light chain is the constant region of human IgK.

(11) The anti-EphA4 antibody according to (10), wherein the constant region of human IgK comprises the amino acid sequence shown in SEQ ID NO. 48.

(12) An anti-EphA4 antibody, wherein
the anti-EphA4 antibody comprises heavy and light chains,
the heavy chain comprises the amino acid sequence shown in SEQ ID NO. 59, and
the light chain comprises the amino acid sequence shown in SEQ ID NO. 60.

(13) The anti-EphA4 antibody according to (12), wherein the C-terminal lysine of the heavy chain is deleted.

(14) An anti-EphA4 antibody, wherein
the anti-EphA4 antibody comprises heavy and light chains,
the heavy chain comprises the amino acid sequence shown in SEQ ID NO. 59,
the light chain comprises the amino acid sequence shown in SEQ ID NO. 60, and
the C-terminal lysine of the heavy chain is deleted.

(15) An isolated nucleic acid encoding the anti-EphA4 antibody according to any of (1)-(14).

(16) A vector comprising the nucleic acid according to (15).

(17) A host cell comprising the vector according to (16).

(18) A method of producing an anti-EphA4 antibody, comprising a step of culturing the host cell according to (17).

(19) A pharmaceutical composition comprising the anti-EphA4 antibody according to any of (1)-(14).

(20) A pharmaceutical composition according to (19), wherein the pharmaceutical composition comprises at least one pharmaceutically acceptable carrier.

(21) The pharmaceutical composition according to (19) or (20), for treating Alzheimer's disease.

(22) The anti-EphA4 antibody according to any of (1)-(14) for use in the treatment of Alzheimer's disease.

(23) A method for treating Alzheimer's disease, comprising administering to a patient in need thereof a therapeutically effective amount of the anti-EphA4 antibody according to any of (1)-(14).

(24) Use of the anti-EphA4 antibody according to any of (1)-(14) for manufacturing a pharmaceutical composition for treating Alzheimer's disease.

(25) The pharmaceutical composition according to (19) or (20), for treating tauopathy.

(26) The anti-EphA4 antibody according to any of (1)-(14) for use in the treatment of tauopathy.

(27) A method for treating tauopathy, comprising administering to a patient in need thereof a therapeutically effective amount of the anti-EphA4 antibody according to any of (1)-(14).

(28) Use of the anti-EphA4 antibody according to any of (1)-(14) for manufacturing a pharmaceutical composition for treating tauopathy.

(29) The pharmaceutical composition, the anti-EphA4 antibody, the method for treating, or the use according to any of (25)-(28), wherein the tauopathy is Alzheimer's disease or frontotemporal lobar degeneration with tau pathology.

(30) The pharmaceutical composition, the anti-EphA4 antibody, the method for treating, or the use according to (29), wherein the tauopathy is Alzheimer's disease.

(31) The pharmaceutical composition, the anti-EphA4 antibody, the method for treating, or the use according to (29), wherein the tauopathy is frontotemporal lobar degeneration with tau pathology.

(32) The pharmaceutical composition, the anti-EphA4 antibody, the method for treating, or the use according to (31), wherein the frontotemporal lobar degeneration with tau pathology is progressive supranuclear palsy, corticobasal degeneration, argyrophilic grain dementia, senile dementia of the neurofibrillary tangle type, or Pick's disease.

(33) The pharmaceutical composition, the anti-EphA4 antibody, the method for treating, or the use according to (32), wherein the frontotemporal lobar degeneration with tau pathology is progressive supranuclear palsy.

(34) The pharmaceutical composition, the anti-EphA4 antibody, the method for treating, or the use according to (32), wherein the frontotemporal lobar degeneration with tau pathology is corticobasal degeneration.

(35) The pharmaceutical composition, the anti-EphA4 antibody, the method for treating, or the use according to (32), wherein the frontotemporal lobar degeneration with tau pathology is argyrophilic grain dementia.

(36) The pharmaceutical composition, the anti-EphA4 antibody, the method for treating, or the use according to (32), wherein the frontotemporal lobar degeneration with tau pathology is senile dementia of the neurofibrillary tangle type.

(37) The pharmaceutical composition, the anti-EphA4 antibody, the method for treating, or the use according to (32), wherein the frontotemporal lobar degeneration with tau pathology is Pick's disease.

Effects of the Invention

The present disclosure provides an anti-EphA4 antibody that can bind to EphA4 and enhance the cleavage of EphA4, a nucleic acid that encodes the antibody, a vector that comprises the nucleic acid, a cell comprising the vector, a method of producing the antibody, and a pharmaceutical composition comprising the antibody as the active ingredient.

BRIEF DESCRIPTION OF THE DRAWINGS

In FIG. 11B, amino acid names and residue numbers contained in the binding region are shown at the corresponding positions, and the CDRs of H-chain and L-chain of the binding antibody A-Fab are shown in a ribbon model.

DESCRIPTION OF EMBODIMENTS

Figure 1:
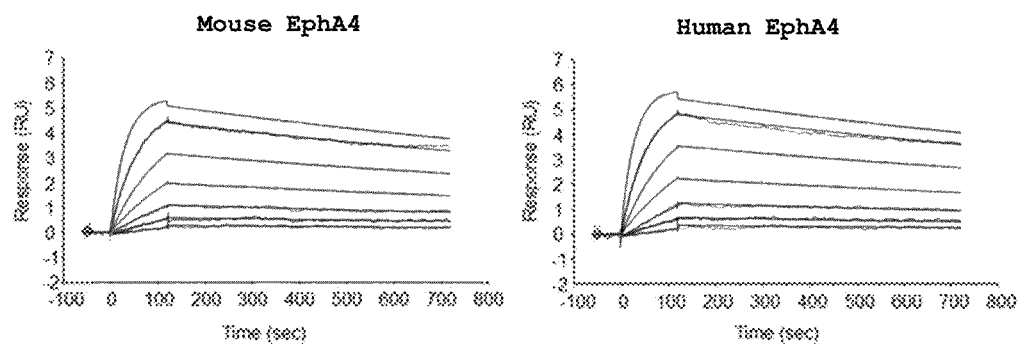
FIG. 1 shows the binding affinity of the anti-EphA4 monoclonal antibody (antibody A) against mouse and human EphA4.

The regions specified or coded by the SEQ ID NOs. used herein are as follows:

| Seq No. | Sequence Region |
|---|---|
| 1 | Mouse EphA4 (amino acid sequence) |
| 2 | Extracellular region of mouse EphA4 (amino acid sequence) |
| 3 | Mouse EphA4 extracellular region-SEAP-His protein (amino acid sequence) |
| 4 | Signal sequence of mouse EphA4 (amino acid sequence) |
| 5 | Human EphA4 (amino acid sequence) |
| 6 | Extracellular region of human EphA4 (amino acid sequence) |
| 7 | OligoDNA ad29S (nucleic acid sequence) |
| 8 | OligoDNA ad29AS (nucleic acid sequence) |
| 9 | 5' Forward primer (nucleic acid sequence) |
| 10 | 3' Reverse primer for mouse IgG heavy chain (nucleic acid sequence) |
| 11 | 3' Reverse primer for mouse Igκ light chain (nucleic acid sequence) |
| 12 | Heavy chain signal sequence of antibody A (amino acid sequence) |
| 13 | Heavy chain variable region of antibody A (amino acid sequence) |
| 14 | Light chain signal sequence of antibody A (amino acid sequence) |
| 15 | Light chain variable region of antibody A (amino acid sequence) |
| 16 | Heavy chain signal sequence of antibody A (nucleic acid sequence) |
| 17 | Heavy chain variable region of antibody A (nucleic acid sequence) |
| 18 | Light chain signal sequence of antibody A (nucleic acid sequence) |
| 19 | Light chain variable region of antibody A (nucleic acid sequence) |
| 20 | 5' Forward primer for antibody A heavy chain (nucleic acid sequence) |
| 21 | 5' Forward primer for antibody A light chain (nucleic acid sequence) |
| 22 | 3' Reverse primer for antibody A heavy chain (nucleic acid sequence) |
| 23 | 3' Reverse primer for antibody A light chain (nucleic acid sequence) |
| 24 | Heavy chain constant region of antibody A (amino acid sequence) |

-continued

| Seq No. | Sequence Region |
|---|---|
| 25 | Light chain constant region of antibody A (amino acid sequence) |
| 26 | Heavy chain CDR1 of antibody A (amino acid sequence) |
| 27 | Heavy chain CDR2 of antibody A (amino acid sequence) |
| 28 | Heavy chain CDR3 of antibody A (amino acid sequence) |
| 29 | Light chain CDR1 of antibody A (amino acid sequence) |
| 30 | Light chain CDR2 of antibody A (amino acid sequence) |
| 31 | Light chain CDR3 of antibody A (amino acid sequence) |
| 32 | Monkey EphA4 (amino acid sequence) |
| 33 | Extracellular region of monkey EphA4 (amino acid sequence) |
| 34 | Signal sequence of human EphA4 (amino acid sequence) |
| 35 | Signal sequence of preprotrypsin (amino acid sequence) |
| 36 | Extracellular region of human EphA4 (amino acid sequence) |
| 37 | Ligand binding domain of human EphA4 (amino acid sequence) |
| 38 | Fibronectin type III domain 1 of human EphA4 (amino acid sequence) |
| 39 | Fibronectin type III domain 2 of human EphA4 (amino acid sequence) |
| 40 | Light chain FR IGKV1-17*01 of human antibody (amino acid sequence) |
| 41 | Light chain FR JK4 of human antibody (amino acid sequence) |
| 42 | Heavy chain FR IGHV3-33*03 of human antibody (amino acid sequence) |
| 43 | Heavy chain FR JH6 of human antibody (amino acid sequence) |
| 44 | Heavy chain CDR1 of antibody B (amino acid sequence) |
| 45 | Heavy chain variable region HK2-42 of antibody B (amino acid sequence) |
| 46 | Light chain variable region L1-8 of antibody B (amino acid sequence) |
| 47 | Human IgG2 heavy chain constant region of antibody B (amino acid sequence) |
| 48 | Human Igκ light chain constant region of antibody B (amino acid sequence) |
| 49 | Heavy chain CDR1 of antibody B (nucleic acid sequence) |
| 50 | Heavy chain CDR2 of antibody B (nucleic acid sequence) |
| 51 | Heavy chain CDR3 of antibody B (nucleic acid sequence) |
| 52 | Light chain CDR1 of antibody B (nucleic acid sequence) |
| 53 | Light chain CDR2 of antibody B (nucleic acid sequence) |
| 54 | Light chain CDR3 of antibody B (nucleic acid sequence) |
| 55 | Heavy chain variable region HK2-42 of antibody B (nucleic acid sequence) |
| 56 | Light chain variable region L1-8 of antibody B (nucleic acid sequence) |
| 57 | Human IgG$_2$ heavy chain constant region of antibody B (nucleic acid sequence) |
| 58 | Human Igκ light chain constant region of antibody B (nucleic acid sequence) |
| 59 | Heavy chain full length sequence of antibody B (amino acid sequence) |
| 60 | Light chain full length sequence of antibody B (amino acid sequence) |
| 61 | Heavy chain full length sequence of antibody B (nucleic acid sequence) |
| 62 | Light chain full length sequence of antibody B (nucleic acid sequence) |

The present disclosure relates to an anti-EphA4 antibody that binds to EphA4.

The anti-EphA4 antibody according to the present disclosure is an antibody that can recognize and bind to EphA4, and as described below, the antibody may be an intact antibody, or may be a synthetic antibody (such as a recombinant antibody, a chimeric antibody, a humanized antibody, and the like), as long as it possesses binding affinity with EphA4. EphA4 herein can be understood as referring to human-, mouse-, rat-, and monkey-derived EphA4. Human-, mouse-, rat-, and monkey-derived EphA4 can be obtained from a public database where sequence information is registered, such as Genbank provided by the United States National Center for Biotechnology Information, or EphA4 gene sequence information can be obtained by designing primers based on the base sequence information of EphA4 of a closely related animal specie, and then cloning from RNA extracted from the desired animal specie. For example, the base sequence information of human, mouse, rat, and monkey EphA4 is registered in the database as Genbank Accession Nos. NM_004438.5, NM_007936.3, NM_001162411.1, and NM_001260870.1, respectively.

In one aspect, the anti-EphA4 antibody is an antibody that specifically binds to EphA4. The term "specific binding" is a term well-known to those skilled in the pertaining technical field, and methods for determining the specific binding between an antibody or an antigen binding fragment thereof and an antigen or an epitope are also well-known. In one embodiment, "specific binding" is understood as that the anti-EphA4 antibody can bind to EphA4 by immunological reaction with higher binding affinity and binding activity, more rapidly, and/or for a longer period of time compared to when binding with other target molecules. This does not mean that the antibody that specifically binds to EphA4 does not bind to other target molecules. In another embodiment, "specific binding" may be shown by an antibody having a KD against EphA4 of at least about 10-M, or at least about $10^{-8}$ M, or at least about $10^{-9}$ M, or lower. Moreover, in another further embodiment, "specific binding" is understood as binding to EphA4 by immunological reaction but does not substantially bind to other family molecules of the Eph receptor.

In one aspect, the anti-EphA4 antibody is an antibody that binds to the extracellular region of EphA4. In one embodiment, the anti-EphA4 antibody is an antibody that binds to the ligand binding domain (LBD) among the extracellular regions of EphA4.

In one embodiment, the anti-EphA4 antibody can specifically bind to EphA4 and enhance the cleavage of EphA4. In a particular embodiment, the anti-EphA4 antibody can specifically bind to EphA4 and enhance the cleavage of the EphA4 extracellular domain by matrix metalloprotease (MMP) or ADAM (a disintegrin and metalloproteinase).

In one embodiment, the anti-EphA4 antibody can specifically bind to EphA4 and inhibit the binding between EphA4 and ephrin which is a ligand thereof.

In another embodiment, the anti-EphA4 antibody can specifically bind to EphA4 and increase the number of spines in the hippocampus neuron or stabilize the spines in the hippocampus neuron.

In one embodiment, the present disclosure encompasses an anti-EphA4 antibody that can specifically bind to at least one of human EphA4, mouse EphA4, rat EphA4, and monkey EphA4 and inhibit the binding with a ligand thereof. In another embodiment, the present disclosure encompasses an anti-EphA4 antibody that can specifically bind to two or more of human EphA4, mouse EphA4, rat EphA4, and monkey EphA4 and inhibit the binding with a ligand thereof. In another further embodiment, the present disclosure encompasses an anti-EphA4 antibody that can specifically bind to all of human EphA4, mouse EphA4, rat EphA4, and monkey EphA4 and inhibit the binding with a ligand thereof.

For the method for measuring the antigen binding property (such as binding affinity and cross-species reactivity) of the anti-EphA4 antibody, methods well-known to those skilled in the art in the pertaining technical field may be employed. For example, binding affinity may be measured using, but not limited to, Biacore™ biosensor, KinExA biosensor, scintillation proximity assay, ELISA, ORIGEN immunoassay (IGEN), flow cytometry, fluorescence quenching, fluorescence metastasis, yeast display, and/or immunostaining. The neutralizing activity of anti-EphA4 antibody against the binding between EphA4 and a ligand thereof may be measured using, but not limited to, Biacore™ biosensor, ELISA, and/or flow cytometry.

The anti-EphA4 antibody according to the present disclosure may be a monoclonal antibody as long as it binds to EphA4.

The anti-EphA4 antibody according to the present disclosure may be of any class such as IgG, IgA, or IgM (or subclasses thereof), and is not limited to a particular class. Immunoglobulins are classified into different classes depending on the antibody amino acid sequence of the constant region of the heavy chain (may be referred to as H-chain). There are five major immunoglobulin classes: IgA, IgD, IgE, IgG, and IgM, and some of these may be further subdivided into subclasses (isotypes) of e.g. $IgG_1$, $IgG_2$, $IgG_3$, $IgG_4$, $IgA_1$, and $IgA_2$. The constant regions of the heavy chain corresponding to the different classes of immunoglobulins are called α, δ, ε, γ, and μ, respectively. Moreover, the types of the light chain (may be referred to as L-chain) of the antibody are the λ chain and the κ chain. The anti-EphA4 antibody according to the present disclosure may be an IgG antibody, for example may be an $IgG_1$ antibody or an $IgG_2$ antibody, and the like. Moreover, the anti-EphA4 antibody according to the present disclosure may be in some instances in the form of a monomer, a dimer, or a multimer.

The variable region of the antibody according to the present disclosure may mean the variable region of the antibody light chain and/or the variable region of the antibody heavy chain, and the constant region of the antibody may mean the constant region of the antibody light chain and/or the constant region of the antibody heavy chain. The variable regions of the heavy and light chains each consist of four framework regions (FRs) connected by three CDRs also known as complementarity-determining regions. The CDRs in each chain are kept in proximity by FRs, and along with the CDRs in the other chain, contribute to the formation of the antigen binding site of the antibody. Technologies for determining CDRs include, but are not limited to, for example, (1) an approach based on cross-species sequence variability (e.g. Kabat et al, Sequences of Proteins of Immunological Interest, 5th ed., 1991, National Institutes of Health, Bethesda Md.); and (2) an approach based on crystal structure research of antigen-antibody complexes (Al-lazikani et al., 1997 J. Molec. Biol. 273: 927-948). These and other approaches may be employed in combination.

A monoclonal antibody herein may mean an antibody obtained from a population of essentially uniform antibodies. In other words, individual antibodies contained in the population is identical except for natural mutants that may possibly be present in small amounts. Monoclonal antibodies are against single antigenic sites, and are very specific. Further, in contrast to a typical polyclonal antibody which targets different antigens or different epitopes, each monoclonal antibody targets a single epitope of an antigen. The modifier "monoclonal" indicates the property of an antibody obtained from an essentially uniform antibody population, and is not to be understood in a limited way as requiring the production of the antibody by a particular method.

The anti-EphA4 antibody according to the present disclosure may be a mouse antibody, a chimeric antibody, or a humanized antibody. A chimeric antibody is e.g. an antibody where the variable region of a non-human (such as a mouse or a rat) antibody is fused with the constant region of a human antibody, and for example may refer to an antibody where the variable region is derived from a non-human antibody and the constant region is derived from a human antibody. A humanized antibody is e.g. an antibody where a complementarity-determining region (CDR (may also be referred to as a hypervariable region)) of a non-human antibody is introduced into a human antibody, and for example may refer to an antibody where the CDR is derived from a non-human antibody and the remaining regions of the antibody are derived from a human antibody. Note that the borderline between a chimeric antibody and a humanized antibody does not necessarily need to be clear, and an antibody may be in a state that may be called a chimeric antibody or a humanized antibody. Moreover, in a chimeric antibody or a humanized antibody, the antibody region derived from a human antibody (FR, constant region) does not necessarily need to be all composed of amino acids derived from a human antibody, and may comprise one or multiple amino acids derived from a non-human antibody, as long as it can be used normally in a human subject. One embodiment of a humanized antibody is an antibody where the CDR is derived from a rodent antibody and the remaining regions of the antibody are derived from a human antibody. A particular embodiment of a humanized antibody is an antibody where the CDR is derived from a mouse antibody and the remaining regions of the antibody are derived from a human antibody. In these embodiments, the CDR may comprise one or multiple amino acids derived from a non-rodent antibody or one or multiple amino acids derived from a non-mouse antibody, and the antibody regions other than the CDR may comprise one or multiple amino acids derived from a non-human antibody. Here, "multiple" is, but it not limited to, 2-20, or 2-15, such as 14, 13, 12, 11, 10, 9, 8, 7, 6, 5, 4, 3, or 2, or within 10%, within 9%, within 8%, within 7%, within 6%, within 5%, within 4%, within 3%, within 2%, or within 1% of the number of amino acids in an amino acid sequence. Humanization can be performed with a CDR transplantation method (Kontermann and Dubel, Antibody Engineering, Springer Lab Manual (2001) and Tsurushita et al., Methods 36: 69-83 (2005)), and further may also be performed by substituting the CDR sequence with a corresponding sequence in the human antibody with methods well-known in the pertaining technical field (see e.g. Jones et al., Nature 321: 522-525 (1986); Riechmann et al., Nature 332: 323-327 (1988); and Verhoeyen et al., Science 239: 1534-1536 (1988)).

In order to decrease antigenicity, it may be important to select the use of human variable regions in both light and heavy chains upon preparation of the humanized antibody. According to the "best-fit" method, the variable region sequence of the rodent antibody is screened against the entire library of known human FR sequences. Following that, a human sequence that is the closest to the rodent sequence is accepted as the human FR of the humanized antibody. See e.g. Sims et al., J. Immunol. 151: 2296-2308

(1993) and Chothia et al., J. Mol. Biol. 196: 901-917 (1987). In another method, a particular framework derived from a sequence common in all human antibodies of a particular subgroup of the light or heavy chain is employed. The same framework may be employed for several different humanized antibodies. See e.g. Carter et al., Proc. Natl. Acad. Set USA 89: 4285-4289 (1992) and Presta et al., J. Immunol. 151: 2623-2632 (1993).

Further, in general, it is desirable that the humanized antibody retains the high binding affinity towards the antigen and other preferred biological properties. To this end, according to one method, humanized antibodies are prepared by an analysis step of the parent sequence and various conceptual humanized products employing three-dimensional models of the parent and humanized sequences. In general, three-dimensional immunoglobulin models are available and known to those skilled in the art. Computer programs that illustrate and present promising three-dimensional conformations of selected candidate immunoglobulin sequences are available. Investigation of these presentations will allow analysis of possible roles of residues in the functions of candidate immunoglobulin sequences, i.e. analysis of residues that influence the ability of candidate immunoglobulins to bind to their antigens. With this method, FR residues can be selected from recipient and imported sequences and used in combination so that desirable antibody properties such as increase in the binding affinity to single or multiple target antigen(s) (such as EphA4 or a fragment thereof) are accomplished.

Needless to say, an antibody with appropriate alteration (such as modification of the antibody, or partial substitution, addition and/or deletion of the amino acid sequence of the antibody) in the chimeric or humanized antibody exemplified above while retaining the function of the antibody (or in order to add or improve the function of the antibody) is also encompassed in the anti-EphA4 antibody according to the present disclosure. More specifically, an antibody having alteration in the amino acid sequence of the constant region in order to modify the effector function of the antibody is also included in the scope of the present disclosure. For example, an antibody having valine (Val) at position 234 (Eu numbering) of human IgG$_2$ antibody substituted to alanine (Ala) and having glycine (Gly) at position 237 substituted to alanine (Ala) in order to reduce antibody-dependent cellular cytotoxicity (ADCC) activity and/or antibody-dependent cellular phagocytosis (ADCP) activity etc. is also included in the scope of the present disclosure. Further, a bispecific antibody that has an antibody binding site having the CDR sequence of the anti-EphA4 antibody according to the present disclosure together with an antigen binding site that binds to a different antigen (Kontermann (2012), mAbs 4, 182-97) is also included in the scope of the present disclosure.

The anti-EphA4 antibody according to the present disclosure may be modified as desired. Modification of the anti-EphA4 antibody may be a modification that changes (a) the three-dimensional structure of the amino acid sequence in the region to be modified, such as sheet or helix conformation etc.; (b) the charge or hydrophobic state of the molecule at the target site; or (c) the effect of the modification on the maintenance of the side chain volume, or may be a modification in which these changes are not clearly observed.

Modification of the anti-EphA4 antibody according to the present disclosure may be accomplished by e.g. substitution, deletion, addition, and the like of the constituent amino acid residues.

An amino acid herein is employed in its broadest meaning, and includes not only natural amino acids, such as serine (Ser), asparagine (Asn), valine (Val), leucine (Leu), isoleucine (Ile), alanine (Ala), tyrosine (Tyr), glycine (Gly), lysine (Lys), arginine (Arg), histidine (His), aspartic acid (Asp), glutamic acid (Glu), glutamine (Gln), threonine (Thr), cysteine (Cys), methionine (Met), phenylalanine (Phe), tryptophan (Trp), and proline (Pro), but also non-natural amino acids such as amino acid variants and derivatives. Those skilled in the art will naturally understand in light of this broad definition that e.g. L-amino acids; D-amino acids; chemical modified amino acids such as amino acid variants and amino acid derivatives; amino acids that will not be protein components in the body such as norleucine, β-alanine, and ornithine; and chemically synthesized compounds having amino acid properties well-known to those skilled in the art, and the like are included as the amino acids of the present specification. Examples of a non-natural amino acid can include, e.g., α-methylamino acids (such as α-methylalanine), D-amino acids (such as D-aspartic acid and D-glutamic acid), histidine-like amino acids (such as 2-aminohistidine, β-hydroxy-histidine, homohistidine, α-fluoromethyl-histidine, and α-methyl-histidine), amino acids having excess methylene on the side chain ("homo" amino acid), and amino acids where the carboxylate functional group amino acid in the side chain is substituted with a sulfonate group (such as cysteic acid).

Naturally-occurring amino acid residues may be classified into e.g. groups below based on general side chain properties:

(1) Hydrophobic: Met, Ala, Val, Leu, Ile;
(2) Neutral hydrophilic: Asn, Gln, Cys, Ser, Thr;
(3) Acidic: Asp, Glu;
(4) Basic: His, Lys, Arg;
(5) Residues that influence chain orientation: Gly, Pro; and
(6) Aromatic: Trp, Tyr, Phe.

Nonconservative substitution of the amino acid sequence constituting the antibody may be performed by exchanging an amino acid belonging to one of these groups with an amino acid belonging to another group. A more conservative substitution may be performed by exchanging an amino acid belonging to one of these groups with another amino acid in the same group. Similarly, deletion or substitution of the amino acid sequence may be appropriately performed.

Modification of amino acids configuring the antibody may be e.g. glycosylation by a carbohydrate or post-translational modifications such as acetylation or phosphorylation. The antibody may be glycosylated at a conserved position in its constant region. Glycosylation of an antibody is ordinarily either N-linked or O-linked. N-linked means the binding of a carbohydrate portion to the side chain of an asparagine residue. Tripeptide sequences asparagine-X-serine, asparagine-X-threonine, and asparagine-X-cysteine (wherein X is any amino acid other than proline) are recognition sequences for enzymatically adding the carbohydrate portion to the asparagine side chain. When one of these tripeptide sequences is present in the antibody, a potential glycosylation site is present. O-linked glycosylation may be the binding of either N-acetylgalactosamine, galactose, or xylose to a hydroxy amino acid (such as serine or threonine), and in some instances may be the binding to 5-hydroxyproline or 5-hydroxylysine. Those skilled in the art can appropriately select the glycosylation condition (such as the type of host cell or cell medium and pH etc., when glycosylation is performed with a biological means) according to the objective.

The anti-EphA4 antibody according to the present disclosure may further be modified by other modification methods, alone or in combination, based on common technical knowledge well-known to those skilled in the art.

The anti-EphA4 antibody according to the present disclosure can be produced by a method well-known to those skilled in the art. For example, the antibody may be produced by integrating the nucleic acid encoding the anti-EphA4 antibody according to the present disclosure into an expression vector, introducing the expression vector into a host cell, and culturing the host cell. Accordingly, the present disclosure encompasses a nucleic acid encoding the anti-EphA4 antibody, a vector that comprises the nucleic acid, a host cell comprising the vector, and a method of producing the anti-EphA4 antibody comprising a step of culturing the host cell.

The nucleic acid encoding the anti-EphA4 antibody according to the present disclosure may have DNA encoding a signal sequence, or may have DNA encoding a signal sequence at the 5' terminal of the DNA encoding the heavy chain variable region and the DNA encoding the light chain variable region. A signal sequence is amino acid residues present at the N-terminal of the protein that is necessary for a secretory protein or an integral membrane protein to pass through the lipid bilayer after being synthesized on a ribosome, and in the present disclosure, is not particularly limited as long as it is a sequence having this function. Signal sequences that may be contained in the anti-EphA4 antibody according to the present disclosure include signal sequences derived from human, mouse, rat, rabbit, donkey, goat, horse, bird, dog, cat, yeast, and the like. Specifically, in the present disclosure, a peptide comprising an amino acid sequence represented by SEQ ID NO. 12 or 16 can be included as a signal sequence related to the heavy chain, and a peptide comprising an amino acid sequence represented by SEQ ID NO. 14 or 18 can be included as a signal sequence related to the light chain. Moreover, as long as it is functionally equivalent, the signal sequence may have substitution, addition, and/or deletion of one or multiple (such as 2, 3, 4, or 5) amino acids in the amino acid sequence represented by SEQ ID NO. 12 or 16 and the amino acid sequence represented by SEQ ID NO. 14 or 18.

The anti-EphA4 antibody according to the present disclosure may be that isolated or purified according to a method well-known to those skilled in the art.

"Isolated" or "purified" herein means artificially isolated or purified from the natural state. If the molecule or composition is naturally occurring, it is "isolated" or "purified" when it is changed or removed from the original environment, or both. Examples of an isolation or purification method include, but are not limited to, means by electrophoresis, molecular biology, immunology, or chromatography, and the like, specifically, ion exchange chromatography, hydrophobic chromatography, reverse phase HPLC chromatography, isoelectric focusing, or alkali extraction method, and the like.

In one embodiment, the anti-EphA4 antibody comprises the following CDRs:
(a) a heavy chain CDR1 consisting of the amino acid sequence shown in SEQ ID NO. 44;
(b) a heavy chain CDR2 consisting of the amino acid sequence shown in SEQ ID NO. 27;
(c) a heavy chain CDR3 consisting of the amino acid sequence shown in SEQ ID NO. 28;
(d) a light chain CDR1 consisting of the amino acid sequence shown in SEQ ID NO. 29;
(e) a light chain CDR2 consisting of the amino acid sequence shown in SEQ ID NO. 30; and
(f) a light chain CDR3 consisting of the amino acid sequence shown in SEQ ID NO. 31.

In one embodiment, the anti-EphA4 antibody is a humanized antibody or a chimeric antibody, and in a particular embodiment a humanized antibody.

In another embodiment, the anti-EphA4 antibody comprises heavy and light chains, the variable region of the heavy chain comprises the amino acid sequence shown in SEQ ID NO. 45, and the variable region of the light chain comprises the amino acid sequence shown in SEQ ID NO. 46. Note that in the embodiment, the variable region of the heavy chain and/or the variable region of the light chain may comprise an amino acid sequence having one or multiple aminoacids substituted, added, and/or deleted in the amino acid sequence shown in SEQ ID NO. 45 and/or the amino acid sequence shown in SEQ ID NO. 46. Here, "multiple" is not limited as long as it retains the binding affinity towards EphA4 and enhances the cleavage of EphA4, and is 2-15, or 2-10, such as 9, 8, 7, 6, 5, 4, 3, or 2, or within 10%, such as within 9%, within 8%, within 7%, within 6%, within 5%, within 4%, within 3%, within 2%, or within 1% of the number of amino acids in an amino acid sequence.

In one embodiment, the heavy chain of the anti-EphA4 antibody comprises the constant region of human $IgG_2$.

In a particular embodiment, the constant region of human $IgG_2$ comprises the amino acid sequence of SEQ ID NO. 47.

In one embodiment, the light chain of the anti-EphA4 antibody comprises the constant region of human IgK.

In a particular embodiment, the constant region of human Igκ comprises the amino acid sequence of SEQ ID NO. 48.

In one embodiment, the anti-EphA4 antibody comprises a heavy chain comprising the amino acid sequence shown in SEQ ID NO. 59 and a light chain comprising the amino acid sequence shown in SEQ ID NO. 60.

In another embodiment, for example, for reasons such as decreasing the ununiformity of antibodies produced by antibody-producing cells (U.S. Patent Application Publicaion No. 2010/0297697 or Liu H et al., MAbs. 2014 September-October; 6 (5): 1145-1154), the anti-EphA4 antibody has lysine positioned at the C-terminal (carboxy terminal) of the heavy chain deleted. In the present disclosure, an anti-EphA4 antibody having the C-terminal lysine of the heavy chain deleted also includes an anti-EphA4 antibody having the C-terminal lysine of the heavy chain deleted by genetic modification or an anti-EphA4 antibody having the C-terminal lysine of the heavy chain cleaved post-translationally by carboxypeptidase etc., and the like. Moreover, in the present disclosure, an anti-EphA4 antibody having the C-terminal lysine of the heavy chain deleted includes not only an anti-EphA4 antibody having the C-terminal lysine deleted in both heavy chains, but also an anti-EphA4 antibody having the C-terminal lysine deleted in only one heavy chain.

In one aspect, the present disclosure relates to an isolated nucleic acid encoding an anti-EphA4 antibody. An isolated nucleic acid encoding an anti-EphA4 antibody refers to one or more nucleic acid molecules encoding the heavy chain and/or light chain of an anti-EphA4 antibody. In one embodiment, the nucleic acid according to the present disclosure encodes the heavy chain of the anti-EphA4 antibody. In another embodiment, the nucleic acid according to the present disclosure encodes the light chain of the anti-EphA4 antibody. In another further embodiment, the nucleic acid according to the present disclosure encodes the heavy and light chains of the anti-EphA4 antibody. The nucleic acid according to the present disclosure also includes a first nucleic acid molecule encoding the heavy chain of the anti-EphA4 antibody and a second nucleic acid molecule encoding the light chain of the anti-EphA4 antibody.

In another aspect, the present disclosure relates to a vector comprising the isolated nucleic acid encoding the anti-EphA4 antibody. The vector according to the present disclosure refers to one or more vectors comprising the isolated nucleic acid encoding the anti-EphA4 antibody. In one embodiment, the vector according to the present disclosure is a vector comprising the nucleic acid encoding the heavy chain of the anti-EphA4 antibody and the nucleic acid encoding the light chain of the anti-EphA4 antibody. In another embodiment, the vector according to the present disclosure is a vector comprising the nucleic acid encoding the heavy and light chains of the anti-EphA4 antibody. In another further embodiment, the vector according to the present disclosure comprises a first vector comprising the nucleic acid encoding the heavy chain of the anti-EphA4 antibody and a second vector comprising the nucleic acid encoding the light chain of the anti-EphA4 antibody. The vector according to the present disclosure may be, but not limited to, a plasmid, a cosmid, a virus, a phage, and the like. For example, as a viral vector, retroviral, lentiviral, adenoviral, adeno-associated viral, or herpes simplex viral vector, and the like are also included in the vector according to the present disclosure.

In yet another aspect, a host cell comprising the vector according to the present disclosure, and a method of producing an anti-EphA4 antibody comprising a step of culturing the host cell are also included in the present disclosure. The host cell according to the present disclosure may be, but not limited to, *E. coli* cells, monkey COS cells, Chinese hamster ovary (CHO) cells, NS0 cells, and the like. In one embodiment, the method of producing an anti-EphA4 antibody comprises a step of culturing the host cell, and a step of recovering the anti-EphA4 antibody secreted from the host cell (or culture medium of host cell).

In one aspect, the present disclosure relates to a pharmaceutical composition comprising an anti-EphA4 antibody. The pharmaceutical composition according to the present disclosure can be manufactured according to known methods such as methods described in the Pharmacopeia of Japan (JP), the United States Pharmacopeia (USP), or the European Pharmacopeia (EP), and the like.

The anti-EphA4 antibody according to the present disclosure may be useful for treating Alzheimer's disease. In other words, in other aspects, the present disclosure encompasses a method for treating Alzheimer's disease comprising a step of administering a therapeutically effective amount of an anti-EphA4 antibody to a subject having Alzheimer's disease. Moreover, in other aspects, the present disclosure encompasses the use of an anti-EphA4 antibody for manufacturing a therapeutic drug for Alzheimer's disease. In other aspects, the present disclosure encompasses an anti-EphA4 antibody for use in the treatment of Alzheimer's disease.

The anti-EphA4 antibody according to the present disclosure may be useful for treating tauopathy. In other words, in other aspects, the present disclosure encompasses a method for treating tauopathy comprising a step of administering a therapeutically effective amount of an anti-EphA4 antibody to a subject having tauopathy. Moreover, in other aspects, the present disclosure encompasses the use of an anti-EphA4 antibody for manufacturing a therapeutic drug for tauopathy. In other aspects, the present disclosure encompasses an anti-EphA4 antibody for use in the treatment of tauopathy. Tauopathy of the present disclosure includes Alzheimer's disease or frontotemporal lobar degeneration with tau pathology (FTLD-tau). Moreover, frontotemporal lobar degeneration with tau pathology includes progressive supranuclear palsy (PSP), corticobasal degeneration (CBD), argyrophilic grain dementia (AGD), senile dementia of the neurofibrillary tangle type (SD-NFT), Pick's disease (PiD), and the like.

The anti-EphA4 antibody according to the present disclosure can be employed in the therapeutic method alone or in combination with other agents or compositions. For example, the anti-EphA4 antibody according to the present disclosure may be administered at the same or different times as another agent. Such combination therapy includes combination administration (two or more agents are included in the same or separate formulation) and separate administration (such as simultaneous or sequential). When two or more agents are separately administered, the administration of the anti-EphA4 antibody according to the present disclosure may be performed before or after the accompanying therapeutic method.

The subject for administering the pharmaceutical composition according to the present disclosure is not limited, and can be employed for e.g. a human or non-human mammal (such as monkey, mouse, rat, rabbit, cow, horse, and goat).

The method of administering the pharmaceutical composition according to the present disclosure to a subject (such as administration route, dosage, the number of administrations per day, and administration timing) is not limited, and can be appropriately decided by those skilled in the art (such as a physician) according to the health state of the subject, the extent of the disease, the type of agents used in combination, and the like.

Those skilled in the art shall recognize that as long as it is not technically contradicting, the present invention may be carried out in an appropriate combination of any one or more of any and all aspects described herein. Further, those skilled in the art shall recognize that as long as it is not technically contradicting, it is preferred that the present invention is carried out in an appropriate combination of any and all preferred or advantageous aspects described herein.

All of the disclosures of the literatures cited herein shall be regarded as clearly cited herein by reference, and those skilled in the art can understand the related disclosure contents in these literatures by citing them as a part of the present specification according to the context herein without departing from the spirit and scope of the present invention.

The literatures cited herein are provided with the sole purpose of disclosing the related technology preceding the filing date of the present application, and are not to be construed as an admission by the present inventors that the present invention does not hold the right to precede said disclosures due to prior inventions or for any other reason. All of the description of all these literatures is based on the information available to the present applicants, and does not configure in any way an acknowledgement that these description contents are accurate.

The terms used herein are employed for describing particular embodiments, and do not intend to limit the invention.

The term "comprise" as used herein, unless the content clearly indicates to be understood otherwise, intends the presence of the described items (such as components, steps, elements, or numbers), and does not exclude the presence of other items (such as components, steps, elements, and numbers). The term "consist of" encompasses the aspects described by the terms "consist of" and/or "consist essentially of."

The term "neutralizing activity" as used herein means the activity to inhibit the binding between EphA4 and a ligand thereof, and/or the activity to inhibit signal transduction or molecular expression response or functionality change of cells which are induced by EphA4 due to binding to a ligand thereof in the human body.

Unless otherwise defined, all terms used herein (including technical and scientific terms) have the same meanings as those broadly recognized by those skilled in the art of the technology to which the present invention belongs. The terms used herein, unless explicitly defined otherwise, are to be construed as having meanings consistent with the meanings herein and in related technical fields, and shall not be construed as having idealized or excessively formal meanings.

Terms such as first and second are employed to express various elements, and it should be recognized that these elements are not to be limited by these terms per se. These terms are employed solely for the purpose of discriminating one element from another, and it is for example possible to describe a first element as a second element, and similarly, to describe a second element as a first element without departing from the scope of the present invention.

The numeric values employed herein for indicating component content or numeric value range and the like, unless explicitly indicated, are to be understood as being modified by the term "about." For example, "4° C.," unless explicitly indicated, is understood to mean "about 4° C.," and it is obvious that those skilled in the art can rationally understand the extent thereof in concordance with technical common sense and the meaning of the passages herein.

It should be recognized that unless clearly indicated to mean otherwise in context, when used in the specification and the claims herein, each aspect represented in singular form may also be a plural form as long as it is not technically contradicting, and vice versa.

The present invention will now be described in further detail with reference to Examples. However, the present invention can be embodied by various aspects, and shall not be construed as being limited to the Examples described herein. Those skilled in the art of related technical fields will be able to carry out the present invention with various modifications, additions, deletions, substitutions, and the like without altering the spirit or scope of the present invention.

EXAMPLES

Reference Example 1: Preparation of Anti-EphA4 Monoclonal Antibody (A) Preparation of Mouse Anti-EphA4 Monoclonal Antibody In order to prepare a monoclonal antibody that binds to mouse EphA4 (Genbank Accession No. NP_031962.2, SEQ ID NO. 1), a protein having secretory alkaline phosphatase (SEAP) and histidine tag fused to the extracellular region of mouse EphA4 (positions 20-547) (SEQ ID NO. 2) (hereinafter referred to as "mouse EphA4 extracellular region-SEAP-His protein," SEQ ID NO. 3) was prepared by the following steps.

First, the DNA sequences encoding the signal sequence (SEQ ID NO. 4) and the extracellular region (SEQ ID NO. 2) of mouse EphA4 were amplified by RT-PCR with total RNA derived from mouse brain, and cloned into the Sal I/Not I site of pENTR1A vector (Invitrogen/LifeTechnologies) having the DNA sequence encoding SEAP and histidine tag. Next, the DNA sequence encoding the signal sequence and extracellular region of mouse EphA4, SEAP, and histidine tag was transferred to pcDNA3.1_rfcB vector by LR reaction of Gateway System (Invitrogen/LifeTechnologies) to construct pcDNA 3.1-mouse EphA4 extracellular region-SEAP-His expression vector. The constructed pcDNA 3.1-mouse EphA4 extracellular region-SEAP-His expression vector was transfected into HEK293 EBNA cells (Invitrogen/LifeTechnologies) with TransIT-LT1 (TAKARA). After 6 days of incubation (5% $CO_2$, 37° C.), the culture supernatant was recovered. From the recovered culture supernatant, mouse EphA4 extracellular region-SEAP-His protein (SEQ ID NO. 3) was purified with Protino column (MACHEREY-NAGEL).

Twenty micrograms of mouse EphA4 extracellular region-SEAP-His protein was mixed with the same amount of TiterMax Gold adjuvant (TiterMax USA) or GERBU adjuvant (GERBU Biotechnik GmbH), and subcutaneously injected into the footpad of Balb/c mice. Mouse EphA4 extracellular region-SEAP-His protein was then similarly administered on Days 3, 7, and 10. Here, TiterMax Gold adjuvant (TiterMax USA) was used only on Day 10, and GERBU adjuvant (GERBU Biotechnik GmbH) was used on Days 3, 7, and 10. Mice were sacrificed on Day 13, and peripheral lymph nodes were recovered to prepare lymph node cells. The prepared lymph node cells and P3U1 myeloma cells (endowed from Kyoto University) were fused at a proportion of 5:1 in the presence of GenomeONE-CF (Ishihara Sangyo Kaisha, Ltd.). The fused cells were cultured in a 96-well plastic plate. After 7 days of incubation (5% $CO_2$, 37° C.), the culture supernatant was recovered.

Employing the culture supernatant obtained, wells having reactivity against mouse, rat, and human EphA4 were picked up.

Reactivity against mouse, rat, and human EphA4 was evaluated with ELISA with proteins having the Fc region of human $IgG_1$ and histidine tag fused to the extracellular region of mouse EphA4, the extracellular region (positions 20-547) of rat EphA4 (Genbank Accession No. NP_001155883.1), or the extracellular region (positions 20-547) (SEQ ID NO. 6) of human EphA4 (Genbank Accession No. NP_004429.1, SEQ ID NO. 5) (hereinafter referred to "mouse EphA4 extracellular region-Fc-His protein," "rat EphA4 extracellular region-Fc-His protein," or "human EphA4 extracellular region-Fc-His protein," respectively).

Mouse, rat, or human EphA4 extracellular region-Fc-His proteins were prepared by the following steps. Initially, pcDNA 3.1-mouse, rat, or human EphA4 extracellular region-Fc-His expression vectors were constructed. First, the DNA sequences encoding the signal sequence and the extracellular region of mouse, rat, or human EphA4 were amplified by RT-PCR with total RNA derived from mouse, rat, or human brain, and cloned into the Sal I/Not I site of pENTR1A vector (Invitrogen/LifeTechnologies) having the DNA sequence encoding Fc and histidine tag. Next, the DNA sequences encoding the signal sequence and extracellular region of mouse, rat, or human EphA4, Fc, and histidine tag were transferred to pcDNA 3.1_rfcB vector by LR reaction of Gateway System (Invitrogen/LifeTechnologies) to construct pcDNA 3.1-mouse, rat, or human EphA4 extracellular region-Fc-His expression vectors. These expression vectors constructed were transfected into HEK293 EBNA cells (Invitrogen/LifeTechnologies) with TransIT-LT1 (TAKARA). After 6 days of incubation (5% $CO_2$, 37° C.), the culture supernatant was recovered.

ELISA employing mouse, rat, or human EphA4 extracellular region-Fc-His proteins was performed following the steps below. Anti-human IgG antibody (Jackson ImmunoResearch Laboratories) was coated onto the wells of a 96-well plate (Nunc). After incubating at 4° C. overnight, wells were blocked at room temperature for one hour with 1× Block ACE (Dainippon Seiyaku). After washing three times with 0.02 Tween 20/PBS (Nacalai Tesque), a culture supernatant comprising mouse, rat, or human EphA4 extracellular region-Fc-His protein was added to each well (final concentration 1 nM), and this was incubated at room temperature for one hour. After washing three times, the culture supernatant of the fused cells was added to each well. After incubating at room temperature for one hour and washing three times, horseradish peroxidase-labeled anti-mouse IgG antibody (Jackson ImmunoResearch Laboratories) was added, and this was incubated at room temperature for one hour. After washing three times, TMBZ (3,3',5,5'-tetramethylbenzidine, Sigma) solution was added to each well, and this was incubated at room temperature for 5-20 minutes. An equal amount of the stop solution (2 N $H_2SO_4$, Wako Pure Chemical) was added to each well, and absorbance at 450 nm was read with a microplate reader (PerkinElmer).

Hybridomas were cloned from the wells picked up through the above steps by limiting dilution method, and hybridoma clones expressing mouse anti-EphA4 antibody having binding activity against mouse, rat, and human EphA4 was ultimately obtained.

The hybridoma clones obtained were cultured, and mouse anti-EphA4 monoclonal antibody was purified from the culture supernatant with Protein A (GE Healthcare).

(B) Evaluation of EphA4 Cleavage Enhancement Activity

Preparation of rat hippocampus neurons was performed following the steps below. Fetuses were taken out of a rat at Day 18 of pregnancy (Charles River Laboratories Japan), and the head was cut open to take out the brain. The hippocampus region was cut out under a stereomicroscope, placed in the digestion solution (137 mM NaCl (Wako Pure Chemical), 5 mM KCl (Wako Pure Chemical), 7 mM $Na_2HPO_4$ (Wako Pure Chemical), 25 mM Hepes (DOJINDO), 0.5 mg/mL DNase (Sigma), and 0.25% trypsin (Life technologies)), and shaken at 37° C. for 10 minutes. The solution was removed, and 20% Fetal bovine serum/Hanks buffer (Sigma) was added. After removing the solution and washing twice in Hanks buffer, the hippocampus tissue was pipetted in Hanks buffer to prepare a cell suspension. Cells were seeded in a 96-well dish (Falcon) coated with poly-L-lysine containing culture fluid (Neurobasal medium (Life technologies), 1×B-27 supplement (Life technologies), and 0.5 mM L-glutamine (Life technologies)).

Evaluation of EphA4 cleavage enhancement activity employing hippocampus neurons was performed following the steps below. Rat hippocampus neurons seeded in a 96-well dish (Falcon) were treated with anti-EphA4 monoclonal antibody (67 nM) and γ selectase inhibitory drug Compound E (50 nM, Enzo Life Sciences). Sixteen hours later, this was washed with PBS (Wako Pure Chemical), SDS sample buffer (Laemmli sample buffer (Bio-Rad) and 5% 2-mercaptoethanol (Bio-Rad)) was added to recover the cells, and this was boiled for 5 minutes. SDS-PAGE was performed with this sample, western blotting with anti-EphA4 monoclonal antibody (Abnova) was performed, the band strength was quantified, and the value of EphA4 C-terminal fragment/full length EphA4 was calculated.

Mouse anti-EphA4 monoclonal antibody having activity that enhances the cleavage of EphA4 (antibody A) was obtained. The isotype of antibody A was determined with monoclonal antibody isotyping kit (Serotec) to be $IgG_1$ for the heavy chain and κ for the light chain.

(C) Sequence Analysis of Antibody A

The DNA sequence encoding the signal sequence and the variable region of heavy and light chains of antibody A was amplified by 5'-RACE (5'-rapid amplification of cDNA ends) method. Total RNA was prepared from the hybridoma with RNeasy (QIAGEN), and treated with DNase (QIAGEN, RNase free DNase set). Double-stranded cDNA was prepared from the total RNA with cDNA synthesis kit (TAKARA). 5' Adaptor obtained by annealing of oligoDNA ad29S (ACATCACTCCGT) (SEQ ID NO. 7) and oligoDNA ad29AS (ACGGAGTGATGTCCGTCGACGTATCTCTGCGTTGATACTTCAGCGTAGCT) (SEQ ID NO. 8) was added to the cDNA. The cDNA obtained was amplified with 5' forward primer (5'-PCR4 primer, AGCTACGCTGAAGTATCAACGCAGAG) (SEQ ID NO. 9) and 3' reverse primer (GCCAGTGGATAGACTGATGG (SEQ ID NO. 10) was employed for amplification of the mouse IgG heavy chain, and GATGGATACAGTTGGTGCAGC (SEQ ID NO. 11) was employed for amplification of the mouse Igκ light chain). The amplified cDNA was inserted into pCR2.1 vector (Invitrogen/LifeTechnologies). The gene sequence of antibody A was analyzed with ABI 3130XL. As amino acid sequences coded by the gene sequence of antibody A identified by the present analysis, the heavy chain signal sequence is the sequence shown in SEQ ID NO. 12, the heavy chain variable region is the sequence shown in SEQ ID NO. 13, the light chain signal sequence is the sequence shown in SEQ ID NO. 14, and the light chain variable region is the sequence shown in SEQ ID NO. 15. As nucleotide sequences coding the gene sequence of antibody A, heavy chain signal sequence is the sequence shown in SEQ ID NO. 16, the heavy chain variable region is the sequence shown in SEQ ID NO. 17, the light chain signal sequence is the sequence shown in SEQ ID NO. 18, and the light chain variable region is the sequence shown in SEQ ID NO. 19.

The full length sequences of the heavy and light chains of antibody A were obtained with the following steps. Total RNA was prepared from the hybridoma with RNeasy (QIAGEN), and treated with DNase (QIAGEN, RNase free DNase set). Reverse transcription products were prepared from the total RNA with RNA PCR kit (TAKARA). Employing the reverse transcription products obtained as templates, the gene sequence encoding the heavy and light chains of antibody A was amplified with PCR with 5' forward primer (GCGAAGCTTGCCGCCACCATGGCTGTCCTGGTGCTGCTCC (primer ID 7455) (SEQ ID NO. 20) was used for amplification of the heavy chain, and GCGAAGCTTGCCGCCACCATGGACATGAGGGTTCCTGCTCACG (primer ID 7453) (SEQ ID NO. 21) was used for amplification of the light chain) and 3' reverse primer (GCGGAATTCATCATTTACCAGGAGAGTGGGAGAGGC (primer ID 7257) (SEQ ID NO. 22) was used for amplification of the heavy chain, and CGCGAATTCACTAACACTCATTCCTGTTGAAGCTCTTGAC (primer ID 7249) (SEQ ID NO. 23) was used for amplification of the light chain), and respectively cloned into pEE6.4 and pEE12.4 vectors (Lonza). The gene sequence was analyzed with ABI3130XL. As amino acid sequences coded by the gene sequence of antibody A identified by the present analysis, the heavy chain constant region is the sequence shown in SEQ ID NO. 24, and the light chain constant region is the sequence shown in SEQ ID NO. 25.

The CDR of antibody A was determined with the following method. The amino acid sequence of antibody A was numbered according to the Kabat numbering system with Abysis software (UCL). Based on this numbering, decision was made according to Kabat definition for CDR identification. The amino acid sequences of CDR of antibody A are shown in Table 1.

TABLE 1

Amino acid sequences of CDR of antibody A

| Name | Sequence |
|---|---|
| Heavy chain CDR1 | RYGVH (SEQ ID NO. 26) |
| Heavy chain CDR2 | VIWPGGSTDYNAAFMS (SEQ ID NO. 27) |
| Heavy chain CDR3 | ESLFGVYYDYGYYSMDY (SEQ ID NO. 28) |
| Light chain CDR1 | RASQEISGYLS (SEQ ID NO. 29) |
| Light chain CDR2 | AASTLDS (SEQ ID NO. 30) |
| Light chain CDR3 | LQYASYPLT (SEQ ID NO. 31) |

Reference Example 2: Binding Affinity of Anti-EphA4 Monoclonal Antibody Against Mouse and Human EphA4

The binding affinity of antibody A against mouse and human EphA4 was determined by surface plasmon resonance (SPR method) employing Biacore T200 (GE Healthcare). First, anti-His antibody (GE Healthcare, 28-9950-56) was fixed onto a sensor chip CM5. Fixation was performed by amine coupling method employing N-hydroxysuccinimide (NHS) and N-ethyl-N'-(3-dimethylaminopropyl)carbodiimide hydrochloride (EDC), and ethanolamine was employed for blocking (sensor chip and fixation reagents were all from GE Healthcare). This was diluted to 3.5 μg/mL with the fixation buffer (10 mM sodium acetate, pH 4.5), and fixed on the sensor chip according to the protocol attached to Biacore T200. Mouse or human EphA4 extracellular region-SEAP-His10 was diluted with the running buffer HBS-EP (GE Healthcare, BR-1001-88), and the solution was sent onto a flow cell for 120 seconds for capture (the captured amount about 10 RU). Subsequently, antibody A serially diluted to the range of 100, 50, 25, 12.5, 6.3, 3.2, 1.6, and 0 nM with HBS-EP was added to the sensor chip for 120 seconds, and the binding reaction curve at the time of addition (binding phase, 120 seconds) and after addition had completed (dissociation phase, 600 seconds) was sequentially observed. After the completion of each observation, 4 M $MgCl_2$ (60 seconds, Wako Pure Chemical) was added to regenerate the sensor chip. Fitting analysis by 1:1 binding model employing BIA evaluation software attached to the system was performed on the binding reaction curve obtained, and the binding affinity (KD=kd/ka) against mouse and human EphA4 was calculated.

The binding affinity of antibody A against mouse and human EphA4 (KD value) was $1.32 \times 10^{-9}$ M and $1.19 \times 10^{-9}$ M, respectively (FIG. 1). Other binding parameters against mouse and human EphA4 were almost to the same extent. Accordingly, it is thought that antibody A has the same extent of binding affinity towards mouse and human EphA4.

Reference Example 3: EphA4 Cleavage Enhancement Activity of Anti-EphA4 Monoclonal Antibody in Hippocampus Neurons For antibody A, evaluation of EphA4 cleavage enhancement activity employing hippocampus neurons was performed following the steps below. Rat hippocampus neurons seeded in a 96-well dish (Falcon) were treated with antibody A (2.0, 6.7, and 20 nM) and γ selectase inhibitory drug Compound E (50 nM, Enzo Life Sciences). Twenty-four hours later, this was washed with PBS (Wako Pure Chemical), SDS sample buffer (Laemmli sample buffer (Bio-Rad) and 5% 2-mercaptoethanol (Bio-Rad)) was added to recover the cells, and this was boiled for 5 minutes. SDS-PAGE was performed with this sample, western blotting with anti-EphA4 monoclonal antibody (Abnova) was performed, the band strength was quantified, and the value of EphA4 C-terminal fragment/full length EphA4 was calculated.

Figure 2:
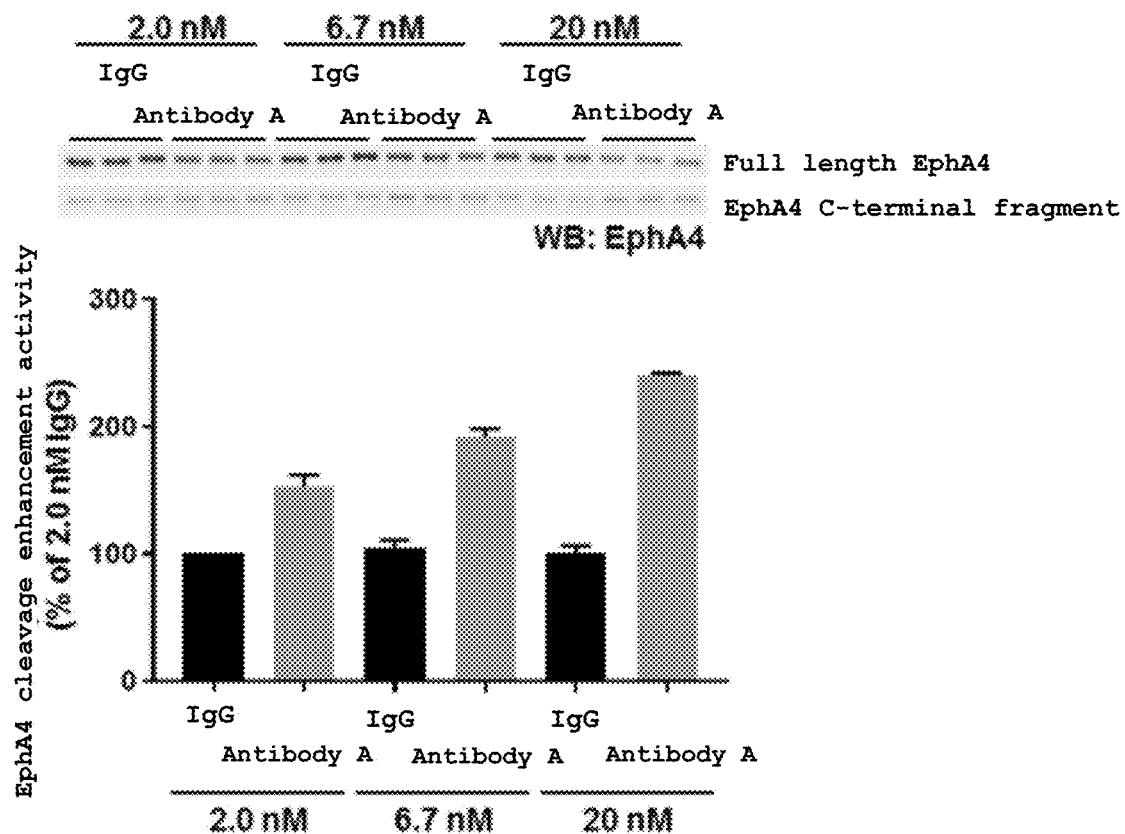
FIG. 2 shows EphA4 cleavage enhancement activity of the anti-EphA4 monoclonal antibody (antibody A) employing hippocampus neurons.

Antibody A concentration-dependently enhanced EphA4 cleavage reaction in hippocampus neurons (FIG. 2).

Reference Example 4: Mouse EphA4-Mouse Ligand Binding Inhibitory Activity of Anti-EphA4 Monoclonal Antibody For antibody A, the evaluation of the inhibitory activity of binding between mouse EphA4 and mouse ligand was performed following the steps below. Anti-alkaline phosphatase antibody (Thermo SCIENTIFIC) was coated onto the wells of a 96-well plate (Nunc). After incubating at 4° C. overnight, wells were blocked at room temperature for one hour with 1% Block ACE (DS Pharma Biomedical). After washing three times with 0.02% Tween 20/PBS (Thermo SCIENTIFIC), mouse EphA4 extracellular region-SEAP-His protein was added to the wells (final concentration 10 nM), and this was incubated at room temperature for one hour. After washing three times, the ligand and antibody A (0, 0.003, 0.01, 0.03, 0.1, 0.3, 1, 3, 10, 30, 100, 300, 1000, and 3000 nM) were added to the wells. Note that biotinylated mouse Ephrin A1-Fc chimera (R&D Systems, final concentration 6 nM) and biotinylated mouse Ephrin B2-Fc chimera (R&D Systems, final concentration 2.5 nM) were employed as ligands. After incubating at room temperature for one hour and washing three times, horseradish peroxidase-labeled streptavidin (GE Healthcare) was added, and this was incubated at room temperature for one hour. After washing three times, TMBZ (3,3',5,5'-tetramethylbenzidine, Sigma) solution was added to the wells, and this was incubated at room temperature for 2 minutes. An equal amount of the stop solution (1N $H_2SO_4$, Wako Pure Chemical) was added to the wells, and absorbance at 450 nm was read with a microplate reader (PerkinElmer).

Figure 3:
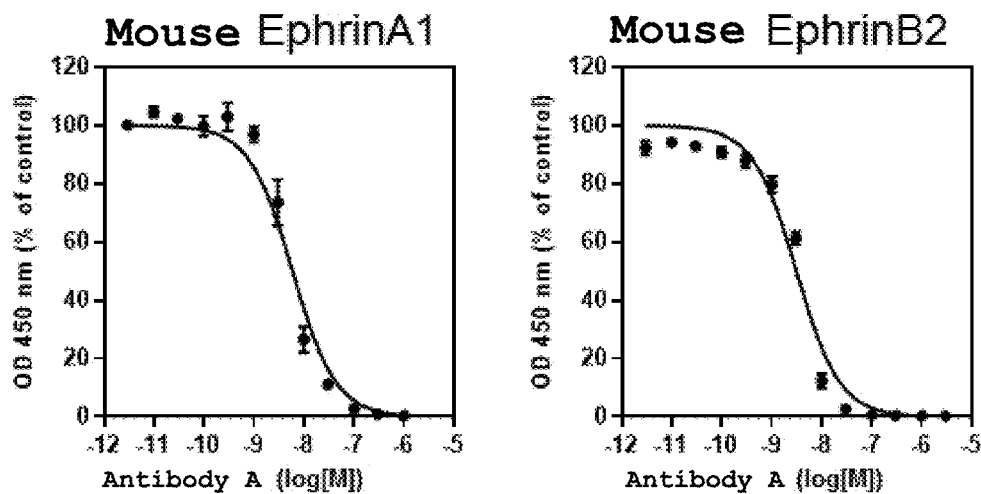
FIG. 3 shows mouse EphA4-mouse ligand binding inhibitory activity of the anti-EphA4 monoclonal antibody (antibody A).

Antibody A concentration-dependently suppressed the binding between mouse EphA4 and mouse ligand, and the $IC_{50}$ values against mouse Ephrin A1 and Ephrin B2 binding were about 5.9 nM and 3.1 nM, respectively (FIG. 3). Accordingly, it was shown that antibody A strongly inhibits the binding between mouse EphA4 and mouse ligand.

Reference Example 5: Human EphA4-Human Ligand Binding Inhibitory Activity of Anti-EphA4 Monoclonal Antibody For antibody A, the evaluation of the inhibitory activity of binding between human EphA4 and human ligand was performed following the steps below. Anti-alkaline phosphatase antibody (Thermo SCIENTIFIC) was coated onto the wells of a 96-well plate (Nunc). After incubating at 4° C. overnight, wells were blocked at room temperature for one hour with 1% Block ACE (DS Pharma Biomedical). After washing three times with 0.05% Tween 20/PBS (Thermo SCIENTIFIC), human EphA4 extracellular region-SEAP-His protein was added to the wells (final concentration 10 nM), and this was incubated at room temperature for one hour. After washing three times, the ligand and serially diluted antibody A (0, 0.003, 0.01, 0.03, 0.1, 0.3, 1, 3, 10, 30, 100, 300, 1000, and 3000 nM) were added to the wells. Note that biotinylated human Ephrin A5-Fc chimera (R&D Systems, final concentration 0.7 nM) and biotinylated human Ephrin B3-Fc chimera (R&D Systems, final concentration 2.3 nM) were employed as ligands. After incubating at room temperature for one hour and washing three times, horseradish peroxidase-labeled streptavidin (GE Healthcare) was added, and this was incubated at room temperature for one hour. After washing three times, TMBZ (3,3',5,5'-tetramethylbenzidine, Sigma) solution was added to the wells, and this was incubated at room temperature for 2-5 minutes. An equal amount of the stop solution (1N $H_2SO_4$, Wako Pure Chemical) was added to the wells, and absorbance at 450 nm was read with a microplate reader (Molecular Devices or PerkinElmer).

Figure 4:
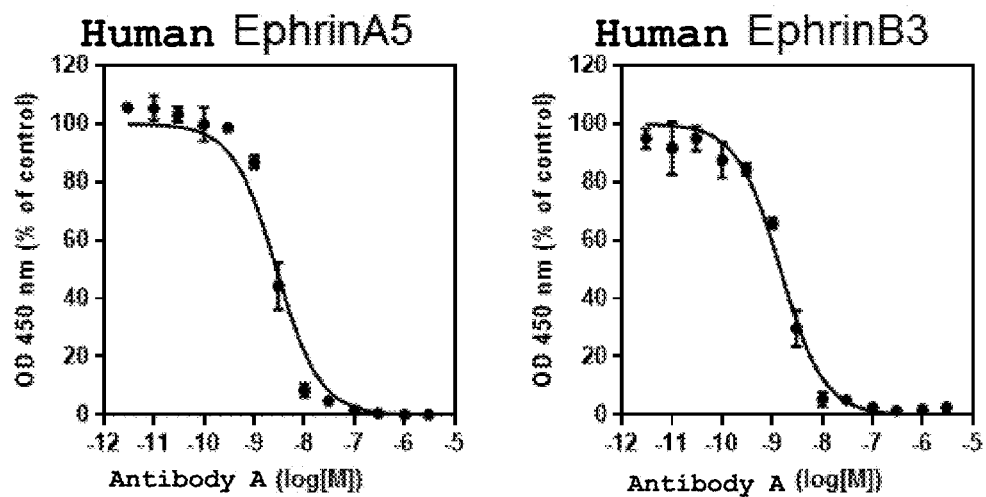
FIG. 4 shows human EphA4-human ligand binding inhibitory activity of the anti-EphA4 monoclonal antibody (antibody A).

Antibody A concentration-dependently suppressed the binding between human EphA4 and human ligand, and the $IC_{50}$ values against human Ephrin A5 and Ephrin B3 binding were about 2.8 nM and 1.4 nM, respectively (FIG. 4). Accordingly, it was shown that antibody A also strongly inhibits the binding between human EphA4 and human ligand.

Reference Example 6: Selectivity of Anti-EphA4 Monoclonal Antibody Against Human Eph Receptor Following the method for preparing mouse EphA4 extracellular region-SEAP-His protein described in Reference Example 1, the DNA sequences encoding the signal sequence and the extracellular region of each Eph receptor of human (EphA1, EphA2, EphA3, EphA4, EphA5, EphA6, EphA7, EphA8, EphA10, EphB1, EphB2, EphB3, EphB4, and EphB6) were amplified by RT-PCR with total RNA derived from tissue, and cloned into pENTR1A vector (Invitrogen/LifeTechnologies) having the DNA sequence encoding SEAP and histidine tag. Next, the DNA sequences encoding the signal sequence and extracellular region of each Eph receptor of human, SEAP, and histidine tag were transferred to pcDNA 3.1_rfcB vector by LR reaction of Gateway System (Invitrogen/LifeTechnologies) to construct vectors (referred to as "Eph receptor extracellular region-SEAP-His protein expression vector") expressing a protein having SEAP and His tag fused to the extracellular region of each Eph receptor of human (referred to as "Eph receptor extracellular region-SEAP-His protein.")

Next, each Eph receptor extracellular region of human-SEAP-His protein expression vector was introduced into Expi293F cells (Gibco/ThermoFisher) with Expi293 expression system (Gibco/ThermoFisher). After 5 days of culture (5% CO2, 37° C., 120 rpm), the culture supernatant was recovered, and this was centrifuged at room temperature, at 1500 rpm, and for 5 minutes. The centrifuged supernatant was filtered with a 0.45 µm filter (Millipore).

For antibody A, the evaluation of the binding activity of human Eph receptor was performed following the steps below.

Rabbit anti-6-His antibody (Bethyl Laboratories) was coated onto the wells of a 96-well plate (Nunc). After incubating at 4° C. overnight, wells were blocked at room temperature for one hour with 1% Block ACE (DS Pharma Biomedical). After washing three times with 0.05% Tween 20/PBS (Thermo SCIENTIFIC), each Eph receptor extracellular region of human-SEAP-His protein (final concentration 1 nM) was seeded in each well, and this was incubated at room temperature for one hour. After washing three times, human IgG solution (100 µg/mL, Mitsubishi Pharma Corporation) and antibody A (10 µg/mL) were added to the wells, and this was incubated at room temperature for one hour. Horseradish peroxidase-labeled donkey anti-mouse IgG antibody (Jackson ImmunoResearch Laboratories) was added, and this was incubated at room temperature for one hour. After washing three times, TMBZ (3,3',5,5'-tetramethylbenzidine, Sigma) solution was added to the wells, and upon confirmation of a moderate amount of coloring, an equal amount of the stop solution (1N $H_2SO_4$, Wako Pure Chemical) was added to the wells, and absorbance at 450 nm was read with a microplate reader (PerkinElmer).

Figure 5:
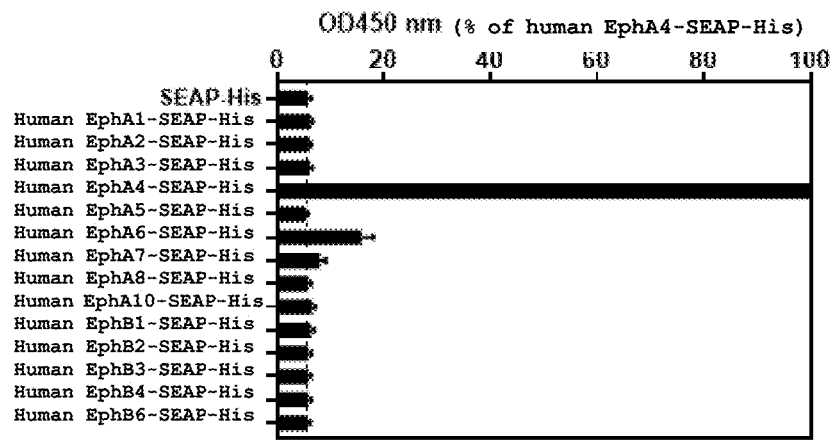
FIG. 5 shows the selectivity of the anti-EphA4 monoclonal antibody (antibody A) against each human Eph receptor.

Among the human Eph receptor family, antibody A had specific binding activity only towards human EphA4 (FIG. 5).

Reference Example 7: Selectivity of Anti-EphA4 Monoclonal Antibody Against Mouse Eph Receptor Following the method for preparing EphA4 extracellular region-Fc-His protein according to Reference Example 1, the DNA sequences encoding the signal sequence and the extracellular region of each Eph receptor of mouse (EphA1, EphA3, EphA4, EphA5, EphA6, EphA7, EphA8, EphA10, EphB1, EphB2, EphB3, EphB4, and EphB6) were amplified by RT-PCR with total RNA derived from tissue, and cloned into pENTR1A vector (Invitrogen/LifeTechnologies) having the DNA sequence encoding the Fc region of human $IgG_1$ and histidine tag. Next, the DNA sequences encoding the signal sequence and extracellular region of each Eph receptor of mouse, Fc, and histidine tag (EphA1, EphA3, EphA4, EphA5, EphA6, EphA7, EphA8, EphA10, EphB1, EphB2, EphB3, EphB4, and EphB6) were transferred to pcDNA 3.1_rfcB vector by LR reaction of Gateway System (Invitrogen/LifeTechnologies) to construct the extracellular region of each Eph receptor of mouse-Fc-His protein expression vector. In the construction of the extracellular region of mouse EphA2-Fc-His protein expression vector, the DNA sequences encoding the signal sequence and the extracellular region of mouse EphA2 were amplified by RT-PCR with total RNA derived from tissue, and cloned into pcDNA 3.1 vector having the DNA sequence encoding Fc and histidine tag to construct a mouse EphA2 extracellular region-Fc-His protein expression vector.

Next, each Eph receptor extracellular region of mouse-Fc-His protein expression vector was introduced into Expi293F cells (Gibco/ThermoFisher) with Expi293 expression system (Gibco/ThermoFisher). After 5 days of culture (5% CO2, 37° C., 120 rpm), the culture supernatant was recovered, and this was centrifuged at room temperature, at 1500 rpm, and for 5 minutes. The centrifuged supernatant was filtered with a 0.45 µm filter (Millipore).

For antibody A, the evaluation of the binding activity of mouse Eph receptor was performed following the steps below.

Rabbit anti-6-His antibody (Bethyl Laboratories) was coated onto the wells of a 96-well plate (Nunc). After incubating at 4° C. overnight, wells were blocked at room temperature for one hour with 1% Block ACE (DS Pharma Biomedical). After washing three times with 0.05% Tween 20/PBS (Thermo SCIENTIFIC), each Eph receptor extracellular region of mouse-Fc-His protein (final concentration 1 nM) was seeded in each well, and this was incubated at room temperature for one hour. After washing three times, human IgG solution (100 μg/mL, Sigma) and antibody A (10 μg/mL) were added to the wells, and this was incubated at room temperature for one hour. Horseradish peroxidase-labeled donkey anti-mouse IgG antibody (Jackson ImmunoResearch Laboratories) was added, and this was incubated at room temperature for one hour. After washing three times, TMBZ (3,3',5,5'-tetramethylbenzidine, Sigma) solution was added to the wells, and upon confirmation of a moderate amount of coloring, an equal amount of the stop solution (1N $H_2SO_4$, Wako Pure Chemical) was added to the wells, and absorbance at 450 nm was read with a microplate reader (PerkinElmer).

Figure 6:
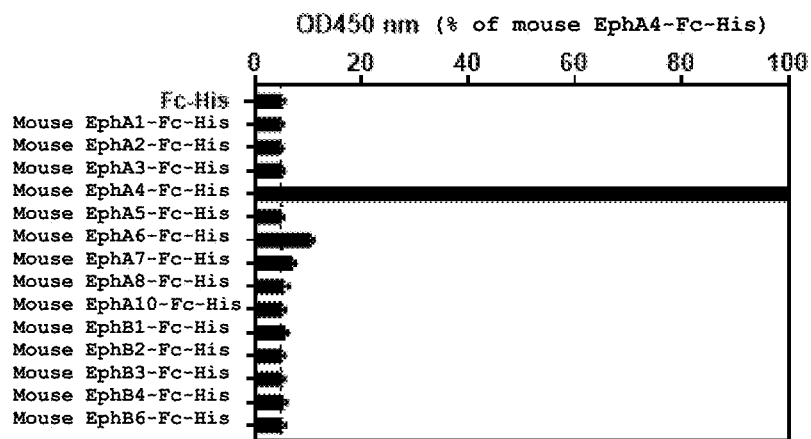
FIG. 6 shows the selectivity of the anti-EphA4 monoclonal antibody (antibody A) against each mouse Eph receptor.

Among the mouse Eph receptor family, antibody A had specific binding activity only towards mouse EphA4 (FIG. 6).

Reference Example 8: Reactivity of Anti-EphA4 Monoclonal Antibody Against Mouse, Rat, Monkey, and Human EphA4

The preparation of mouse, rat, monkey, and human EphA4 extracellular regions-Fc-His proteins was performed following the steps below. First, following the method for preparing EphA4 extracellular region-Fc-His protein according to Reference Example 1, monkey EphA4 extracellular region-Fc-His protein expression vector was constructed. The amino acid sequence of monkey EphA4 utilized in vector construction is shown as SEQ ID NO. 32, and the extracellular region thereof is shown as SEQ ID NO. 33. Various EphA4 extracellular region-Fc-His proteins were prepared employing the monkey EphA4 extracellular region-Fc-His protein expression vector as well as the mouse, rat, and human EphA4 extracellular region-Fc-His protein expression vectors described in Reference Example 1.

For antibody A, the evaluation of the binding activity with various EphA4 extracellular regions was performed following the steps below.

Donkey anti-human IgG antibody (Jackson ImmunoResearch Laboratories) was coated onto the wells of a 96-well plate (Nunc). After incubating at 4° C. overnight, wells were blocked at room temperature for one hour with 1% Block ACE (DS Pharma Biomedical). After washing three times with 0.05% Tween 20/PBS (Thermo SCIENTIFIC), mouse, rat, monkey, and human EphA4 extracellular regions-Fc-His proteins (final concentration 1 nM) were seeded in the wells, and this was incubated at room temperature for one hour. After washing three times, human IgG solution (100 μg/mL, Mitsubishi Pharma Corporation) and antibody A (0, 0.00013, 0.00064, 0.0032, 0.016, 0.08, 0.4, 2, and 10 μg/mL) were added to the wells, and this was incubated at room temperature for one hour. Horseradish peroxidase-labeled donkey anti-mouse IgG antibody (Jackson ImmunoResearch Laboratories) was added, and this was incubated at room temperature for one hour. After washing three times, TMBZ (3,3',5,5'-tetramethylbenzidine, Sigma) solution was added to the wells, and upon confirmation of a moderate amount of coloring, an equal amount of the stop solution (1N $H_2SO_4$, Wako Pure Chemical) was added to the wells, and absorbance at 450 nm was read with a microplate reader (PerkinElmer).

Figure 7:
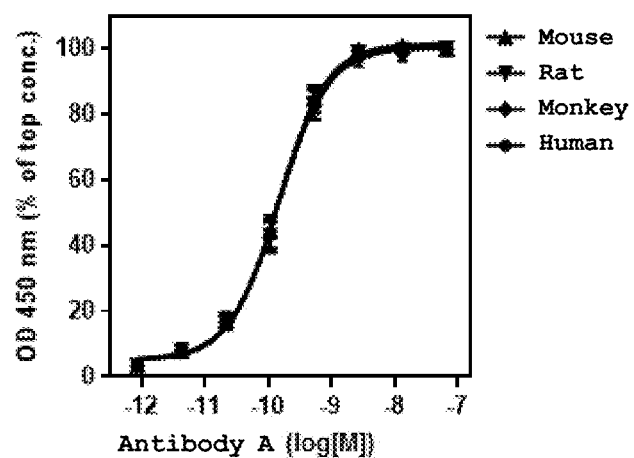
FIG. 7 shows the reactivity of the anti-EphA4 monoclonal antibody (antibody A) against mouse, rat, monkey, and human EphA4.

Antibody A had equivalent binding activity in all of mouse, rat, monkey, and human EphA4 (FIG. 7).

Reference Example 9: Reactivity of Anti-EphA4 Monoclonal Antibody Against Human EphA4 Extracellular Region, Ligand Binding Domain, Fibronectin Type III Domain 1, Fibronectin Type III Domain 2

The preparation of proteins having the extracellular region (ECD), ligand binding domain (LBD), fibronectin type III domain 1 (FN1), or fibronectin type III domain 2 (FN2) of human EphA4 fused with maltose-binding protein (MBP) and histidine tag (hereinafter referred to as "human EphA4 extracellular region-MBP-His protein," "human EphA4 ligand binding domain-MBP-His protein," "human EphA4 fibronectin type III domain 1-MBP-His protein," and "human EphA4 fibronectin type III domain 2-MBP-His protein") was performed following the steps below. Initially, pcDNA 3.4-human EphA4 extracellular region, ligand binding domain, fibronectin type III domain 1, or fibronectin type III domain 2-MBP-His expression vectors were constructed. First, the signal sequence of human EphA4 (SEQ ID NO. 34) or the signal sequence of preprotrypsin (SEQ ID NO. 35) and the DNA sequences encoding each domain of human EphA4 were amplified by PCR, and cloned into pcDNA 3.4 vector having the DNA sequence encoding MBP and histidine tag (Invitrogen/LifeTechnologies) to construct human EphA4 extracellular region-MBP-His protein, human EphA4 ligand binding domain-MBP-His protein, human EphA4 fibronectin type III domain 1-MBP-His protein, and human EphA4 fibronectin type III domain 2-MBP-His protein expression vectors. The amino acid sequence of human EphA4 utilized in vector construction is shown as SEQ ID NO. 5, the extracellular region thereof as SEQ ID NO. 36, the ligand binding domain as SEQ ID NO. 37, the fibronectin type III domain 1 as SEQ ID NO. 38, and the fibronectin type III domain 2 as SEQ ID NO. 39. The above expression vectors were transfected into Expi293F cells (Thermo SCIENTIFIC) with Expi293 expression system (Thermo SCIENTIFIC). Four days later, the culture supernatant was recovered, and passed through a 0.45 Nm filter (Millipore). Crude purification was performed with Amylose resin (NEB), and the buffer was substituted to PBS (Wako Pure Chemical) with Zeba Spin Desalting column (Thermo SCIENTIFIC). The monomer fraction was differentially purified with Superdex 200 10/300 (GE Healthcare).

For antibody A, the evaluation of the binding activity with various domains in human EphA4 was performed following the steps below.

Rabbit anti-6-His antibody (Bethyl Laboratories) was coated onto the wells of a 96-well plate (Nunc). After incubating at 4° C. overnight, wells were blocked at room temperature for one hour with 11 Block ACE (DS Pharma Biomedical). After washing twice with 0.02% Tween 20/PBS (Nacalai Tesque), human EphA4 extracellular region-MBP-His protein, human EphA4 ligand binding domain-MBP-His protein, human EphA4 fibronectin type III domain 1-MBP-His protein, and human EphA4 fibronectin type III domain 2-MBP-His protein (final concentration 10 nM) were seeded in the wells, and this was incubated at room temperature for one hour. After washing three times, antibody A (final concentration 10 nM) was added to the wells, and this was incubated at room temperature for one hour. Horseradish peroxidase-labeled goat anti-mouse IgG Fcγ fragment antibody (Jackson ImmunoResearch Laboratories) was added, and this was incubated at room temperature for one hour. After washing five times, TMB solution (KPL) was added to the wells, and upon confirmation of a moderate amount of coloring, an equal amount of the stop solution (2 N H$_2$SO$_4$, Wako Pure Chemical) was added to the wells. Absorbance at 450 nm and 650 nm were read by a microplate reader (PerkinElmer).

Figure 8:
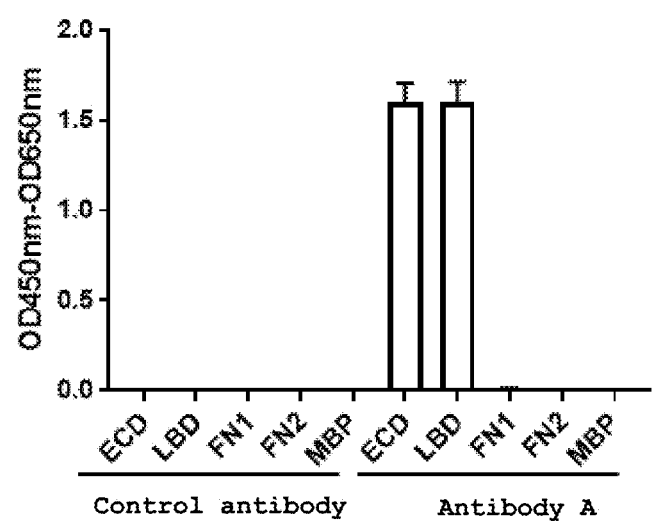
FIG. 8 shows the reactivity of the anti-EphA4 monoclonal antibody (antibody A) against human EphA4 extracellular region (ECD), ligand binding domain (LBD), fibronectin type III domain 1 (FN1), and fibronectin type III domain 2 (FN2).

Antibody A had binding activity for human EphA4 extracellular region (ECD) and ligand binding domain (LBD) (FIG. 8). There was no reaction for fibronectin type III domain 1 (FN1) and fibronectin type III domain 2 (FN2). Accordingly, it was found that antibody A specifically binds to the ligand binding domain of the human EphA4 extracellular region.

Reference Example 10: Effect of Anti-EphA4 Monoclonal Antibody on Increasing the Number of Spines in the Hippocampus Neuron Preparation of rat hippocampus neurons was performed as described in the above Reference Example 1 (B). Rat hippocampus neurons were introduced with EGFP gene employing Nucleofector (Lonza), mixed with rat hippocampus neurons without gene introduction, and seeded in a 24-well plate (Falcon) containing a cover glass (Matsunami Glass Industries) coated with poly-L-lysine.

The counting of spine employing hippocampus neurons was performed following the steps below. Rat hippocampus neurons introduced with EGFP at culture Day 13 seeded in a 24-well plate (Falcon) containing a cover glass (Matsunami Glass Industries) coated with poly-L-lysine were treated with control antibody (mouse IgG$_1$; BioLegend) or antibody A (6.7 and 20 nM) for 24 hours. The cover glass was then transferred to 2% PFA (Wako Pure Chemical)/4% sucrose (Wako Pure Chemical)/PBS, and this was left standing for 20 minutes to fix the cells. After removing the fixative solution and washing the cells three times with PBS, 0.25% Triton X-100 (Wako Pure Chemical)/PBS was added, and cell permeabilization was performed for 15 minutes. The solution was removed, the cover glass was transferred to 2% BSA (Sigma)/0.25% Triton X-100/Opti-MEM (GIBCO) and subjected to one hour of blocking, after which anti-GFP antibody (Nacalai Tesque) was allowed to react for 1.5 hours. After removing the primary antibody solution and washing three times with PBS, the secondary antibody was allowed to react for one hour. After removing the secondary antibody solution and washing three times with PBS, Prolong Gold antifade reagent (Molecular probes) was added for mounting, and observation was performed with LSM800 (ZEISS). The experiment described above was carried out three times, and for each experiment, neurons were extracted from two cover glasses, spines on each dendrite were counted with image analysis software Imaris® (Bitplane), and the number of spines per 10 μm for each neuron was calculated.

Figure 9:
FIG. 9 shows the effect of the anti-EphA4 monoclonal antibody (antibody A) on increasing the number of spines in the hippocampus neuron.

Antibody A increased the number of spines in the hippocampus neuron (FIG. 9). This result shows that antibody A has the activity to stabilize spines in hippocampus neurons.

Reference Example 11: Effect of Anti-EphA4 Monoclonal Antibody to Suppress Tau Phosphorylation In Vivo The evaluation of the effect to suppress tau phosphorylation in vivo employing tau transgenic mouse (rTg4510) was performed following the steps below. Tau transgenic mice (rTg4510) were subcutaneously administered twice a week from 20 to 26 weeks-old with antibody A or control antibody prepares by conventional methods by immunizing a mouse with dinitrophenol (mouse anti-dinitrophenol antibody) at a dose of 100 mg/kg (10 mL/kg) each. On 3.5 days after the final administration, anesthesia was done with 2% isoflurane (Intervet) and a mix of three types of anesthetic drugs (4.0 mg/kg of Dormicum (Astellas Pharma), 0.3 mg/kg of Domitor (Nippon Zenyaku Kogyo), and 5.0 mg/kg of Vetorphale (Meiji Seika Pharma)), perfusion was performed under anesthesia with PBS (Wako Pure Chemical) containing 3 units/mL of heparin (Ajinomoto) and 1$^1$ phosphatase inhibitor cocktail (Nacalai Tesque), and the cerebral hemisphere was resected. The cerebral hemisphere collected was fixed at 4° C. while shaking overnight in 2% paraformaldehyde (TAAB)/0.1 M phosphate buffer (Wako Pure Chemical). The cerebral hemisphere was substituted with 20% sucrose (Wako Pure Chemical)/0.1 M phosphate buffer (Wako Pure Chemical) and subsequently 25% sucrose/0.1 M phosphate buffer (Wako Pure Chemical), and then embedded in Tissue-Tek O.C.T. Compound (Sakura Finetek Japan)/25% sucrose, and frozen with liquid nitrogen. Slices were created at a thickness of 7 μm with cryostat CM1860 (Leica), adhered on a slide glass (Muto Pure Chemicals), air-dried with cold air, and then placed in a sealed bag and stored at −80° C. The slide glass used for immunostaining was thawed, air-dried with cold air, and then washed with PBS (Wako Pure Chemical), immersed in 1% BSA (Sigma)/10 normal donkey serum (Jackson ImmunoResearch Laboratories)/0.5% Triton X-100 (Wako Pure Chemical)/PBS solution, and subjected to one hour of blocking, after which anti-phosphorylated tau antibody AT8 (Fujirebio Europe N.V.) was allowed to react overnight at ordinary temperatures. After washing three times with PBS, the secondary antibody was allowed to react for one hour. After washing three times with PBS, Prolong Gold antifade reagent (Molecular probes) was placed on the slice and mounted, and observation was performed with LSM700 (ZEISS). The AT8 signal-positive area in the hippocampus CA1 stratum radiatum was measured with image analysis software ImageJ, and the proportion of the AT8-positive signal area against the total area was calculated.

Figure 10:
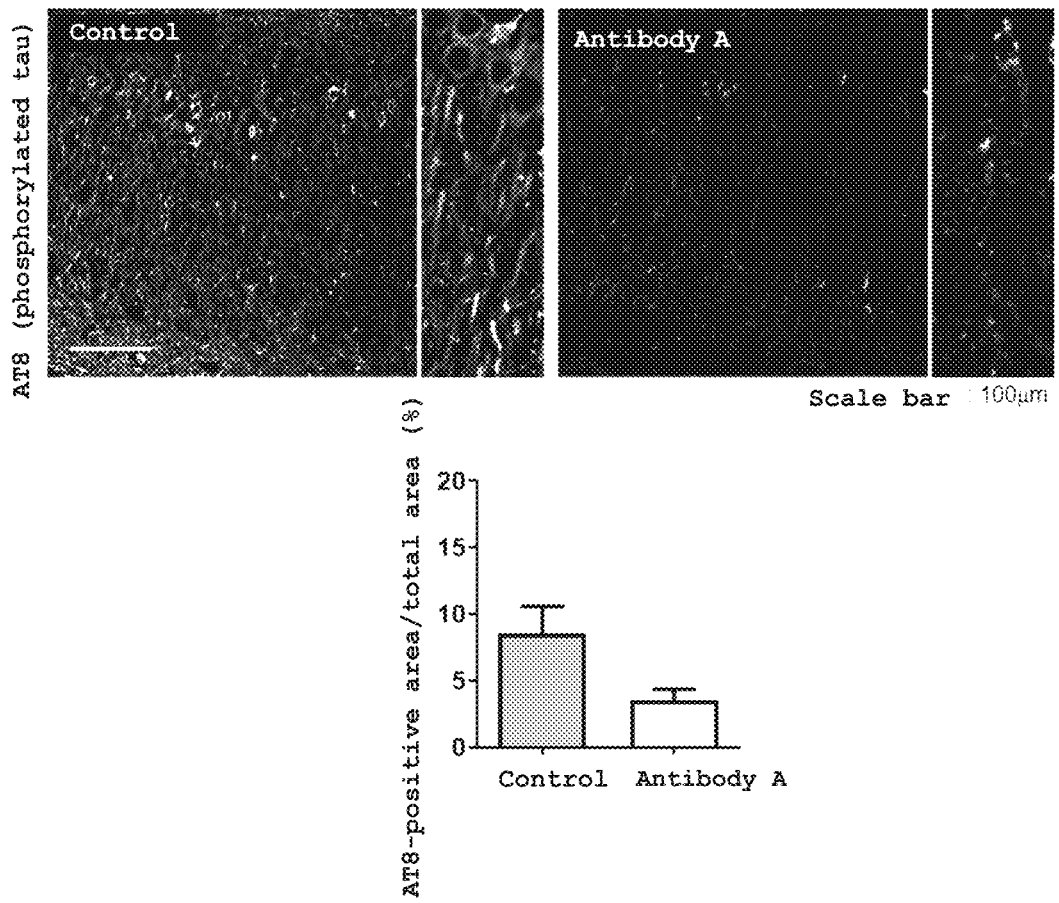
FIG. 10 shows the effect to suppress tau phosphorylation of the anti-EphA4 monoclonal antibody in vivo.

Antibody A decreased the signal of phosphorylated tau in the hippocampus CA1 region (FIG. 10). This result shows that antibody A has the activity to suppress the progression of tau pathology in tau transgenic mouse (rTg4510).

Reference Example 12: Epitope Mapping of EphA4-Ligand Binding Domain (EphA4-LBD) by X-Ray Crystal Structure Analysis The preparation of antibody A-Fab was performed following the steps below. Antibody A at 101.1 mg was dissolved in 0.1 M sodium phosphate buffer (pH 7.0) comprising 30 mM L-cysteine and 2 mM EDTA at a concentration of 15 mg/mL. To this antibody solution, papain (Sigma) was added at 1/200 amount to the antibody, and enzymatic digestion was performed at 37° C. for 18 hours. The antibody A enzymatic digestion juice was dialyzed against PBS, and the precipitate was removed by centrifugation (the precipitate produced was redissolved in PBS and mixed with the centrifugation supernatant). Next, the following steps were performed with the purpose of removing impurities other than antibody A-Fab.

1) Purification by Protein a Column

This enzymatic digestion solution was applied to 2 mL of ProSep vA High Capacity (Millipore) equilibrated with PBS, and the pass-through fraction and the PBS wash fraction were recovered.

2) Affinity Purification Employing Anti-Human IgG Fcγ Antibody

An affinity column having the anti-human IgG Fcγ antibody (Jackson ImmunoResearch Laboratories) covalently bound to NHS-Activated Sepharose 4FF (GE Healthcare) was prepared according to the manual of this Sepharose. The solution recovered in the above 1) was charged to this affinity column, and the pass-through solution and the PBS wash solution thereof were recovered.

3) Purification by Gel Filtration

The pass-through fraction obtained in the above 2) was concentrated with an ultrafiltration membrane. Superose 12 (GE Healthcare) was equilibrated with PBS, the concentrated sample was applied and separated and purified. A part of the separated and purified fraction was analyzed with SDS-PAGE, and the fraction comprising antibody A-Fab with high purity was recovered and pooled. The sample purified in this way was set as antibody A-Fab.

EphA4-LBD was prepared in order to prepare a complex of antibody A-Fab and the antigen EphA4-LBD (Qin H. et al., J. Biol. Chem., 283: 29473-29484 (2008)). EphA4-LBD at 0.68 μmol (200 μM, 3.4 mL) and antibody A-Fab at 0.45 μmol (300 μM, 1.5 mL) were mixed so that EphA4-LBD will have a molar ratio of about 1.5 folds against antibody A-Fab. Next, the mixed solution was applied to HILOAD26/60 Superdex 75 prep grade (GE Healthcare), and eluted with the buffer for chromatography (25 mM Tris/HCl (pH 7.5), 100 mM NaCl). The fraction comprising the complex was analyzed with SDS PAGE, the fractions having high purity were gathered and concentrated to about 40.8 mg/mL, and this was employed for crystallization.

Crystallization of the complex was performed by sitting drop vapor diffusion method with an auto crystallization device Hydra II Plus One System (Matrix Technologies Corp., Ltd.). MRC-2 (Molecular Dimensions) was used as the plate. The composition of the reservoir solution was 100 mM HEPES (pH 7.5), 10% Polyethylene Glycol 8000, and 8% Ethylene Glycol, and this reservoir solution and the above complex solution were mixed so that the volume ratio was 1:1 to generate crystallization droplets. The crystallization plate generated was left standing at 20° C.

Upon crystallization under the above condition, crystals having space group P212121, lattice constants a=71.0 Å, b=84.5 Å, and c=116.1 Å were obtained. Radiation light X-Ray (1.0 Å) was incidented to the crystals obtained to obtain diffraction data of 1.79 Å. The diffraction data was processed by HKL2000 (HKL Research Inc.), and phase determination was performed by molecular substitution method. The program PHASER (version 2.5.0, McCoy A. J. et al., J. Appl. Cryst. 40: 658-674 (2007)) included in CCP4 Software Suite (Collaborative computational project number 4, [CCP4] version 6.5.0, Acta Cryst. D 67: 235-242 (2011)) was employed for the molecular substitution method. The crystal structure of EphA4-LBD (PDBID: 3CKH) and the crystal structure of the Fab region of IgG (PDBID:2VXT (L-chain) and 1FGN (H-chain)) were employed as the search model of the molecular substitution method. A molecular model was constructed with the program COOT (Emsley P. et al., Acta Cryst. D 60: 2126-2132n (2004)) so as to fit the electron density obtained from the phase determined, and structure refinement was performed with the program REFMAC (Murshudov G. N., Acta Cryst. D 53: 240-255 (1997)).

The complex crystal structure of 2.0 Å resolution was obtained by structural calculation (R=0.212, Rfree=0.258).

Figure 11A:
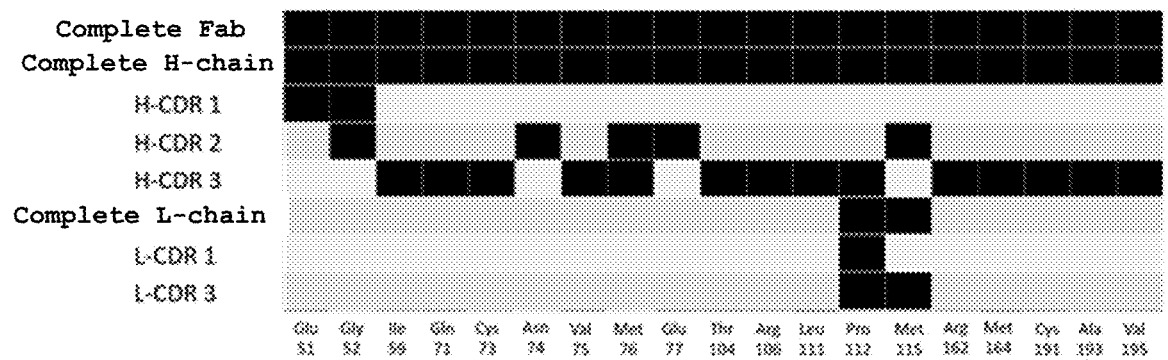
FIG. 11A shows the amino acids of the EphA4-Ligand Binding Domain (EphA4-LBD) on the horizontal axis, and the structural region of antibody A-Fab on the vertical axis. Black bits show the intersecting points of combinations where interaction is present.
Figure 11B:
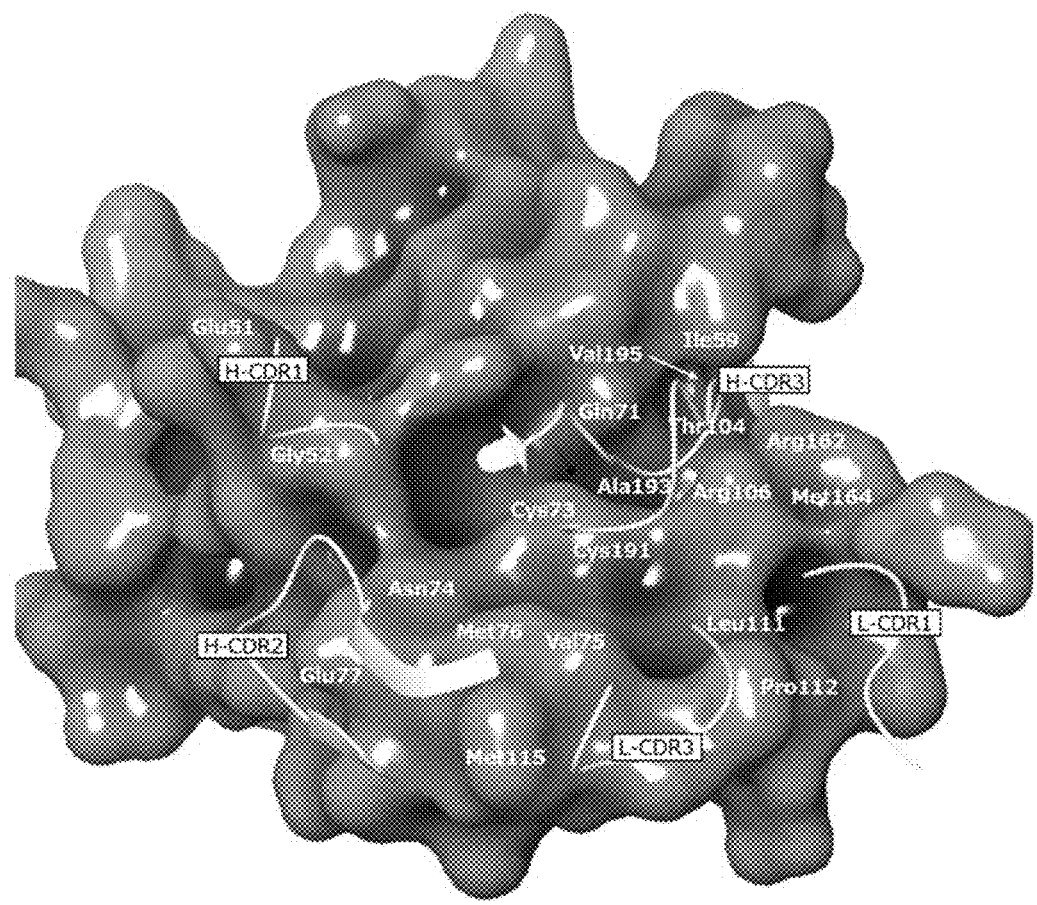
FIG. 11B shows the surface structure of EphA4-Ligand Binding Domain (EphA4-LBD).

The crystal structure of the antibody A-Fab/EphA4-LBD complex obtained was analyzed with the interaction detection tool equipped in the computational chemical system MOE 2018.0101 (Chemical Computing Group Inc.), and the amino acid residues on EphA4-LBD which are in direct contact with antibody A-Fab were identified (FIG. 11A). The identified amino acid residues are Glu51, Gly52, Ile59, Gln71, Cys73, Asn74, Val75, Met76, Glu77, Thr104, Arg106, Leu111, Pro112, Met115, Arg162, Met164, Cys191, Ala193, and Val195. FIG. 11B shows the surface structure of EphA4-LBD generated with Maestro (version 11.0, Schrodinger, LLC). As a result, the present inventors concluded that the region where these amino acid residues are present is the antibody A-Fab binding region in EphA4-LBD.

Example 1: Preparation of Humanized Antibody of Antibody A

Preparation of Humanized Anti-EphA4 Antibody

The variable region of the humanized antibody was designed. Based on the high homology against the framework region (FR) of antibody A, among the FRs of human antibody, IGHV3-33*03 (SEQ ID NO. 42) and JH6 (SEQ ID NO. 43) for the heavy chain and IGKV1-17*01 (SEQ ID NO. 40) and JK4 (SEQ ID NO. 41) for the light chain were selected as the FRs for the humanized antibody. The amino acids in the FR that interact with the amino acids of the CDR were then predicted employing a 3D structure prediction model of mouse antibody A, these were transplanted together with the CDR of antibody A having Y32F mutation in the CDR1 of the heavy chain (SEQ ID NO. 44, 27, 28, and 29-31), and HK2-42 (SEQ ID NO. 45) was designed as the heavy chain variable region of the humanized antibody and L1-8 (SEQ ID NO. 46) was designed as the light chain variable region of the humanized antibody. The amino acid sequences of the transplanted CDR are shown in Table 2, and the nucleic acid sequences are shown in Table 3.

The constant region of human IgG$_2$ (SEQ ID NO. 47) was employed as the heavy chain constant region. Human Igκ (SEQ ID NO. 48) was employed as the light chain constant region. An expression vector (pcDNA 3.4) comprising the gene sequence encoding the amino acid sequence of the humanized antibody was transfected into Expi293F cells (Gibco/ThermoFisher) with Expi293 expression system (Gibco/ThermoFisher). As the gene sequence encoding the amino acid sequence of the humanized antibody, the nucleic acid sequence shown in SEQ ID NO. 55 was employed as heavy chain variable region, the nucleic acid sequence shown in SEQ ID NO. 56 was employed as light chain variable region, the nucleic acid sequence shown in SEQ ID NO. 57 was employed as the heavy chain constant region, and the nucleic acid sequence shown in SEQ ID NO. 58 was employed as the light chain constant region, respectively. The amino acid sequence of the full length of the heavy chain (not including the signal sequence) of the humanized antibody is the amino acid sequence shown in SEQ ID NO. 59, the amino acid sequence of the full length of the light chain (not including the signal sequence) is the amino acid sequence shown in SEQ ID NO. 60. The nucleic acid sequence encoding the full length of the heavy chain of the humanized antibody is the nucleic acid sequence shown in SEQ ID NO. 61, and the nucleic acid sequence encoding the full length of the light chain is the nucleic acid sequence shown in SEQ ID NO. 62. The supernatant was recovered, and the humanized antibody of antibody A (antibody B) was purified with MabSelectSuRe (GE Healthcare).

TABLE 2

Amino acid sequences of CDR of antibody B

| Name | Sequence |
| --- | --- |
| Heavy chain CDR1 | REGVH (SEQ ID NO. 44) |
| Heavy chain CDR2 | VIWRGGSTDYNAAFYMS (SEQ ID NO. 27) |
| Heavy chain CDR3 | ESLEGVYYDYGYYSMDY (SEQ ID NO. 28) |
| Light chain CDR1 | RASQEISGYLS (SEQ ID NO. 29) |
| Light chain CDR2 | AASTLDS (SEQ ID NO. 30) |
| Light chain CDR3 | LQYASYPLT (SEQ ID NO. 31) |

TABLE 3

Nucleic acid sequences of CDR of antibody B

| Name | Sequence |
| --- | --- |
| Heavy chain CDR1 | AGATTTGGAGTGCAT (SEQ ID NO. 49) |
| Heavy chain CDR2 | GTGATCTGGAGGGGAGGATCCGA CTACAACGCTGCTTTTATGAGC (SEQ ID NO. 50) |
| Heavy chain CDR3 | GAGAGCCTGTTCGGCGTGTACTATGAC TACGGCTACTATTCTATGGATTAT (SEQ ID NO. 51) |
| Light chain CDR1 | CGCGCCTCCCAGGAGATCTCTGGCTA CCTGTCC (SEQ ID NO. 52) |
| Light chain CDR2 | GCTGCCTCCACCCTGGACTCT (SEQ ID NO. 53) |
| Light chain CDR3 | CTGCAGTACGCTTCCTATCCACTGA CC (SEQ ID NO. 54) |

Example 2: Affinity of Humanized Anti-EphA4 Monoclonal Antibody Against Human EphA4

The binding affinity of antibody B obtained in Example 1 against human EphA4 was determined by surface plasmon resonance (SPR method) employing Biacore T200 (GE Healthcare). First, anti-His antibody (GE Healthcare, 28-9950-56) was fixed onto a sensor chip CM5. Fixation was performed by amine coupling method employing N-hydroxysuccinimide (NHS) and N-ethyl-N'-(3-dimethylaminopropyl)carbodiimide hydrochloride (EDC), and ethanolamine was employed for blocking (sensor chip and fixation reagent were all from GE Healthcare). This was diluted to 3.5 μg/mL with the fixation buffer (10 mM sodium acetate, pH 4.5), and fixed on the sensor chip according to the protocol attached to Biacore T200. Human EphA4 extracellular region-SEAP-His10 was diluted with the running buffer HBS-EP (GE Healthcare, BR-1001-88), and the solution was sent onto a flow cell for 120 seconds for capture (the captured amount about 10 RU). Subsequently, antibody B serially diluted to the range of 100, 50, 25, 12.5, 6.3, 3.2, 1.6, and 0 nM with HBS-EP was added to the sensor chip for 120 seconds, and the binding reaction curve at the time of addition (binding phase, 120 seconds) and after addition had completed (dissociation phase, 600 seconds) was sequentially observed. After the completion of each observation, 4 M $MgCl_2$ (60 seconds, Wako Pure Chemical) was added to regenerate the sensor chip. Fitting analysis by 1:1 binding model employing BIA evaluation software attached to the system was performed on the binding reaction curve obtained, and the affinity (KD=kd/ka) against human EphA4 was calculated.

Figure 12:
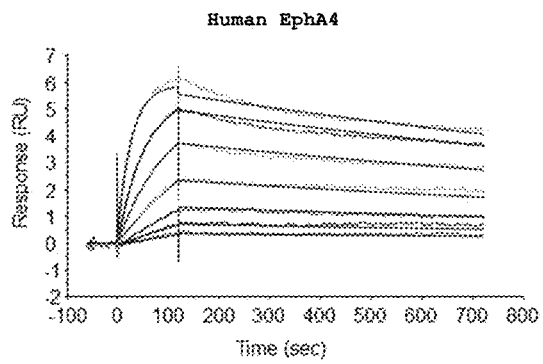
FIG. 12 shows the affinity of the humanized anti-EphA4 monoclonal antibody (antibody B) against human EphA4.

The binding affinity of antibody B against human EphA4 (KD value) was $1.34 \times 10^{-9}$ M (FIG. 12). It was shown that antibody B shows an almost equivalent affinity as antibody A which is the antibody before humanization.

Example 3: EphA4 Cleavage Enhancement Activity of Humanized Anti-EphA4 Monoclonal Antibody in Hippocampus Neurons For antibody B obtained in Example 1, evaluation of EphA4 cleavage enhancement activity employing hippocampus neurons was performed following the steps below.

Rat hippocampus neurons seeded in a 96-well dish (Falcon) were treated with antibody B (2.0, 6.7, and 20 nM) and γ selectase inhibitory drug Compound E (50 nM, Enzo Life Sciences). Twenty-four hours later, this was washed with PBS (Wako Pure Chemical), SDS sample buffer (Laemmli sample buffer (Bio-Rad) and 5% 2-mercaptoethanol (Bio-Rad)) was added to recover the cells, and this was boiled for 5 minutes. SDS-PAGE was performed with this sample, western blotting with anti-EphA4 monoclonal antibody (Abnova) was performed, the band strength was quantified, and the value of EphA4 C-terminal fragment/full length EphA4 was calculated.

Figure 13:
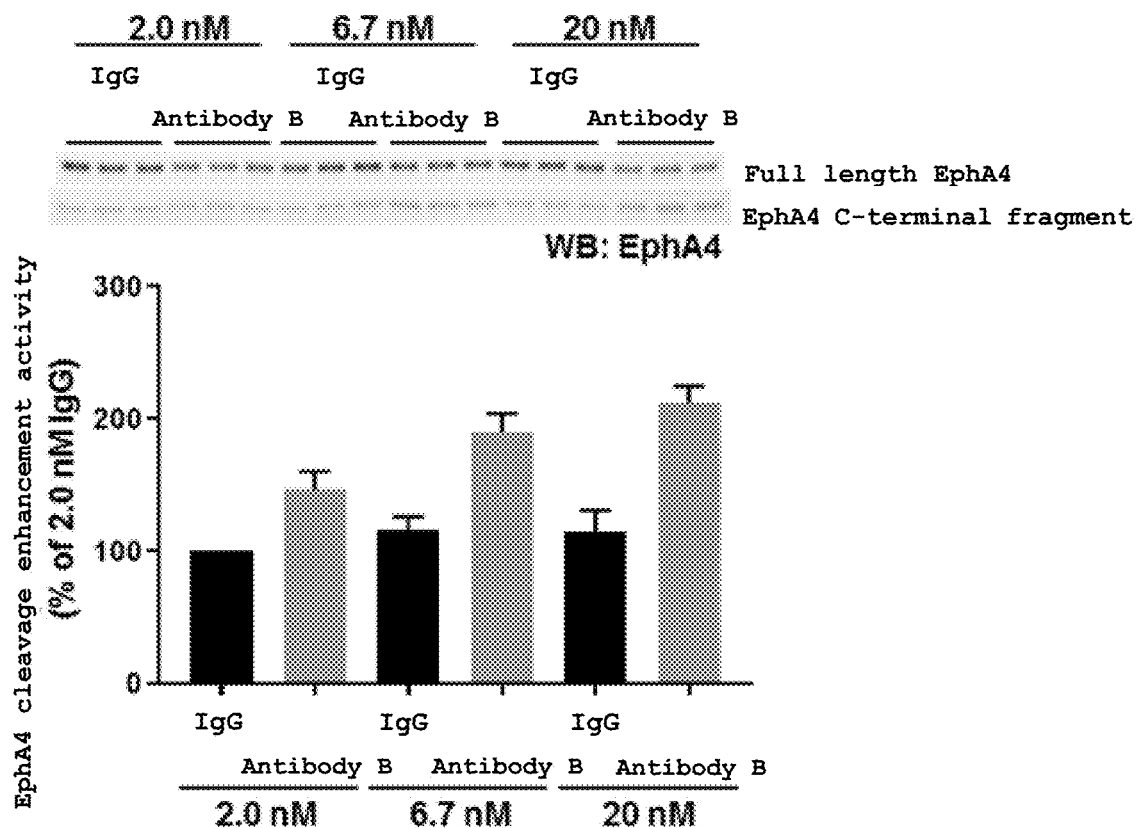
FIG. 13 shows EphA4 cleavage enhancement activity of the humanized anti-EphA4 monoclonal antibody (antibody B) in the hippocampus neuron.

Antibody B concentration-dependently enhanced EphA4 cleavage reaction in hippocampus neurons (FIG. 13)

Example 4: Human EphA4-Human Ligand Binding Inhibitory Activity of Humanized Anti-EphA4 Monoclonal Antibody For antibody B obtained in Example 1, the evaluation of the inhibitory activity of binding between human EphA4 and human ligand was performed following the steps below. Anti-alkaline phosphatase antibody (Thermo SCIENTIFIC) was coated onto the wells of a 96-well plate (Nunc). After incubating at 4° C. overnight, wells were blocked at room temperature for one hour with 1% Block ACE (DS Pharma Biomedical). After washing three times with 0.05% Tween 20/PBS (Thermo SCIENTIFIC), human EphA4 extracellular region-SEAP-His protein (final concentration 10 nM) was seeded in the wells, and this was incubated at room temperature for one hour. After washing three times, the ligand and serially diluted antibody B (0, 0.003, 0.01, 0.03, 0.1, 0.3, 1, 3, 10, 30, 100, 300, 1000, and 3000 nM) were added to the wells. Note that biotinylated human Ephrin A5-Fc chimera (R&D Systems, final concentration 0.7 nM) and biotinylated human Ephrin B3-Fc chimera (R&D Systems, final concentration 2.3 nM) were employed as ligands. After incubating at room temperature for one hour and washing three times, horseradish peroxidase-labeled streptavidin (GE Healthcare) was added, and this was incubated at room temperature for one hour. After washing three times, TMBZ (3,3',5,5'-tetramethylbenzidine, Sigma) solution was added to the wells, and this was incubated at room temperature for 2-5 minutes. An equal amount of the stop solution (1N $H_2SO_4$, Wako Pure Chemical) was added to the wells, and absorbance at 450 nm was read with a microplate reader (Molecular Devices or PerkinElmer).

Figure 14:
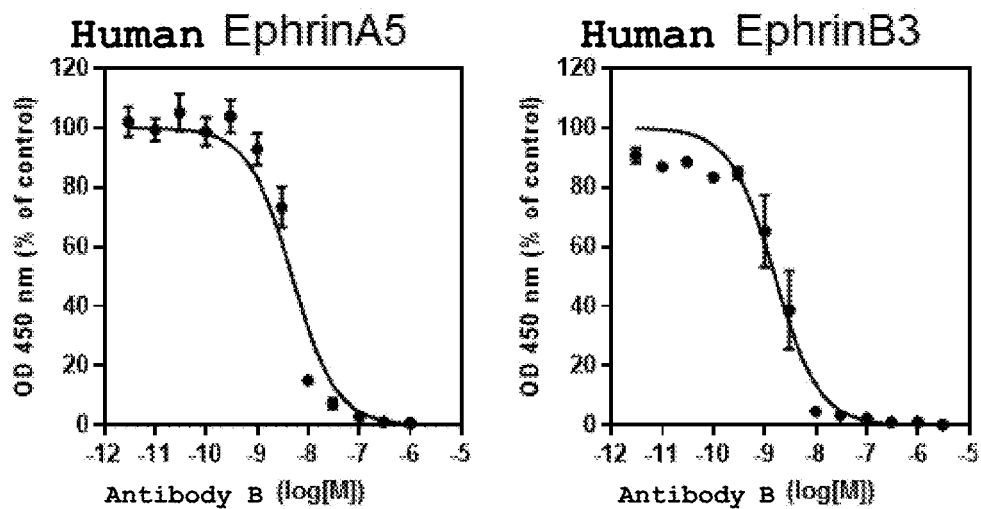
FIG. 14 shows human EphA4-human ligand binding inhibitory activity of the humanized anti-EphA4 monoclonal antibody (antibody B).

Antibody B concentration-dependently suppressed the binding between human EphA4 and human ligand, and the $IC_{50}$ values against human Ephrin A5 and Ephrin B3 binding were about 4.9 nM and 1.6 nM, respectively. Accordingly, it was found that antibody B strongly inhibits the binding between human EphA4 and human ligand, and shows an almost equivalent inhibitory activity as antibody A which is the antibody before humanization (FIG. 14).

Example 5: Mouse EphA4-Mouse Ligand Binding Inhibitory Activity of Humanized Anti-EphA4 Monoclonal Antibody For antibody B obtained in Example 1, the evaluation of the inhibitory activity of binding between mouse EphA4 and mouse ligand was performed following the steps below. Anti-alkaline phosphatase antibody (Thermo SCIENTIFIC) was coated onto the wells of a 96-well plate (Nunc). After incubating at 4° C. overnight, wells were blocked at room temperature for one hour with 1% Block ACE (DS Pharma Biomedical). After washing three times with 0.024 Tween 20/PBS (Thermo SCIENTIFIC), mouse EphA4 extracellular region-SEAP-His protein was added to the wells (final concentration 10 nM), and this was incubated at room temperature for one hour. After washing three times, the ligand and serially diluted antibody B (0, 0.003, 0.01, 0.03, 0.1, 0.3, 1, 3, 10, 30, 100, 300, 1000, and 3000 nM) were added to the wells. Note that biotinylated mouse Ephrin A1-Fc chimera (R&D Systems, final concentration 6 nM) and biotinylated mouse Ephrin B2-Fc chimera (R&D Systems, final concentration 2.5 nM) were employed as ligands. After incubating at room temperature for one hour and washing three times, horseradish peroxidase-labeled streptavidin (GE Healthcare) was added, and this was incubated at room temperature for one hour. After washing three times, TMBZ (3,3',5,5'-tetramethylbenzidine, Sigma) solution was added to the wells, and this was incubated at room temperature for 2 minutes. An equal amount of the stop solution (1N $H_2SO_4$, Wako Pure Chemical) was added to the wells, and absorbance at 450 nm was read with a microplate reader (Molecular Devices or PerkinElmer).

Figure 15:
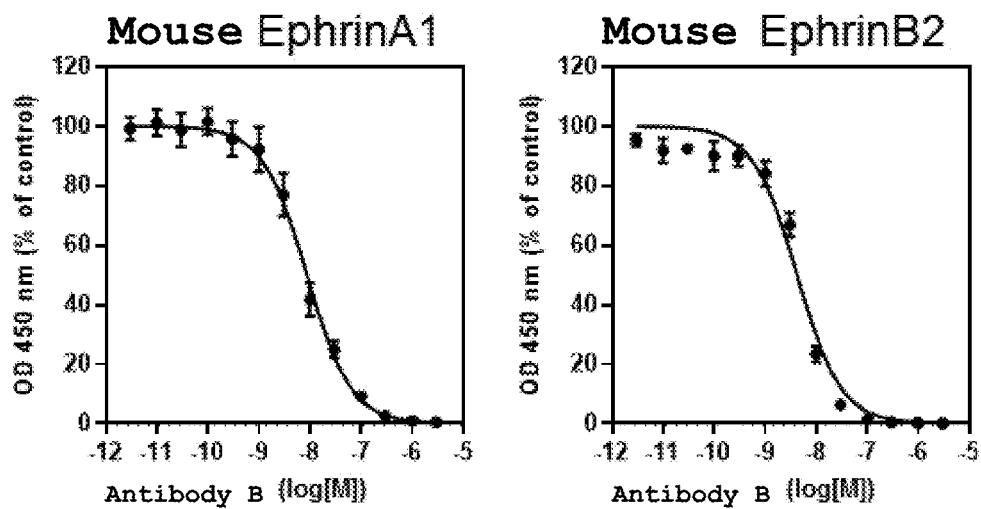
FIG. 15 shows mouse EphA4-mouse ligand binding inhibitory activity of the humanized anti-EphA4 monoclonal antibody (antibody B).

Antibody B concentration-dependently suppressed the binding between mouse EphA4 and mouse ligand, and the $IC_{50}$ values against mouse Ephrin A1 and Ephrin B2 binding were about 8.7 nM and 4.2 nM, respectively. Accordingly, it was found that antibody B strongly inhibits the binding between mouse EphA4 and mouse ligand, and shows an almost equivalent inhibitory activity as antibody A which is the antibody before humanization (FIG. 15).

Example 6: Selectivity of Humanized Anti-EphA4 Monoclonal Antibody Against Human Eph Receptor Similarly to the method for preparing mouse EphA4 extracellular region-SEAP-His protein described in Reference Example 1, the DNA sequences encoding the signal sequence and the extracellular region of each Eph receptor of human (EphA1, EphA2, EphA3, EphA4, EphA5, EphA6, EphA7, EphA8, EphA10, EphB1, EphB2, EphB3, EphB4, and EphB6) were amplified by RT-PCR with total RNA derived from tissue, and cloned into pENTR1A vector (Invitrogen/LifeTechnologies) having the DNA sequence encoding SEAP protein and histidine tag. Next, the DNA sequences encoding the signal sequence and extracellular region of each Eph receptor of human, SEAP protein and histidine tag were transferred to pcDNA 3.1_rfcB vector by LR reaction of Gateway System (Invitrogen/LifeTechnologies) to construct vectors (referred to as "Eph receptor extracellular region-SEAP-His protein expression vector") expressing a protein having SEAP protein and His tag fused to the extracellular region of each Eph receptor of human (referred to as "Eph receptor extracellular region-SEAP-His protein.")

Next, each of human Eph receptor extracellular region-SEAP-His protein expression vectors was introduced into Expi293F cells (Gibco/ThermoFisher) with Expi293 expression system (Gibco/ThermoFisher). After five days of incubation (5% $CO_2$, 37° C.), the culture supernatant was recovered, and this was centrifuged at room temperature, at 1500 rpm, and for 5 minutes. The centrifuged supernatant was filtered with a 0.45 μm filter (Millipore).

For antibody B obtained in Example 1, the evaluation of the binding activity of human Eph receptor was performed following the steps below.

Rabbit anti-6-His antibody (Bethyl Laboratories) was coated onto the wells of a 96-well plate (Nunc). After incubating at 4° C. overnight, wells were blocked at room temperature for one hour with 1% Block ACE (DS Pharma Biomedical). After washing three times with 0.05% Tween 20/PBS (Thermo SCIENTIFIC), each of human Eph receptor extracellular region-SEAP-His proteins (final concentration 1 nM) was seeded in each well, and this was incubated at room temperature for one hour. After washing three times, human IgG solution (100 μg/mL, Mitsubishi Pharma Corporation) and antibody B (10 μg/mL) were added to the wells, and this was incubated at room temperature for one hour. Horseradish peroxidase-labeled donkey anti-human IgG antibody (Jackson ImmunoResearch Laboratories) was added, and this was incubated at room temperature for one hour. After washing three times, TMBZ (3,3',5,5'-tetramethylbenzidine, Sigma) solution was added to the wells, and upon confirmation of a moderate amount of coloring, an equal amount of the stop solution (1N $H_2SO_4$, Wako Pure Chemical) was added to the wells, and absorbance at 450 nm was read with a microplate reader (PerkinElmer).

Figure 16:
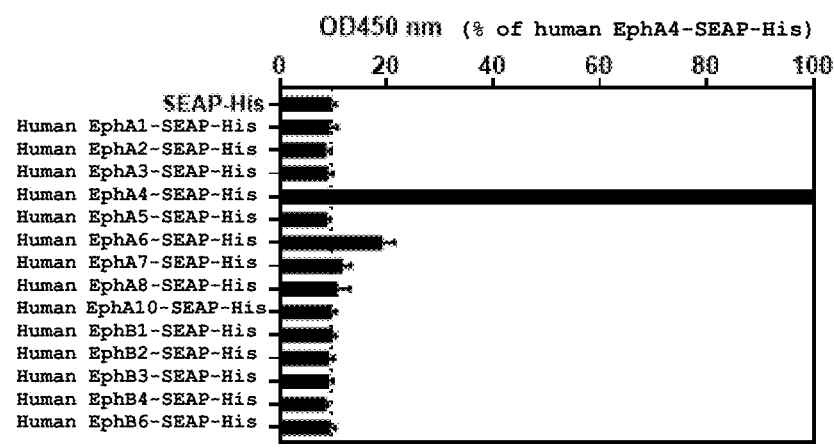
FIG. 16 shows the selectivity of the humanized anti-EphA4 monoclonal antibody (antibody B) against human Eph receptor.

It was found that antibody B, similarly to antibody A which is the antibody before humanization, specifically binds to human EphA4 among the human Eph receptor family (FIG. 16).

Example 7: Selectivity of Humanized Anti-EphA4 Monoclonal Antibody Against Mouse Eph Receptor Following the method for preparing EphA4 extracellular region-Fc-His protein according to Reference Example 1, the DNA sequences encoding the signal sequence and the extracellular region of each Eph receptor of mouse (EphA1, EphA3, EphA4, EphA5, EphA6, EphA7, EphA8, EphA10, EphB1, EphB2, EphB3, EphB4, and EphB6) were amplified by RT-PCR with total RNA derived from tissue, and cloned into pENTR1A vector (Invitrogen/LifeTechnologies) having the DNA sequence encoding the Fc region of human $IgG_1$ and histidine tag. Next, the DNA sequences encoding the signal sequence and extracellular region of each Eph receptor (EphA1, EphA3, EphA4, EphA5, EphA6, EphA7, EphA8, EphA10, EphB1, EphB2, EphB3, EphB4, and EphB6) of mouse, Fc, and histidine tag were transferred to pcDNA 3.1 rfcB vector by LR reaction of Gateway System (Invitrogen/LifeTechnologies) to construct each of mouse Eph receptor extracellular region-Fc-His protein expression vectors. In the construction of mouse EphA2 extracellular region-Fc-His protein expression vector, the DNA sequences encoding the signal sequence and the extracellular region of mouse EphA2 were amplified by RT-PCR with total RNA derived from tissue, and cloned into pcDNA 3.1 vector having the DNA sequence encoding Fc and histidine tag to construct a mouse EphA2 extracellular region-Fc-His protein expression vector.

Next, each of mouse Eph receptor extracellular region-Fc-His protein expression vectors was introduced into Expi293F cells (Gibco/ThermoFisher) with Expi293 expression system (Gibco/ThermoFisher). After 5 days of culture (5% CO2, 37° C., 120 rpm), the culture supernatant was recovered, and this was centrifuged at room temperature, at 1500 rpm, and for 5 minutes. The centrifuged supernatant was filtered with a 0.45 μm filter (Millipore).

For antibody B, the evaluation of the binding activity of mouse Eph receptor was performed following the steps below.

Rabbit anti-6-His antibody (Bethyl Laboratories) was coated onto the wells of a 96-well plate (Nunc). After incubating at 4° C. overnight, wells were blocked at room temperature for one hour with 1% Block ACE (DS Pharma Biomedical). After washing three times with 0.05% Tween 20/PBS (Thermo SCIENTIFIC), each of mouse Eph receptor extracellular region-Fc-His proteins (final concentration 1 nM) was seeded in each well, and this was incubated at room temperature for one hour. After washing three times, human IgG solution (100 μg/mL, Sigma) and antibody B (10 μg/mL) were added to the wells, and this was incubated at room temperature for one hour. Horseradish peroxidase-labeled goat anti-human Kappa Light Chain antibody (IBL) was added, and this was incubated at room temperature for one hour. After washing three times, TMBZ (3,3',5,5'-tetramethylbenzidine, Sigma) solution was added to the wells, and upon confirmation of a moderate amount of coloring, an equal amount of the stop solution (1N $H_2SO_4$, Wako Pure Chemical) was added to the wells, and absorbance at 450 nm was read with a microplate reader (PerkinElmer).

Figure 17:
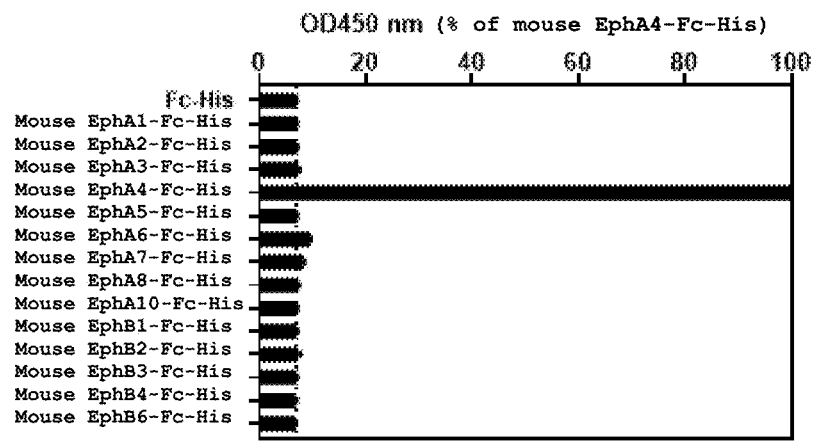
FIG. 17 shows the selectivity of the humanized anti-EphA4 monoclonal antibody (antibody B) against mouse Eph receptor.

Among the mouse Eph receptor family, antibody B had specific binding activity only towards mouse EphA4 (FIG. 17).

Example 8: Reactivity of Humanized Anti-EphA4 Monoclonal Antibody Against Mouse, Rat, Monkey, and Human EphA4

For antibody B, the evaluation of the binding activity with various EphA4 was performed following the steps below.

Anti-alkaline phosphatase antibody (Thermo SCIENTIFIC) was coated onto the wells of a 96-well plate (Nunc). After incubating at 4° C. overnight, wells were blocked at room temperature for one hour with 1% Block ACE (DS Pharma Biomedical). After washing three times with 0.05% Tween 20/PBS (Thermo SCIENTIFIC), mouse, rat, monkey, and human EphA4 extracellular region-SEAP-His proteins (final concentration 1 nM) were seeded in the wells, and this was incubated at room temperature for one hour. After washing three times, human IgG solution (100 μg/mL, Mitsubishi Pharma Corporation) and antibody B (0, 0.00013, 0.00064, 0.0032, 0.016, 0.08, 0.4, 2, and 10 μg/mL) were added to the wells, and this was incubated at room temperature for one hour. Horseradish peroxidase-labeled donkey anti-human IgG antibody (Jackson ImmunoResearch Laboratories) was added, and this was incubated at room temperature for one hour. After washing three times, TMBZ (3,3',5,5'-tetramethylbenzidine, Sigma) solution was added to the wells, and upon confirmation of a moderate amount of coloring, an equal amount of the stop solution (1N $H_2SO_4$, Wako Pure Chemical) was added to the wells, and absorbance at 450 nm was read with a microplate reader (PerkinElmer).

Figure 18:
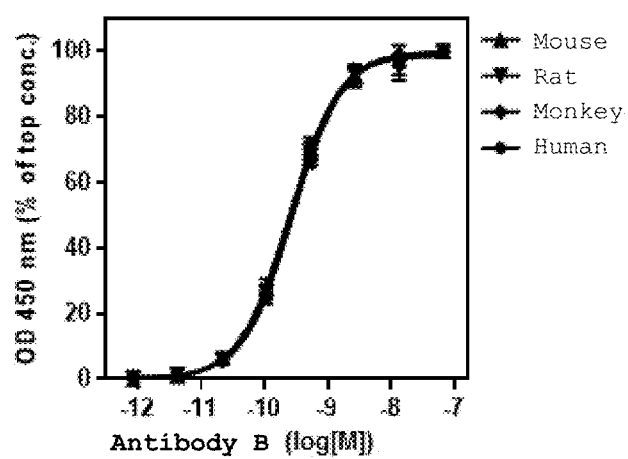
FIG. 18 shows the reactivity of the humanized anti-EphA4 monoclonal antibody (antibody B) against mouse, rat, monkey, and human EphA4.

Antibody B had equivalent binding activity in all of mouse, rat, monkey, and human EphA4 (FIG. 18).

Example 9: Reactivity of Humanized Anti-EphA4 Monoclonal Antibody Against Human EphA4 Extracellular Region, Ligand Binding Domain, Fibronectin Type III Domain 1, Fibronectin Type III Domain 2

For antibody B obtained in Example 1, the evaluation of the binding activity with various domains in human EphA4 was performed following the steps below.

Rabbit anti-6-His antibody (Bethyl Laboratories) was coated onto the wells of a 96-well plate (Nunc). After incubating at 4° C. overnight, wells were blocked at room temperature for one hour with 1% Block ACE (DS Pharma Biomedical). After washing twice with 0.02% Tween 20/PBS (Nacalai Tesque), human EphA4 extracellular region-MBP-His protein, human EphA4 ligand binding domain-MBP-His protein, human EphA4 fibronectin type III domain 1-MBP-His protein, and human EphA4 fibronectin type III domain 2-MBP-His protein (final concentration 10 nM) were seeded in the wells, and this was incubated at room temperature for one hour. After washing three times, antibody B (final concentration 10 nM) was added to the wells, and this was incubated at room temperature for one hour. Horseradish peroxidase-labeled rabbit anti-human IgG Fcγ fragment antibody (Jackson ImmunoResearch Laboratories) was added, and this was incubated at room temperature for one hour. After washing five times, TMB (KPL) solution was added to the wells, and upon confirmation of a moderate amount of coloring, an equal amount of the stop solution (2 N $H_2SO_4$, Wako Pure Chemical) was added to the wells. Absorbance at 450 nm and 650 nm were read by a microplate reader (PerkinElmer).

Figure 19:
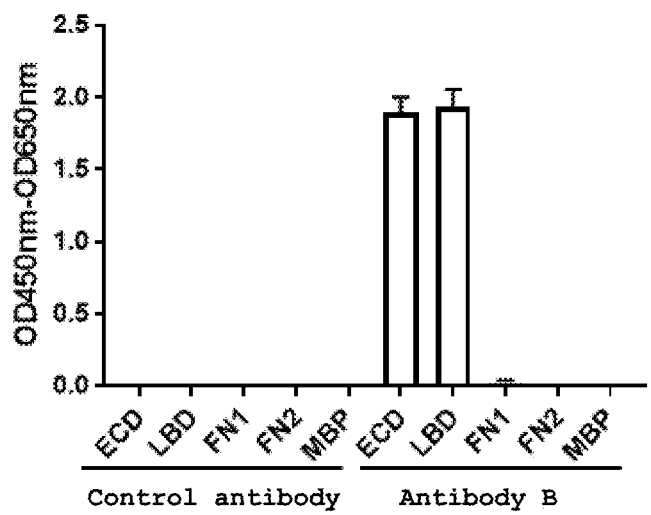
FIG. 19 shows the reactivity of the humanized anti-EphA4 monoclonal antibody (antibody B) against human EphA4 extracellular region (ECD), ligand binding domain (LBD), fibronectin type III domain 1 (FN1), and fibronectin type III domain 2 (FN2).

Antibody B had binding activity for human EphA4 extracellular region (ECD) and ligand binding domain (LBD) (FIG. 19). There was no reaction for fibronectin type III domain 1 (FN1) and fibronectin type III domain 2 (FN2). Accordingly, it was found that antibody B specifically binds to the ligand binding domain of the human EphA4 extracellular region.

Example 10: Effect of Humanized Anti-EphA4 Monoclonal Antibody on Increasing the Number of Spines in the Hippocampus Neuron Preparation of rat hippocampus neurons was performed as described in Reference Example 1 (B). Rat hippocampus neurons were introduced with EGFP gene employing Nucleofector (Lonza), and seeded in a 24-well plate (Falcon) containing a cover glass (Matsunami Glass Industries) coated with poly-L-lysine.

The counting of spine employing hippocampus neurons was performed following the steps below. Rat hippocampus neurons introduced with EGFP at culture Day 13 seeded in a 24-well plate (Falcon) containing a cover glass (Matsunami Glass Industries) coated with poly-L-lysine were treated with control antibody (human $IgG_2$; Sigma) or antibody B (6.7 and 20 nM) for 24 hours. The cover glass was then transferred to 2% PFA (Wako Pure Chemical)/4% sucrose (Wako Pure Chemical)/PBS, and this was left standing for 20 minutes to fix the cells. After removing the fixative solution and washing the cells three times with PBS, 0.252 Triton X-100 (Wako Pure Chemical)/PBS was added, and cell permeabilization was performed for 15 minutes. The solution was removed, the cover glass was transferred to 2% BSA (Sigma)/0.25% Triton X-100/OPTI-MEM (GIBCO) and subjected to one hour of blocking, after which anti-GFP antibody (Nacalai Tesque) was allowed to react for 1.5 hours. After removing the primary antibody solution and washing three times with PBS, the secondary antibody was allowed to react for one hour. After removing the secondary antibody solution and washing three times with PBS, Prolong Gold antifade reagent (Molecular probes) was added for mounting, and observation was performed with LSM800 (ZEISS). The experiment described above was carried out three times, and for each experiment, neurons were extracted from two cover glasses, spines on each dendrite were counted with image analysis software Imaris® (Bitplane), and the number of spines per 10 µm for each neuron was calculated.

Figure 20:
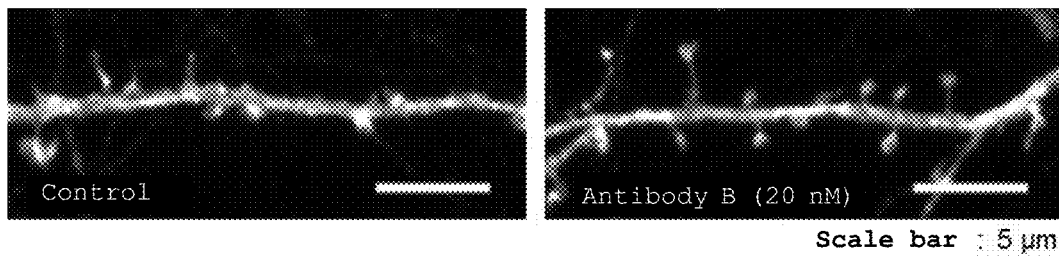
FIG. 20 shows the effect of the humanized anti-EphA4 monoclonal antibody (antibody B) on increasing the number of spines in the hippocampus neuron.
Figure 20:
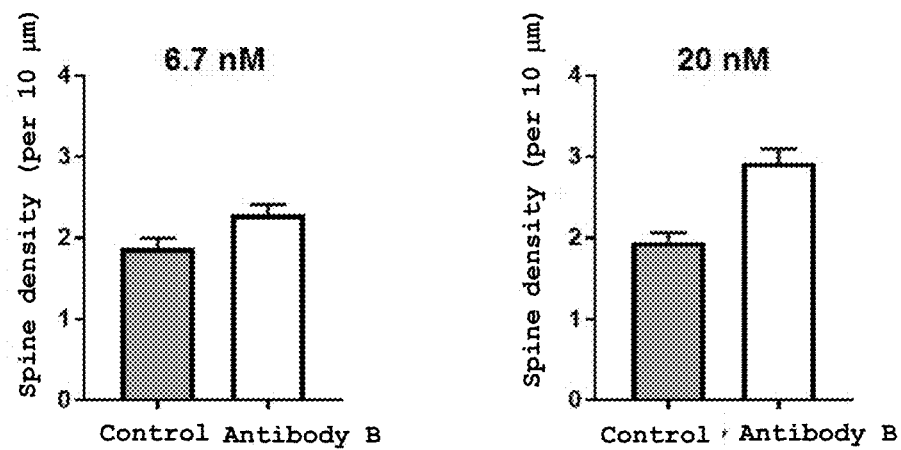

Antibody B increased the number of spines in the hippocampus neuron (FIG. 20). This result show that antibody B has the activity to stabilize spines in hippocampus neurons.

Example 11: Human EphA4 Cleavage Enhancement Activity of Humanized Anti-EphA4 Monoclonal Antibody For antibody B obtained in Example 1, the evaluation of cleavage enhancement activity on human EphA4 was performed following the steps below.

Preparation of rat hippocampus neurons was performed as described in Reference Example 1 (B). Rat hippocampus neurons were introduced with a human EphA4-HA protein expression vector employing Nucleofector (Lonza), and seeded in a 96-well dish (Falcon) coated with poly-L-lysine. The seeded rat hippocampus neurons were treated with antibody B (6.7, 20, and 67 nM) and γ selectase inhibitory drug Compound E (50 nM, Enzo Life Sciences). About twenty-four hours later, this was washed with PBS (Wako Pure Chemical), SDS sample buffer (Laemmli sample buffer (Bio-Rad) and 5% 2-mercaptoethanol (Bio-Rad)) was added to recover the cells, and this was boiled for 5 minutes. SDS-PAGE was performed with this sample, western blotting with rat anti-HA monoclonal antibody (Roche) was performed, the band strength was quantified, and the value of EphA4 C-terminal fragment/full length EphA4 was calculated.

Figure 21:
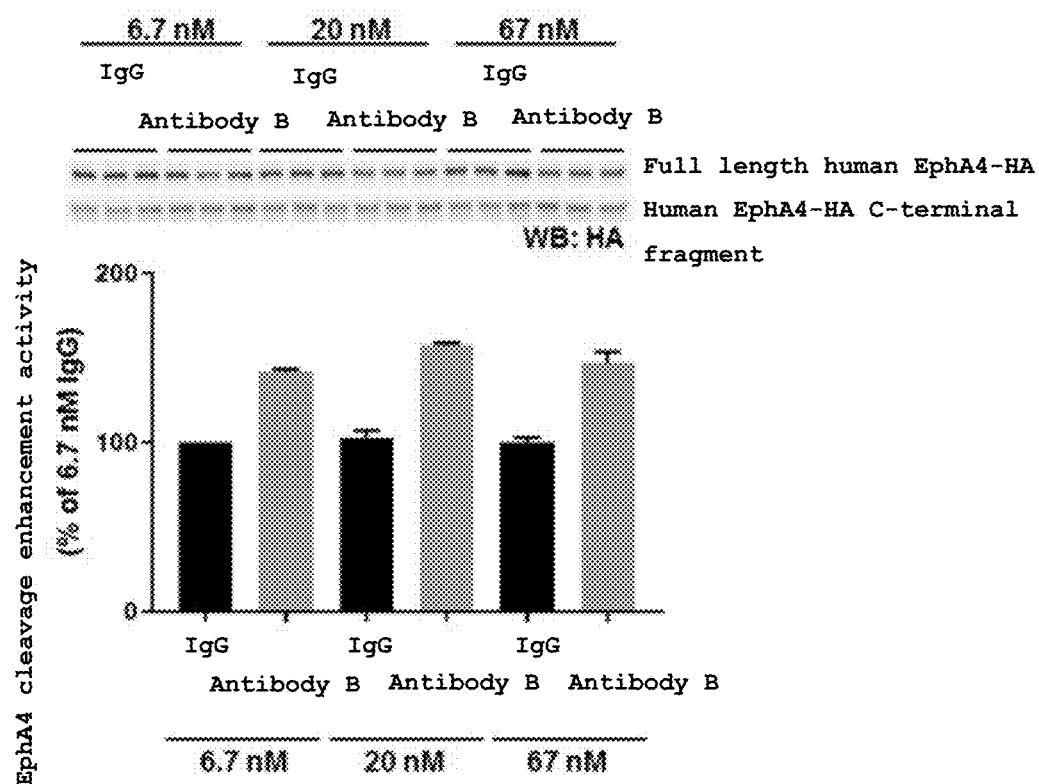
FIG. 21 shows human EphA4 cleavage enhancement activity of the humanized anti-EphA4 monoclonal antibody (antibody B) in the hippocampus neuron.

Antibody B enhanced human EphA4 cleavage reaction in hippocampus neurons (FIG. 21).

Example 12: Involvement of MMP and ADAM Against the Effect of Humanized Anti-EphA4 Monoclonal Antibody on Increasing the Number of Spines in the Hippocampus Neuron Preparation of rat hippocampus neurons was performed as described in Reference Example 1 (B). A part of rat hippocampus neurons were introduced with EGFP gene employing Nucleofector (Lonza), and seeded in a 24-well plate (Falcon) containing a cover glass (Matsunami Glass Industries) coated with poly-L-lysine.

The counting of spine employing hippocampus neurons was performed following the steps below. Rat hippocampus neurons introduced with EGFP at culture Day 13 seeded in a 24-well plate (Falcon) containing a cover glass (Matsunami Glass Industries) coated with poly-L-lysine were treated with control antibody (human IgG$_2$; Sigma) or antibody B (20 nM), as well as DMSO (Sigma) or MMP and ADAM inhibitor GM6001 (2.5 µM, MedChemExpress) for 24 hours. The cover glass was then transferred to 2% PFA (Wako Pure Chemical)/4% sucrose (Wako Pure Chemical)/PBS, and this was left standing for 20 minutes to fix the cells. After removing the fixative solution and washing the cells three times with PBS, 0.25% Triton X-100 (Wako Pure Chemical)/PBS was added, and cell permeabilization was performed for 15 minutes. The 0.25% Triton X-100/PBS was removed, the cover glass was transferred to 2% BSA (Sigma)/0.25% Triton X-100/OPTI-MEM (GIBCO) and subjected to one hour of blocking, after which anti-GFP antibody (Nacalai Tesque) was allowed to react for 1.5 hours. After removing the primary antibody solution and washing three times with PBS, the secondary antibody was allowed to react for one hour. After removing the secondary antibody solution and washing three times with PBS, Prolong Gold antifade reagent (Molecular probes) was added for mounting, and observation was performed with LSM800 (ZEISS). The experiment described above was carried out three times, and for each experiment, neurons were extracted from two cover glasses, spines on each dendrite were counted with image analysis software Imaris® (Bitplane), and the number of spines per 10 µm for each neuron was calculated.

Figure 22:
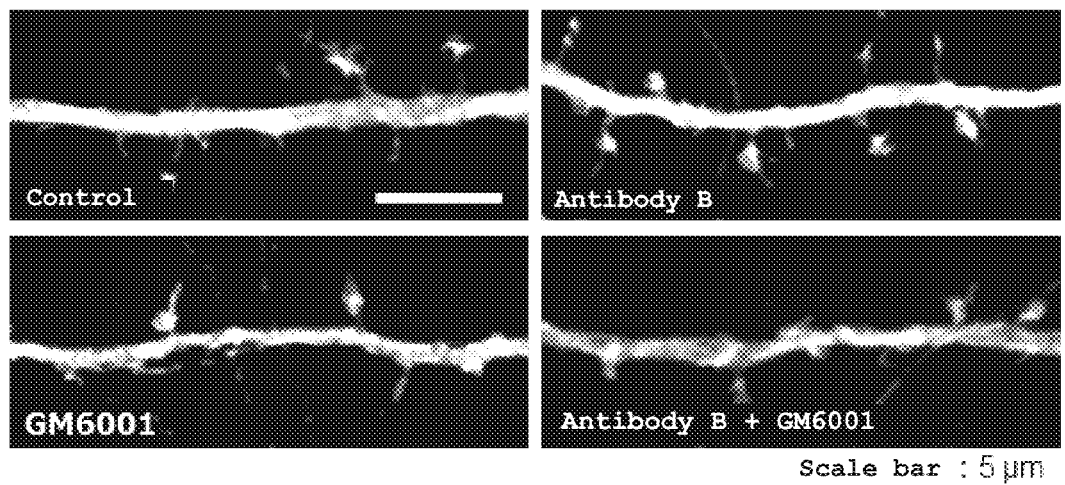
FIG. 22 shows the effect of the humanized anti-EphA4 monoclonal antibody (antibody B) via MMP and ADAM on increasing the number of spines in the hippocampus neuron.
Figure 22:
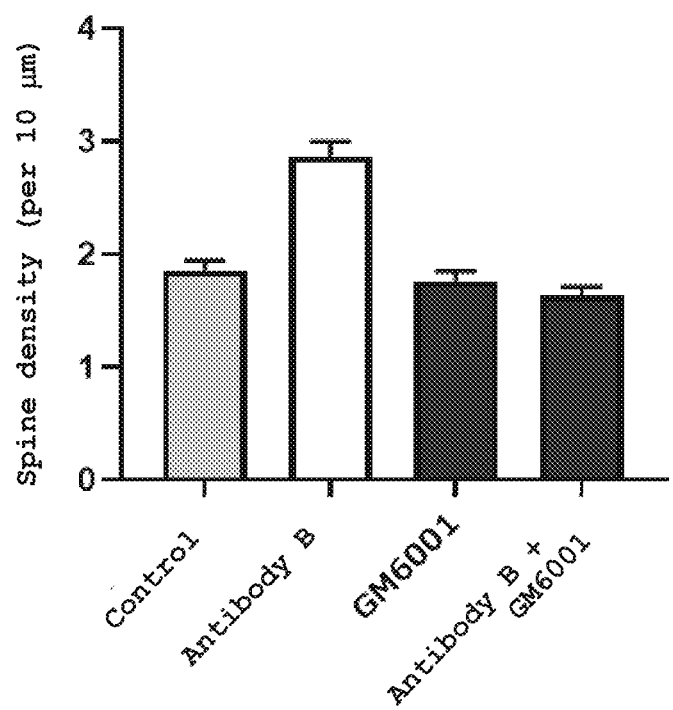

The increase in the number of spines in the hippocampus neuron by antibody B was inhibited by simultaneous treatment with GM6001 (FIG. 22). This result shows that antibody B has spine stabilization activity via MMP and ADAM in hippocampus neurons.

Example 13: Effect of Humanized Anti-EphA4 Monoclonal Antibody to Suppress Tau Phosphorylation In Vivo The evaluation of the effect to suppress tau phosphorylation in vivo employing tau transgenic mouse (rTg4510) was performed following the steps below. Tau transgenic mice (rTg4510) were subcutaneously administered twice a week from 20 to 26 weeks-old with antibody B at a dose of 100 mg/kg (10 mL/kg). PBS (Wako Pure Chemical) was subcutaneously administered at 10 mL/kg for the control group. On 3.5 days after the final administration, mice were anesthetized with 2-2.5% isoflurane inhalation anesthetic drug (Intervet) and a mix of three types of anesthetic drugs (4.0 mg/kg of Dormicum (Astellas Pharma), 0.3 mg/kg of Domitor (Nippon Zenyaku Kogyo), and 5.0 mg/kg of Vetorphale (Meiji Seika Pharma)), perfusion was performed under anesthesia with PBS (Wako Pure Chemical) containing 3 units/mL of heparin (Ajinomoto) and 1% phosphatase inhibitor cocktail (Nacalai Tesque), and the cerebral hemisphere of mice was resected. The cerebral hemisphere collected was fixed at 4° C. while shaking overnight immersed in 2 paraformaldehyde (TAAB)/0.1 M phosphate buffer (Wako Pure Chemical). The cerebral hemisphere was substituted with 10% sucrose (Wako Pure Chemical)/0.1 M phosphate buffer (Wako Pure Chemical) and subsequently 20% sucrose/0.1 M phosphate buffer (Wako Pure Chemical), and then embedded in Tissue-Tek O.C.T. Compound (Sakura Finetek Japan)/20% sucrose, and frozen employing an aluminum block cooled with liquid nitrogen. Slices of the cerebral hemisphere were created at a thickness of 7 µm with cryostat CM1860 (Leica). The slices were adhered on a silane-coated slide glass (Muto Pure Chemicals), air-dried with cold air, and then placed in a sealed bag and stored at −80° C. The slide glass used for immunostaining was taken out from −80° C., air-dried with cold air, and then washed with PBS (Wako Pure Chemical), immersed in 1% BSA (Sigma)/10% normal donkey serum (Jackson ImmunoResearch Laboratories)/0.5% Triton X-100 (Wako Pure Chemical)/PBS solution, and subjected to one hour of blocking, after which anti-phosphorylated tau antibody AT8 (Fujirebio Europe N.V.) was allowed to react overnight at ordinary temperatures. After washing three times with PBS, the secondary antibody was allowed to react for one hour. After washing three times with PBS, Prolong Gold antifade reagent (Molecular probes) was placed on the slice and mounted, and observation was performed with LSM700 (ZEISS). The AT8 signal-positive area in the hippocampus CA1 stratum radiatum was measured with image analysis software Metamorph, and the proportion of the AT8-positive signal area against the total area was calculated.

Figure 23:
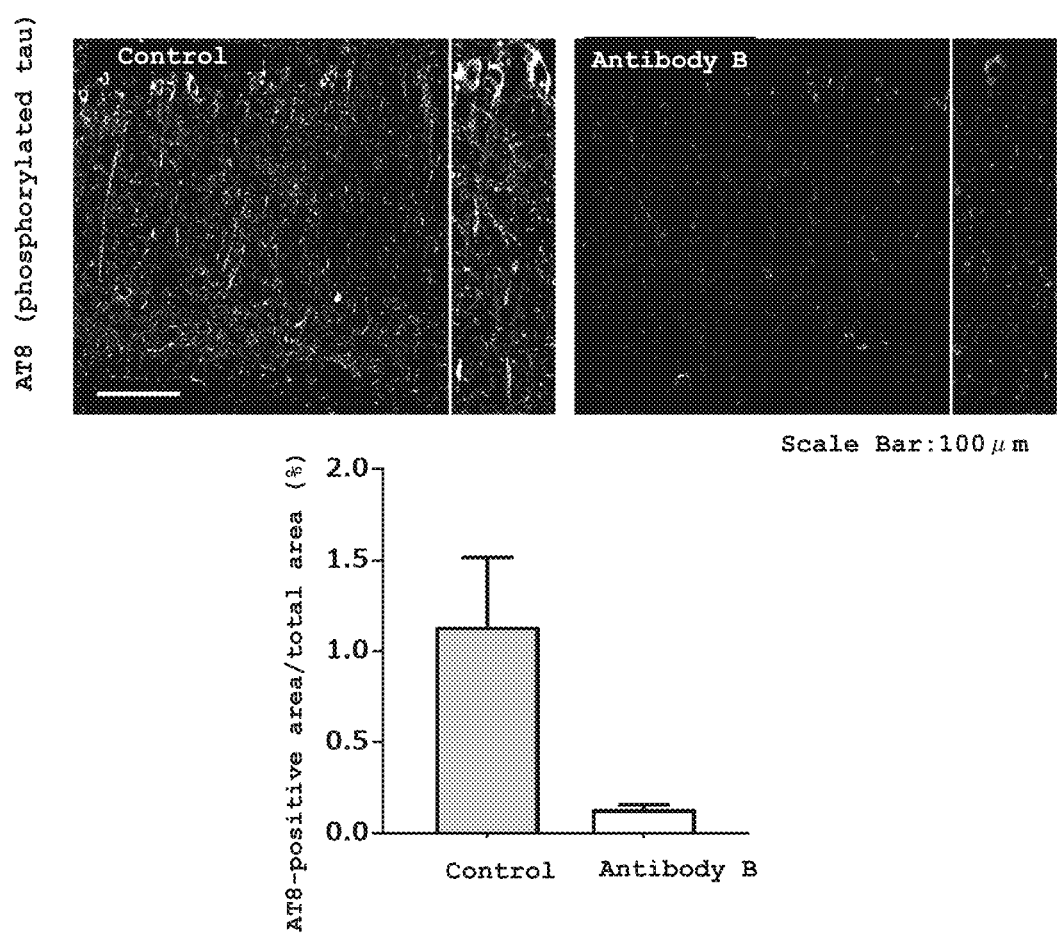
FIG. 23 shows the effect to suppress tau phosphorylation of the humanized anti-EphA4 monoclonal antibody (antibody B) in vivo.

Antibody B decreased the signal of phosphorylated tau in the hippocampus CA1 region (FIG. 23). This result shows that antibody B has the activity to suppress the progression of tau pathology in tau transgenic mouse (rTg4510).

The invention claimed is:

1. An anti-EphA4 antibody, wherein the anti-EphA4 antibody comprises heavy and light chains, and comprises:
   (a) a heavy chain CDR1 consisting of the amino acid sequence shown in SEQ ID NO. 44;
   (b) a heavy chain CDR2 consisting of the amino acid sequence shown in SEQ ID NO. 27;
   (c) a heavy chain CDR3 consisting of the amino acid sequence shown in SEQ ID NO. 28;
   (d) a light chain CDR1 consisting of the amino acid sequence shown in SEQ ID NO. 29;
   (e) a light chain CDR2 consisting of the amino acid sequence shown in SEQ ID NO. 30; and
   (f) a light chain CDR3 consisting of the amino acid sequence shown in SEQ ID NO. 31.

2. The anti-EphA4 antibody according to claim 1, wherein the anti-EphA4 antibody is humanized.

3. The anti-EphA4 antibody according to claim 1, wherein the heavy chain comprises a variable region consisting of the amino acid sequence shown in SEQ ID NO. 45, and the light chain comprises a variable region consisting of the amino acid sequence shown in SEQ ID NO. 46.

4. The anti-EphA4 antibody according to claim 1, wherein the heavy chain and the light chain comprise constant regions comprising amino acid sequences from a human antibody.

5. The anti-EphA4 antibody according to claim 4, wherein the constant region of the heavy chain is the constant region of human IgG.

6. The anti-EphA4 antibody according to claim 5, wherein the constant region of human IgG is the constant region of human IgG$_2$.

7. The anti-EphA4 antibody according to claim 6, wherein the constant region of human IgG$_2$ comprises the amino acid sequence shown in SEQ ID NO. 47.

8. The anti-EphA4 antibody according to claim 4, wherein the constant region of the light chain is the constant region of human Igκ.

9. The anti-EphA4 antibody according to claim 8, wherein the constant region of human Igκ comprises the amino acid sequence shown in SEQ ID NO. 48.

10. An anti-EphA4 antibody, wherein the anti-EphA4 antibody comprises heavy and light chains, the heavy chain comprises the amino acid sequence shown in SEQ ID NO. 59, and the light chain comprises the amino acid sequence shown in SEQ ID NO. 60.

11. A pharmaceutical composition comprising the anti-EphA4 antibody according to claim 1 and at least one pharmaceutically acceptable carrier.

12. An anti-EphA4 antibody, wherein the anti-EphA4 antibody comprises heavy and light chains, the heavy chain comprises the amino acid sequence shown in SEQ ID NO. 59, the light chain comprises the amino acid sequence shown in SEQ ID NO. 60, and the C-terminal lysine of the heavy chain is deleted.

13. A pharmaceutical composition comprising the anti-EphA4 antibody according to claim 10 and at least one pharmaceutically acceptable carrier.

14. A method for inhibiting tau phosphorylation in a subject having Alzheimer's disease, comprising administering to the subject an effective amount of the anti-EphA4 antibody according to claim 1.

15. A method for inhibiting tau phosphorylation in a subject having Alzheimer's disease, comprising administering to the subject an effective amount of the anti-EphA4 antibody according to claim 10.

* * * * *

UNITED STATES PATENT AND TRADEMARK OFFICE
CERTIFICATE OF CORRECTION

| | |
|---|---|
| PATENT NO. | : 10,947,313 B2 |
| APPLICATION NO. | : 16/915412 |
| DATED | : March 16, 2021 |
| INVENTOR(S) | : Eiji Inoue et al. |

It is certified that error appears in the above-identified patent and that said Letters Patent is hereby corrected as shown below:

On the Title Page

Page 2, Column 2, item (56) OTHER PUBLICATIONS
Line 6, delete "Brack" and insert -- Braak --.
Line 25, delete "2012." and insert -- 2012, 338 pages. --.
Line 27, delete "2017." and insert -- 2017, 196 pages. --.
Line 29, delete "2016." and insert -- 2016, 451 pages. --.
Line 33, delete "2020." and insert -- 2020, 176 pages. --.

Page 3, Column 1, item (56) OTHER PUBLICATIONS
Line 43, delete "and" and insert -- with --.

Page 3, Column 2, item (56) OTHER PUBLICATIONS
Line 52, delete "L-alanyl]S-phenylglycine" and insert -- L-alanyl]-S-phenylglycine --.

Page 7, Column 1, item (56) OTHER PUBLICATIONS
Line 3, after "Appln." insert -- No. --.
Line 3, delete "20201," and insert -- 2021, --.

In the Specification

Column 1
Line 21, delete "$(A\beta)_{1\text{-}42}$," and insert -- $(A\beta)_{(1\text{-}42)}$ --.

Column 3
Line 38, delete "IgK." and insert -- Igκ. --.
Line 40, delete "IgK" and insert -- Igκ --.

Column 7
Line 40, delete "IgG2" and insert -- $IgG_2$ --.

Signed and Sealed this
Eleventh Day of April, 2023

*Katherine Kelly Vidal*
Katherine Kelly Vidal
*Director of the United States Patent and Trademark Office*

CERTIFICATE OF CORRECTION (continued)
U.S. Pat. No. 10,947,313 B2

Column 8
Line 37, delete "10-M," and insert -- $10^{-7}$ M, --.

Column 14
Line 16, delete "aminoacids" and insert -- amino acids --.
Line 30, delete "IgK." and insert -- Igκ. --.

Column 19
Line 8, delete "0.02" and insert -- 0.02% --.

Column 21
Line 15, delete "VIWPGGSTDYNAAFMS" and insert -- VIWRGGSTDYNAAFMS --.

Column 26
Line 39, delete "Nm" and insert -- μm --.
Line 51, delete "11" and insert -- 1% --.

Column 28
Line 8, delete "1¹" and insert -- 1% --.
Line 26, delete "10" and insert -- 10% --.
Line 63, delete "Protein a" and insert -- Protein A --.

Column 29
Lines 25-26, delete "HILOAD26/60" and insert -- HILOAD 26/60 --.

Column 31
Line 6, delete "REGVH" and insert -- RFGVH --.
Line 8, delete "VIWRGGSTDYNAAFYMS" and insert -- VIWRGGSTDYNAAFMS --.
Line 9, delete "ESLEGVYYDYGYYSMDY" and insert -- ESLFGVYYDYGYYSMDY --.
Lines 24-25, delete "GTGATCTGGAGGGGAGGATCCGA CTACAACGCTGCTTTTATGAGC"
and insert -- GTGATCTGGAGGGGAGGATCCACCGA CTACAACGCTGCTTTTATGAGC --.

Column 33
Line 17, delete "0.024" and insert -- 0.02% --.

Column 34
Line 60, delete "3.1 rfcB" and insert -- 3.1_rfcB --.

Column 36
Line 65, delete "0.252" and insert -- 0.25% --.

Column 38
Line 51, delete "2" and insert -- 2% --.